US006277877B1

(12) United States Patent
Hoover et al.

(10) Patent No.: US 6,277,877 B1
(45) Date of Patent: Aug. 21, 2001

(54) SUBSTITUTED N-(INDOLE-2-CARBONYL) GLYCINAMIDES AND DERIVATES AS GLYCOGEN PHOSPHORYLASE INHIBITORS

(75) Inventors: Dennis J. Hoover, Stonington; Bernard Hulin; William H. Martin, both of Essex; Douglas Phillips; Judith L. Treadway, both of Gales Ferry, all of CT (US)

(73) Assignee: Pfizer, Inc., New York, NY (US)

( * ) Notice: Subject to any disclaimer, the term of this patent is extended or adjusted under 35 U.S.C. 154(b) by 0 days.

(21) Appl. No.: 09/638,938

(22) Filed: Aug. 15, 2000

Related U.S. Application Data

(62) Division of application No. 08/952,669, filed as application No. PCT/IB95/00442 on Jun. 6, 1995, now Pat. No. 6,107,329.

(51) Int. Cl.[7] ............... A01N 43/38; A01N 43/40; A01N 43/52; A61K 31/405

(52) U.S. Cl. ............... 514/415; 514/18; 514/419; 514/235; 514/323; 514/330; 514/385; 548/100

(58) Field of Search ............... 514/415, 18, 419, 514/235, 323, 330, 385; 548/100

(56) References Cited

U.S. PATENT DOCUMENTS

| | | | |
|---|---|---|---|
| 4,764,610 | 8/1988 | Zimmerman | 71/92 |
| 4,836,846 | 6/1989 | Zimmerman | 71/93 |
| 4,902,708 | 2/1990 | Kim | 514/419 |
| 4,904,846 | 2/1990 | Oscadal | 219/341 |
| 4,933,325 | 6/1990 | Hansen, Jr. et al. | 514/19 |
| 4,997,950 | 3/1991 | Murphy et al. | 548/303 |
| 5,034,376 | 7/1991 | Hoover et al. | 514/18 |
| 5,064,853 | 11/1991 | Gasc et al. | 514/419 |
| 5,089,638 | 2/1992 | Freidinger | 549/468 |
| 5,128,346 | 7/1992 | Nadzan et al. | 514/307 |
| 5,219,859 | 6/1993 | Festal et al. | 514/269 |
| 5,250,517 | 10/1993 | Branca et al. | 514/18 |
| 5,346,907 | 9/1994 | Kerwin, Jr. et al. | 514/912 |

FOREIGN PATENT DOCUMENTS

| | | |
|---|---|---|
| 4115468 | 11/1992 | (DE) . |
| 0080283 | 6/1983 | (EP) . |
| 0224151 | 6/1987 | (EP) . |
| 0283956 | 9/1988 | (EP) . |
| 0288965 | 11/1988 | (EP) . |
| 0336356 | 10/1989 | (EP) . |
| 0405506 | 1/1991 | (EP) . |
| 0431520 | 6/1991 | (EP) . |
| 0601459 | 6/1994 | (EP) . |
| JP3294253 | 12/1991 | (JP) . |
| WO8803022 | 5/1988 | (WO) . |
| WO9100725 | 1/1991 | (WO) . |
| WO9102719 | 3/1991 | (WO) . |
| WO9112264 | 8/1991 | (WO) . |
| WO9113874 | 9/1991 | (WO) . |
| WO 93/01167 | * 1/1993 | (WO) . |
| WO9320099 | 10/1993 | (WO) . |
| WO9406755 | 3/1994 | (WO) . |
| WO9407815 | 4/1994 | (WO) . |
| WO9426707 | 11/1994 | (WO) . |
| WO9534538 | 12/1995 | (WO) . |

OTHER PUBLICATIONS

Martin, J.L. et al. "Biochemistry" 1991, 30, 10101.
Kavinsky, P. J. et al. "Biol. Chem." 1978, 253, 3343–3351 and 9102–9106.
Blundell, T. B. et al. "Diabetologia" 1992, 35, Suppl. 2, S69–S76.
Nadzan, A. M. et al. "Design of Cholecystokinin Analogs with High Affinity and Selectivity for Brain CCK Receptors" pp. 100–102.
Chemical abstr., vol. 90, No. 19, May 07, 1979 (Columbus, Ohio, USA p. 587, column 2, the abstract No. 151917p, PIGULLA, J. et al., "Preparation of indole–2–carboxamides and esters of (indole–2–ylcarbonylamino)carboxylic acids by the imidazolide method," Arch. Pharm. (Weinheim, Ger.) 1979, 312(1), 12–18 (Ger.).
Chemical Abstrl., vol. 90, No. 3, Jan. 15, 1979 (Columbus, OH, USA), p. 636, column 1, the abstract No. 22858w, PIGULLA, J. et al., "Azepinoindoles, III. Cyclization of N–(2–indolylcarbonyl)–β–amino acids to azepino(3,4–b)indolediones", Justus Liebigs Ann. Chem. 1978, (9), 1390–8.
Allard, M. F. et al. "Am. J. Physiol." 1994, 267, H66–H74.
Farris P. L. et al.,Science 1984, vol. 226, pp. 1215–1217, "Morphine Analgesia Potentiated but Tolerance Not Affected by Active Immunization Against Sholecystokinin".
Bock, Mark G. et al. "J. Med. Chem." 1989, 32, pp. 13–16, "Benzodiazepine Gastrin and Brain Cholecystokinin Receptor Ligands: L–365,260".

(List continued on next page.)

Primary Examiner—Jezia Riley
(74) Attorney, Agent, or Firm—Peter C. Richardson; Gregg C. Benson; A. Dean Olson

(57) ABSTRACT

Compounds of Formula (I)

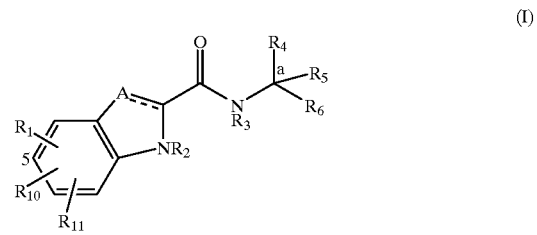

wherein $R_6$ is carboxy, $(C_1-C_8)$alkoxycarbonyl, benzyloxycarbonyl, $C(O)NR_8R_9$ or $C(O)R_{12}$ as glycogen phosphorylase inhibitors, pharmaceutical compositions containing such inhibitors and the use of such inhibitors to treat diabetes, hyperglycemia, hypercholesterolemia, hypertension, hyperisulinemia, hyperlipidemia, atherosclerosis and myocardial ischemia in mammals.

13 Claims, No Drawings

OTHER PUBLICATIONS

Shroff, James R. et al. "J. Med. Chem." 1982, 25, pp. 359–362, "Chemistry and Hypoglycemic Activity of N–(((Dialkylamino)alkoxy)phenyl)benzamidines".

Burn, Peter et al. "J. Med. Chem. " 1982, 25, pp. 363–368, "Synthesis and Dopaminergic Properties of Some exo–and endo–2–Aminobenzonorbornenes Designed as Rigid Analogues of Dopamine".

73:110093x, Saito et al., Chemistry of diborance and sodium borohydride. VII. Reduction of α–amino acid amides with sodium borohydride., vol. 73, 1970.

86:16946z, Grathwohl et al., The X–Pro peptide bond as an NMR probe for conformational studies of flexible linear peptides., vol. 86, 1977.

98:4791e, Brantl, Victor, Pharmacologically active peptides containing N–terminal phenylalanine. vol. 98, 1983.

103:215774m, Ando et al., Syntheses of cyclic decapeptides with four ornithyl residues related to gramicidin S., vol. 103, 1985.

104:221198p, Okada et al., Inhibition of α–chymotrypsin by Suc–L–Tyr–D–Leu–D–Phe–pNA, a stereoisomer of a specific substrate., vol. 104, 1986.

108:150948c, Tsuge et al., Lithium bromide–triethylamine induced cyclo addition of N–alkylidene 2–amino esters and amides to electro n–deficient olefins with high regio–and stereoselectivity., vol. 108, 1988.

114:94966s, Weiss et al, Effects of amino acid amides and aminothiols on 3–mercaptoproprionic acid–induced convulsions and phency clidine–induced hyperactivity in mice., vol. 114, 1991.

Joachim Pigulla, et al., Arch. Pharm. (Weinheim) 312:12–18, 1979, "Preparation of indole–2–carboxamides and esters of (indol–2–yl–carbonylamino)carboxylic acids by the imidazolide method".

Joachim Pigulla, et al., Liebigs Ann. Chem. 1978:1390–1398, "Azepinoindoles, III[1] Synthesis of azepino[3,4–b]indolediones by cyclization of N–(2–indolylcarbonyl)–β–amino acids[2]".

James F. Kerwin, Jr., et al., J. Med. Chem. 1991, 34, 3350–3359, Cholecystokinin Antagonists: (R)–Tryptophan–Based Hybrid Antagonists of High Affinity and Selectivity for CCK–A Receptors.

* cited by examiner

SUBSTITUTED N-(INDOLE-2-CARBONYL) GLYCINAMIDES AND DERIVATES AS GLYCOGEN PHOSPHORYLASE INHIBITORS

This application is a divisional of U.S. application Ser. No. 08/952,669 filed on Dec. 2, 1997 which issued as U.S. Pat. No. 6,107,329 on Aug. 22, 2000 and was filed under 35 U.S.C. §371 based on PCT/IBT95/00442 which was filed on Jun. 6, 1995 and is now abandoned.

BACKGROUND OF THE INVENTION

This invention relates to glycogen phosphorylase inhibitors, pharmaceutical compositions containing such inhibitors and the use of such inhibitors to treat diabetes, hyperglycemia, hypercholesterolemia, hypertension, hyperinsulinemia, hyperlipidemia, atherosclerosis and myocardial ischemia in mammals.

In spite of the early discovery of insulin and its subsequent widespread use in the treatment of diabetes, and the later discovery of and use of sulfonylureas (e.g. Chlorpropamide™ (Pfizer), Tolbutamide™ (Upjohn), Acetohexamide™ (E. I. Lilly), Tolazamide™ (Upjohn)) and biguanides (e.g. Phenformin™ (Ciba Geigy), Metformin™ (G. D. Searle)) as oral hypoglycemic agents, the treatment of diabetes remains less than satisfactory. The use of insulin, necessary in about 10% of diabetic patients in which synthetic hypoglycemic agents are not effective (Type I diabetes, insulin dependent diabetes mellitus), requires multiple daily doses, usually by self injection. Determination of the proper dosage of insulin requires frequent estimations of the sugar in urine or blood. The administration of an excess dose of insulin causes hypoglycemia, with effects ranging from mild abnormalities in blood glucose to coma, or even death. Treatment of non-insulin dependent diabetes mellitus (Type II diabetes, NIDDM) usually consists of a combination of diet, exercise, oral agents, e.g. sulfonylureas, and in more severe cases, insulin. However, the clinically available hypoglycemics can have other side effects which limit their use. In any event, where one of these agents may fail in an individual case, another may succeed. A continuing need for hypoglycemic agents, which may have fewer side effects or succeed where others fail, is clearly evident.

Atherosclerosis, a disease of the arteries, is recognized to be the leading cause of death in the United States and Western Europe. The pathological sequence leading to atherosclerosis and occlusive heart disease is well known. The earliest stage in this sequence is the formation of "fatty streaks" in the carotid, coronary and cerebral arteries and in the aorta. These lesions are yellow in color due to the presence of lipid deposits found principally within smooth-muscle cells and in macrophages of the intima layer of the arteries and aorta. Further, it is postulated that most of the cholesterol found within the fatty streaks, in turn, give rise to development of the "fibrous plaque", which consists of accumulated intimal smooth muscle cells laden with lipid and surrounded by extra-cellular lipid, collagen, elastin and proteoglycans. The cells plus matrix form a fibrous cap that covers a deeper deposit of cell debris and more extra cellular lipid. The lipid is primarily free and esterified cholesterol. The fibrous plaque forms slowly, and is likely in time to become calcified and necrotic, advancing to the "complicated lesion" which accounts for the arterial occlusion and tendency toward mural thrombosis and arterial muscle spasm that characterize advanced atherosclerosis.

Epidemiological evidence has firmly established hyperlipidemia as a primary risk factor in causing cardiovascular disease (CVD) due to atherosclerosis. In recent years, leaders of the medical profession have placed renewed emphasis on lowering plasma cholesterol levels, and low density lipoprotein cholesterol in particular, as an essential step in prevention of CVD. The upper limits of "normal" are now known to be significantly lower than heretofore appreciated. As a result, large segments of Western populations are now realized to be at particular high risk. Such Independent risk factors include glucose intolerance, left ventricular hypertrophy, hypertension, and being of the male sex. Cardiovascular disease is especially prevalent among diabetic subjects, at least in part because of the existence of multiple independent risk factors in this population. Successful treatment of hyperlipidemia in the general population, and in diabetic subjects in particular, is therefore of exceptional medical importance.

Hypertension (or high blood pressure) is a condition which occurs in the human population as a secondary symptom to various other disorders such as renal artery stenosis, pheochromocytoma or endocrine disorders. However, hypertension is also evidenced in many patients in whom the causative agent or disorder is unknown. While such "essential" hypertension is often associated with disorders such as obesity, diabetes and hypertriglyceridemia, the relationship between these disorders has not been elucidated. Additionally, many patients display the symptoms of high blood pressure in the complete absence of any other signs of disease or disorder.

It is known that hypertension can directly lead to heart failure, renal failure and stroke (brain hemorrhaging). These conditions are capable of causing short-term death in a patient. Hypertension can also contribute to the development of atherosclerosis and coronary disease. These conditions gradually weaken a patient and can led to long-term death.

The exact cause of essential hypertension is unknown, though a number of factors are believed to contribute to the onset of the disease. Among such factors are stress, uncontrolled emotions, unregulated hormone release (the renin, angiotensin, aldosterone system), excessive salt and water due to kidney malfunction, wail thickening and hypertrophy of the vasculature resulting in constricted blood vessels and genetic factors.

The treatment of essential hypertension has been undertaken bearing the foregoing factors In mind. Thus a broad range of beta-blockers, vasoconstrictors, angiotensin converting enzyme inhibitors and the like have been developed and marketed as antihypertensives. The treatment of hypertension utilizing these compounds has proven beneficial in the prevention of short-interval deaths such as heart failure, renal failure and brain hemorrhaging. However, the development of atherosclerosis or heart disease due to hypertension over a long period of time remains a problem. This implies that although high blood pressure is being reduced, the underlying cause of essential hypertension is not responding to this treatment.

Hypertension has been associated with elevated blood insulin levels, a condition known as hyperinsulinemia. Insulin, a peptide hormone whose primary actions are to promote glucose utilization, protein synthesis and the formation and storage of neutral lipids, also acts to promote vascular cell growth and increase renal sodium retention, among other things. These latter functions can be accomplished without affecting glucose levels and are known causes of hypertension. Peripheral vasculature growth, for example, can cause constriction of peripheral capillaries; while sodium retention increases blood volume. Thus, the lowering of insulin levels in hyperinsulinemics can prevent abnormal vascular growth and renal sodium retention caused by high insulin levels and thereby alleviate hypertension.

Cardiac hypertrophy is a significant risk factor in the development of sudden death, myocardial infarction, and congestive heart failure. These cardiac events are due, at least in part, to increased susceptibility to myocardial injury after ischemia and reperfusion which can occur in outpatient as well as perioperative settings. There is an unmet medical need to prevent or minimize adverse myocardial perioperative outcomes, particularly perioperative myocardial infarction. Both non-cardiac and cardiac surgery are associated with substantial risks for myocardial infarction or death. Some 7 million patients undergoing non-cardiac surgery are considered to be at risk, with incidences of perioperative death and serious cardiac complications as high as 20–25% in some series. In addition, of the 400,000 patients undergoing coronary by-pass surgery annually, perioperative myocardial infarction is estimated to occur in 5% and death in 1–2%. There is currently no drug therapy in this area which reduces damage to cardiac tissue from perioperative myocardial ischemia or enhances cardiac resistance to ischemic episodes. Such a therapy is anticipated to be life-saving and reduce hospitalizations, enhance quality of life and reduce overall health care costs of high risk patients.

Hepatic glucose production is an important target for NIDDM therapy. The liver is the major regulator of plasma glucose levels in the post absorptive (fasted) state, and the rate of hepatic glucose production in NIDDM patients is significantly elevated relative to normal individuals. Likewise, in the postprandial (fed) state, where the liver has a proportionately smaller role in the total plasma glucose supply, hepatic glucose production is abnormally high in NIDDM patients.

Glycogenolysis is an important target for interruption of hepatic glucose production. The liver produces glucose by glycogenolysis (breakdown of the glucose polymer glycogen) and gluconeogenesis (synthesis of glucose from 2- and 3-carbon precursors). Several lines of evidence indicate that glycogenolysis may make an important contribution to hepatic glucose output in NIDDM. First, in normal post absorptive man, up to 75% of hepatic glucose production is estimated to result from glycogenolysis. Second, patients having liver glycogen storage diseases, including Hers' disease (glycogen phosphorylase deficiency), display episodic hypoglycemia. These observations suggest that glycogenolysis may be a significant process for hepatic glucose production.

Glycogenolysis is catalyzed in liver, muscle, and brain by tissue-specific isoforms of the enzyme glycogen phosphorylase. This enzyme cleaves the glycogen macromolecule to release glucose-1-phosphate and a new shortened glycogen macromolecule. Two types of glycogen phosphorylase inhibitors have been reported to date: glucose and glucose analogs [Martin, J. L. et al. *Biochemistry* 1991, 30, 10101] and caffeine and other purine analogs [Kasvinsky, P. J. et al. *J. Biol. Chem.* 1978, 253, 3343–3351 and 9102–9106]. These compounds, and glycogen phosphorylase inhibitors in general, have been postulated to be of potential use for the treatment of NIDDM by decreasing hepatic glucose production and lowering glycemia. [Blundell, T. B. et al. *Diabetologia* 1992, 35, Suppl. 2, 569–576 and Martin et al. Biochemistry 1991, 30, 10101].

The mechanism(s) responsible for the myocardial injury observed after ischemia and reperfusion is not fully understood. It has been reported (M. F. Allard, et al. Am. J. Physiol. 267, H66–H74, 1994) that "pre ischemic glycogen reduction . . . is associated with improved post ischemic left ventricular functional recovery in hypertrophied rat hearts".

Thus, although there are a variety of hyperglycemia, hypercholesterolemia, hypertension, hyperinsulinemia, hyperlipidemia, atherosclerosis and myocardial ischemia therapies there is a continuing need and a continuing search in this field of art for alternative therapies.

SUMMARY OF THE INVENTION

This invention is directed to a glycogen phosphorylase Inhibitor compound of Formula I useful for the treatment of diabetes, hyperglycemia, hypercholesterolemia, hyperinsulinemia, hypertension, hyperlipidemia, atherosclerosis and myocardial ischemia.

The compounds of this invention have the Formula I

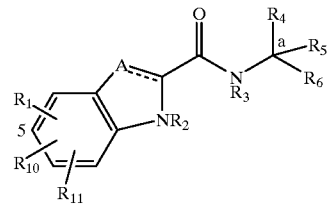

Formula 1 and the pharmaceutically acceptable salts and prodrugs thereof wherein the dotted line (---) is an optional bond;

A is —C(H)=, —C(($C_1$–$C_4$)alkyl)=, —C(halo)= or —N=, when the dotted line (---) is a bond, or A is methylene or —CH(($C_1$–$C_4$)alkyl)—, when the dotted line (---) is not a bond;

$R_1$, $R_{10}$ or $R_{11}$ are each independently H, halo, cyano, 4-, 6-, or 7-nitro, ($C_1$–$C_4$)alkyl, ($C_1$–$C_4$)alkoxy, fluoromethyl, difluoromethyl or trifluoromethyl;

$R_2$ is H;

$R_3$ is H or ($C_1$–$C_6$)alkyl;

$R_4$ is H, methyl, ethyl, n-propyl, hydroxy($C_1$–$C_3$)alkyl, ($C_1$–$C_3$)alkoxy($C_1$–$C_3$)alkyl, phenyl($C_1$–$C_4$)alkyl, phenylhydroxy($C_1$–$C_4$)alkyl, (phenyl)(($C_1$–$C_4$)-alkoxy)($C_1$–$C_4$)alkyl, thien-2- or -3-yl($C_1$–$C_4$)alkyl or fur-2- or 3-yl($C_1$–$C_4$)alkyl wherein said $R_4$ rings are mono-, di- or tri-substituted independently on carbon with H, halo, ($C_1$–$C_4$)alkyl, ($C_1$–$C_4$)alkoxy, trifluoromethyl, hydroxy, amino, cyano or 4,5-dihydro-1H-imidazol-2-yl; or $R_4$ is pyrid-2-, -3- or -4-yl($C_1$–$C_4$)alkyl, thiazol-2-, -4- or -5-yl($C_1$–$C_4$)alkyl, imidazol-2-, -4- or -5-yl($C_1$–$C_4$) alkyl, pyrrol-2- or -3-yl($C_1$–$C_4$)alkyl, oxazol-2-, -4- or -5-yl($C_1$–$C_4$)alkyl, pyrazol-3-, -4- or -5-yl($C_1$–$C_4$) alkyl, isoxazol-3-, -4- or -5-yl($C_1$–$C_4$)alkyl, isothiazol-3-, -4- or -5-yl($C_1$–$C_4$)alkyl, pyridazin-3- or -4-yl ($C_1$–$C_4$)alkyl, pyrimidin-2-, -4-, -5- or -6-yl($C_1$–$C_4$) alkyl, pyrazin-2- or -3-yl($C_1$–$C_4$)alkyl, 1,3,5-triazin-2-yl($C_1$–$C_4$)alkyl; or indol-2-($C_1$–$C_4$)alkyl, wherein said preceding $R_4$ heterocycles are optionally mono- or di-substituted independently with halo, trifluoromethyl, ($C_1$–$C_4$)alkyl, ($C_1$–$C_4$)alkoxy, amino, hydroxy or cyano and said substituents are bonded to carbon; or $R_4$ is $R_{15}$-carbonyloxymethyl, wherein said $R_{15}$ is phenyl, thiazolyl, imidazolyl, 1H-indolyl, furyl, pyrrolyl, oxazolyl, pyrazolyl, isoxazolyl, isothiazolyl, pyridyl, pyridazinyl, pyrimidinyl, pyrazinyl or 1,3,5-triazinyl and wherein said preceding $R_{15}$ rings are optionally mono- or di-substituted independently with halo, amino, hydroxy, $(C_1-C_4)$alkyl, $(C_1-C_4)$alkoxy or trifluoromethyl and said mono- or di-substituents are bonded to carbon;

$R_5$ is H, methyl, ethyl, n-propyl, hydroxymethyl or hydroxyethyl;

$R_6$ is carboxy, $(C_1-C_8)$alkoxycarbonyl, benzyloxycarbonyl, $C(O)NR_8R_9$ or $C(O)R_{12}$ wherein $R_8$ is H, $(C_1-C_6)$alkyl, cyclo$(C_3-C_6)$alkyl, cyclo$(C_3-C_6)$alkyl$(C_1-C_5)$alkyl, hydroxy or $(C_1-C_8)$alkoxy; and $R_9$ is H, cyclo$(C_3-C_8)$alkyl, cyclo$(C_3-C_8)$alkyl$(C_1-C_5)$alkyl, cyclo$(C_4-C_7)$alkenyl, cyclo$(C_3-C_7)$alkyl$(C_1-C_5)$alkoxy, cyclo$(C_3-C_7)$alkyloxy, hydroxy, methylene-perfluorinated$(C_1-C_8)$alkyl, phenyl, or a heterocycle wherein said heterocycle is pyridyl, furyl, pyrrolyl, pyrrolidinyl, oxazolyl, thiazolyl, imidazolyl, pyrazolyl, pyrazolinyl, pyrazolidinyl, isoxazolyl, isothiazolyl, pyranyl, pyridinyl, piperidinyl, morpholinyl, pyridazinyl, pyrimidinyl, pyrazinyl, piperazinyl, 1,3,5-triazinyl, benzothiazolyl, benzoxazolyl, benzimidazolyl, thiochromanyl or tetrahydrobenzothiazolyl wherein said heterocycle rings are carbon-nitrogen linked; or $R_9$ is $(C_1-C_6)$alkyl or $(C_1-C_8)$alkoxy wherein said $(C_1-C_6)$alkyl or $(C_1-C_8)$alkoxy is optionally monosubstituted with cyclo$(C_4-C_7)$alken-1-yl, phenyl, thienyl, pyridyl, furyl, pyrrolyl, pyrrolidinyl, oxazolyl, thiazolyl, imidazolyl, pyrazolyl, pyrazolinyl, pyrazolidinyl, isoxazolyl, isothiazolyl, pyranyl, piperidinyl, morpholinyl, thiomorpholinyl, 1-oxothiomorpholinyl, 1,1-dioxothiomorpholinyl, pyridazinyl, pyrimidinyl, pyrazinyl, piperazinyl, 1,3,5-triazinyl or indolyl and wherein said $(C_1-C_6)$alkyl or $(C_1-C_8)$alkoxy are optionally additionally independently mono- or di-substituted with halo, hydroxy, $(C_1-C_5)$alkoxy, amino, mono-N— or di-N,N—$(C_1-C_5)$alkylamino, cyano, carboxy, or $(C_1-C_4)$alkoxycarbonyl; and wherein the $R_9$ rings are optionally mono- or di-substituted independently on carbon with halo, $(C_1-C_4)$alkyl, $(C_1-C_4)$alkoxy, hydroxy, hydroxy$(C_1-C_4)$alkyl, amino$(C_1-C_4)$alkyl, mono-N— or di-N,N—$(C_1-C_4)$alkylamino$(C_1-C_4)$alkyl, $(C_1-C_4)$alkoxy$(C_1C_4)$alkyl, amino, mono-N— or di-N,N—$(C_1-C_4)$alkylamino, cyano, carboxy, $(C_1-C_5)$alkoxycarbonyl, carbamoyl, formyl or trifluoromethyl and said $R_9$ rings may optionally be additionally mono- or di-substituted independently with $(C_1-C_5)$alkyl or halo;

with the proviso that no quaternized nitrogen on any $R_9$ heterocycle is included;

$R_{12}$ is morpholino, thiomorpholino, 1-oxothiomorpholino, 1,1-dioxothiomorpholino, thiazolidin-3-yl, 1-oxothiazolidin-3-yl, 1,1-dioxothiazolidin-3-yl, pyrrolidin-1-yl, piperidin-1-yl, piperazin-1-yl, piperazin-4-yl, azetidin-1-yl, 1,2-oxazinan-2-yl, pyrazolidin-1-yl, isoxazolidin-2-yl, isothiazolidin-2-yl, 1,2-oxazetidin-2-yl, oxazolidin-3-yl, 3,4dihydroisoquinolin-2-yl, 1,3-dihydroIsoindol-2-yl, 3,4-dihydro-2H-quinol-1-yl, 2,3-dihydro-benzo[1,4]oxazin-4-yl, 2,3-dihydro-benzo[1,4]-thiazine-4-yl, 3,4-dihydro-2H-quinoxalin-1-yl, 3,4-dihydro-benzo[c][1,2]oxazin-1-yl, 1,4-dihydro-benzo[d][1,2]oxazin-3-yl, 3,4-dihydro-benzo[e][1,2]-oxazin-2-yl, 3H-benzo[d]isoxazol-2-yl, 3H-benzo[c]isoxazol-1-yl or azepan-1-yl, wherein said $R_{12}$ rings are optionally mono-, di- or tri-substituted independently with halo, $(C_1-C_5)$alkyl, $(C_1-C_5)$alkoxy, hydroxy, amino, mono-N— or di-N,N—$(C_1-C_5)$alkylamino, formyl, carboxy, carbamoyl, mono-N— or di-N,N—$(C_1-C_5)$alkylcarbamoyl, $(C_1-C_6)$alkoxy$(C_1-C_3)$alkoxy, $(C_1-C_5)$alkoxycarbonyl, benzyloxycarbonyl, $(C_1-C_5)$alkoxycarbonyl$(C_1C_5)$alkyl, $(C_1C_4)$alkoxycarbonylamino, carboxy$(C_1-C_5)$alkyl, carbamoyl$(C_1-C_5)$alkyl, mono-N— or di-N,N—$(C_1-C_5)$alkylcarbamoyl$(C_1-C_5)$alkyl, hydroxy$(C_1-C_5)$alkyl, $(C_1-C_4)$alkoxy$(C_1-_4)$alkyl, amino$(C_1C_4)$alkyl, mono-N—or di-N,N—$(C_1-C_4)$alkylamino$(C_1-C_4)$alkyl, oxo, hydroxylmino or $(C_1-C_6)$alkoxylmino and wherein no more than two substituents are selected from oxo, hydroxylmino or $(C_1-C_6)$alkoxylmino and oxo, hydroxylmino or $(C_1-C_6)$alkoxyimino are on non-aromatic carbon; and wherein said $R_{12}$ rings are optionally additionally mono- or di-substituted independently with $(C_1-C_5)$alkyl or halo;

with the proviso that when $R_6$ is $(C_1-C_5)$alkoxycarbonyl or benzyloxycarbonyl then $R_1$ is 5-halo, 5-$(C_1-C_4)$alkyl or 5-cyano and $R_4$ is (phenyl)(hydroxy)$(C_1-C_4)$alkyl, (phenyl)$((C_1-C_4)$alkoxy)$(C_1-C_4)$alkyl, hydroxymethyl or Ar$(C_1-C_2)$alkyl, wherein Ar is thien-2- or -3-yl, fur-2- or -3-yl or phenyl wherein said Ar is optionally mono- or di-substituted independently with halo; with the provisos that when $R_4$ is benzyl and $R_5$ is methyl, $R_{12}$ is not 4-hydroxy-piperidin-1-yl or when $R_4$ is benzyl and $R_5$ is methyl $R_6$ is not $C(O)N(CH_3)_2$;

with the proviso that when $R_1$ and $R_{10}$ and $R_{11}$ are H, $R_4$ is not imidazol-4-ylmethyl, 2-phenylethyl or 2-hydroxy-2-phenylethyl;

with the proviso that when both $R_8$ and $R_9$ are n-pentyl, none of $R_1$ is 5-chloro, 5-bromo, 5-cyano, 5$(C_1-C_5)$alkyl, 5$(C_1-C_5)$alkoxy or trifluoromethyl;

with the proviso that when $R_{12}$ is 3,4dihydroisoquinol-2-yl, said 3,4-dihydroisoquinol-2-yl is not substituted with carboxy$((C_1-C_4)$alkyl;

with the proviso that when $R_8$ is H and $R_9$ is $(C_1-C_6)$alkyl, $R_9$ is not substituted with carboxy or $(C_1-C_4)$alkoxycarbonyl on the carbon which is attached to the nitrogen atom N of $NHR_9$; and with the proviso that when $R_6$ is carboxy and $R_1$, $R_{10}$, $R_{11}$ and $R_5$ are all H, then $R_4$ is not benzyl, H, (phenyl)(hydroxy)methyl, methyl, ethyl or n-propyl.

A first group of preferred compounds of Formula I consists of those compounds wherein $R_1$ is 5H, 5-halo, 5-methyl, 5-cyano or 5-trifluoromethyl;

$R_{10}$ and $R_{11}$ are each independently H or halo;

A is —C(H)=;

$R_2$ and $R_3$ are H;

$R_4$ is H, methyl, phenyl$(C_1C_2)$alkyl, wherein said phenyl groups are mono- or di-substituted independently with H, halo, $(C_1-C_4)$alkyl, $(C_1C_4)$alkoxy, trifluoromethyl, hydroxy, amino or cyano and wherein said $R_4$ groups are optionally additionally mono-substituted with halo; or $R_4$ is thien-2- or -3-yl$(C_1-C_2)$alkyl, pyrid-2-, -3- or -4-yl $(C_1-C_2)$alkyl, thiazol-2-, -4- or -5-yl$(C_1-C_2)$alkyl, imidazol-2-, -4- or -5-yl$(C_1-C_2)$alkyl, fur-2- or -3-yl $(C_1-C_2)$alkyl, pyrrol-2- or -3-yl$(C_1-C_2)$alkyl, oxazol-2-, -4- or -5-yl$(C_1-C_2)$alkyl, pyrazol-3-, -4- or -5-yl $(C_1-C_2)$alkyl, isoxazol-3- , -4- or -5-yl$(C_1-C_2)$alkyl, isothiazol-3-, -4- or -5-yl($C_1$–$C_2$)alkyl, pyridazin-3- or -4-yl($C_1$–$C_2$)alkyl, pyrimidin-2-, -4-, -5- or -6-yl ($C_1$–$C_2$)alkyl, pyrazin-2-or -3-yl($C_1$–$C_2$)alkyl or 1,3,5-triazin-2-yl($C_1$–$C_2$)alkyl wherein said preceding $R_4$ heterocycles are optionally mono- or di-substituted independently with halo, trifluoromethyl, ($C_1$–$C_4$) alkyl, ($C_1$–$C_4$)alkoxy, amino or hydroxy and said mono- or di-substituents are bonded to cabon;

$R_5$ is H; and $R_6$ is C(O)N$R_8R_9$ or C(O)$R_{12}$.

Within the above first group of preferred compounds of Formula I is a first group of especially preferred compounds wherein $R_4$ is H, phenyl($C_1$–$C_2$)alkyl, thien-2- or -3-yl($C_1$–$C_2$) alkyl, fur-2- or -3-yl($C_1$–$C_2$)alkyl wherein said $R_4$ rings are mono- or di-substituted independently with H or fluoro;

$R_6$ is C(O)$R_{12}$; and $R_{12}$ is morpholino, thiomorpholino, 1-oxothiomorpholino, 1,1-dioxothiomorpholino, thiazolidin-3-yl, 1-oxothiazolidin-3-yl, 1,1-dioxothiazolidin-3-yl, pyrrolidin-1-yl, piperidin-1-yl, piperazin-1-yl, piperazin-4-yl, azetidin-1-yl, 1,2oxazinan-2-yl, isoxazolidin-2-yl, isothiazolidin-2-yl, 1,2-oxazetidin-2-yl, oxazolidin-3-yl, 1,3-dihydroisoindol-2-yl, or azepan-1-yl, wherein said $R_{12}$ rings we optionally mono- or di-substituted independently with halo, ($C_1$–$C_5$)alkyl, ($C_1$–$C_5$)alkoxy, hydroxy, amino, mono-N— or di-N, N—($C_1$–$C_5$)alkylamino, formyl, carboxy, carbamoyl, mono-N— or di-N,N—($C_1$–$C_5$)alkylcarbamoyl, ($C_1$–$C_5$)alkoxycarbonyl, hydroxy($C_1$–$C_5$)alkyl, amino ($C_1$–$C_4$)alkyl, mono-N— or di-N,N—($C_1C_4$) alkylamino($C_1$–$C_4$)alkyl, oxo, hydroxylmino or ($C_1$–$C_6$)alkoxylmino with the proviso that only the $R_{12}$ heterocycles thiazolidin-3-yl, pyrrolidin-1-yl, piperidin-1-yl, piperazin-1-yl, piperazin-4-yl, azetidin-1-yl, 1,2-oxazinan-2-yl, isoxazolidin-2-yl, or oxazolidin-3-yl are optionally mono- or di-substituted with oxo, hydroxylmino, or ($C_1$–$C_6$)alkoxylmino; and wherein said $R_{12}$ rings are optionally additionally mono- or di-substituted independently with ($C_1$–$C_5$)alkyl.

Within the above group of especially preferred compounds are the compounds

5-Chloro-1H-indole-2-carboxylic acid [(1S)-benzyl-2-(3-hydroxylmino-pyrrolidin-1-yl)-2-oxo-ethyl]-amide, 5-Chloro-1H-indole-2-carboxylic acid [2-(cis-3,4-dihydroxy-pyrrolidin-1-yl)-2-oxo-ethyl]-amide, 5-Chloro-1H-indole-2-carboxylic acid [2-((3S,4S)-dihydroxy-pyrrolidin-1-yl)-2-oxo-ethyl]-amide, 5-Chloro-1H-indole-2-carboxylic acid [(1S)-benzyl-2-(cis-3,4-dihydroxy-pyrrolidin-1-yl)-2-oxo-ethyl]-amide, 5-Chloro-1H-indole-2-carboxylic acid [2-(1,1-dioxothiazoildin-3-yl)-2-oxo-ethyl]-amide, 5-Chloro-1H-indole-2-carboxylic acid (2-oxo-2-thiazolidin-3-yl-ethyl)-amide, 5-Chloro-1H-indole-2-carboxylic acid [(1S)-(4-fluorobenzyl)-2-(4-hydroxy-piperidin-1-yl)-2-oxo-ethyl]-amide, 5-Chloro-1H-indole-2-carboxylic acid [(1S)-benzyl-2-((3RS)-hydroxy-piperidin-1-yl)-2-oxo-ethyl]-amide, 5Chloro-1H-indole-2-carboxylic acid [2-oxo-2-((1RS)-oxo-1-thiazolidin-3-yl)-ethyl]-amide, 5-Chloro-1H-indole-2-carboxylic acid [(1S)-(2-fluorobenzyl)-2-(4-hydroxy-piperidin-1-yl)-2-oxo-ethyl]-amide, 5-Chloro-1H-indole-2-carboxylic acid [(1S)-benzyl-2-((3S,4S)-dIhydroxy-pyrrolidin-1-yl)-2-oxo-ethyl]-amide, 5-Chloro-1H-indole-2-carboxylic acid [(1S)-benzyl-2-(3-hydroxy-azetidin-1-yl)-2-oxo-ethyl]-amide, 5-Chloro-1H-indole-2-carboxylic acid [(1S)-benzyl-2-(3-hydroxyimino-azetidin-1-yl)-2-oxo-ethyl]-amide or 5-Chloro-1H-indole-2-carboxylic acid [(1S)-benzyl-2-(4-hydroxyimino-piperidin-1-yl)-2-oxo-ethyl]-amide.

Within the above group of especially preferred compounds is a first group of particularly preferred compounds wherein $R_4$ is H; and $R_{12}$ is thiazolidin-3-yl, 1-oxo-thiazolidin-3-yl, 1,1-dioxothiazolidin-3-yl or oxazolidin-3-yl or said $R_{12}$ substituents optionally mono- or di-substituted independently with carboxy, ($C_1$–$C_5$)alkoxycarbonyl, hydroxy ($C_1$–$C_3$)alkyl, amino($C_1$–$C_3$)alkyl, mono-N— or di-N, N—($C_1$–$C_3$)alkylamino($C_1$–$C_3$)alkyl or $R_{12}$ is mono- or di-substituted pyrrolidin-1-yl wherein said substituents are independently carboxy, ($C_1$–$C_5$) alkoxycarbonyl, ($C_1$–$C_5$)alkoxy, hydroxy, hydroxy ($C_1$–$C_3$)alkyl, amino, amino($C_1$–$C_3$)alkyl, mono-N— or di-N,N—($C_1$–$C_3$)alkylamino($C_1$–$C_3$)alkyl or mono-N— or di-N,N—($C_1$–$C_4$)alkylamino; and the $R_{12}$ rings are optionally additionally independently disubstituted with ($C_1$–$C_5$)alkyl.

Preferred compounds within the immediately preceding group of particularly preferred compounds are compounds wherein a. $R_1$ is 5-chloro;

$R_{10}$ and $R_{11}$ are H; and $R_{12}$ is cis-3,4-dihydroxy-pyrrolidin-1-yl;

b. $R_1$ is 5-chloro;

$R_{10}$ and $R_{11}$ are H; and $R_{12}$ is (3S,4S)-dihydroxy-pyrrolidin-1-yl;

c. $R_1$ is 5-chloro;

$R_{10}$ and $R_{11}$ are H; and $R_{12}$ is 1,1-dioxo-thiazolidin-3-yl;

d. $R_1$ is 5-chloro;

$R_{10}$ and $R_{11}$ are H; and $R_{12}$ is thiazolidin-3-yl; and e. $R_1$ is 5-chloro;

$R_{10}$ and $R_{11}$ are H; and $R_{12}$ is 1-oxo-thiazolidin-3-yl.

Within the above group of especially preferred compounds is a second group of particularly preferred compounds wherein $R_4$ is phenylmethyl, thien-2- or -3-ylmethyl wherein said $R_4$ rings are optionally mono- or di-substituted with fluoro; and $R_{12}$ is thiazolidin-3-yl, 1-oxo-thiazolidin-3-yl, 1,1-dioxothiazolidin-3-yl or oxazolidin-3-yl or said $R_{12}$ substituents optionally mono- or di-substituted independently with carboxy or ($C_1$–$C_5$)alkoxycarbonyl, hydroxy ($C_1$–$C_3$)alkyl, amino($C_1$–$C_3$)alkyl or mono-N— or di-N,N—($C_1$–$C_3$)alkylamino($C_1$–$C_3$)alkyl or $R_{12}$ is mono- or di-substituted azetidin-1-yl or mono- or di-substituted pyrrolidin-1-yl or mono- or di-substituted piperidin-1-yl wherein said substituents are independently carboxy, $(C_1-C_5)$alkoxycarbonyl, hydroxy$(C_1-C_3)$alkyl, amino$(C_1-C_3)$alkyl, mono-N— or di-N,N—$(C_1-C_3)$alkylamino$(C_1-C_3)$alkyl, hydroxy, $(C_1-C_5)$alkoxy, amino, mono-N— or di-N,N—$(C_1-C_5)$ alkylamino, oxo, hydroxylmino or $(C_1-C_5)$ alkoxylmino; and the $R_{12}$ rings are optionally additionally mono- or di-substituted independently with $(C_1-C_5)$alkyl.

Preferred compounds within the immediately preceding group of particularly preferred compounds are compounds wherein a. $R_1$ is 5-chloro;
$R_{10}$ and $R_{11}$ are H;
$R_4$ is 4-fluorobenzyl;
$R_{12}$ is 4-hydroxypiperidin-1-yl; and
the stereochemistry of carbon (a) is (S);

b. $R_1$ is 5-chloro;
$R_{10}$ and $R_{11}$ are H;
$R_4$ is benzyl;
$R_{12}$ is 3-hydroxypiperidin-1-yl; and
the stereochemistry of carbon (a) is (S);

c. $R_1$ is 5-chloro;
$R_{10}$ and $R_{11}$ are H;
$R_4$ is benzyl;
$R_{12}$ is cis-3,4-dihydroxy-pyrrolidin-1-yl; and
the stereochemistry of carbon (a) is S;

d. $R_1$ is 5-chloro;
$R_{10}$ and $R_{11}$ are H; $R_4$ is benzyl;
$R_{12}$ is 3-hydroxyimino-pyrrolidin-1-yl; and
the stereochemistry of carbon (a) is (S);

e. $R_1$ is 5-chloro;
$R_{10}$ and $R_{11}$ are H;
$R_4$ is 2-fluorobenzyl;
$R_{12}$ is 4-hydroxypiperidin-1-yl; and
the stereochemistry of carbon (a) is (S);

f. $R_1$ is 5-chloro;
$R_{10}$ and $R_{11}$ are H;
$R_4$ is benzyl;
$R_{12}$ is (3S,4S)-dihydroxy-pyrrolidin-1-yl; and
the stereochemistry of carbon (a) is (S);

g. $R_1$ is 5-chloro;
$R_{10}$ and $R_{11}$ are H;
$R_4$ is benzyl;
$R_{12}$ is 3-hydroxy-azetidin-1-yl; and
the stereochemistry of carbon (a) is (S);

h. $R_1$ is 5-chloro;
$R_{10}$ and $R_{11}$ are H;
$R_4$ is benzyl;
$R_{12}$ is 3-hydroxyimino-azetidin-1-yl; and
the stereochemistry of carbon (a) is (S); and i. $R_1$ is 5chloro;
$R_{10}$ and $R_{11}$ are H;
$R_4$ is benzyl;
$R_{12}$ is 4-hydroxyimino-piperidin-1-yl; and
the stereochemistry of carbon (a) is (S).

A second group of especially preferred compounds within the first group of preferred compounds are the compounds wherein $R_4$ is H, phenyl$(C_1-C_2)$alkyl, thien-2- or -3-yl$(C_1-C_2)$ alkyl, fur-2- or -3-yl$(C_1-C_2)$alkyl wherein said $R_4$ rings are mono- or di-substituted independently with H or fluoro;

$R_6$ is C(O)NR$_8$R$_9$; and $R_8$ is H, $(C_1-C_5)$alkyl, hydroxy or $(C_1-C_4)$alkoxy; and $R_9$ is H, cyclo$(C_4-C_6)$alkyl, cyclo$(C_3-C_6)$alkyl$(C_1-C_5)$ alkyl, methylene-perfluorinated$(C_1-C_3)$alkyl, pyridyl, pyrrolidinyl, oxazolyl, thiazolyl, imidazolyl, piperidinyl, benzothiazolyl or thiochromanyl; or $R_9$ is $(C_1-C_5)$alkyl wherein said $(C_1-C_5)$alkyl is optionally substituted with cyclo$(C_4-C_6)$alkenyl, phenyl, thienyl, pyridyl, pyrrolidinyl, oxazolyl, thiazolyl, imidazolyl, pyrazolyl, piperidinyl, morpholinyl, thiomorpholinyl, 1-oxothiomorpholinyl, or 1,1-dioxothiomorpholinyl and wherein said $(C_1-C_5)$alkyl or $(C_1-C_4)$alkoxy is optionally additionally independently mono- or di-substituted with halo, hydroxy, $(C_1-C_5)$alkoxy, amino, mono-N— or di-N,N—$(C_1-C_5)$ alkylamino, cyano, carboxy, or $(C_1-C_4)$ alkoxycarbonyl; and wherein the $R_9$ rings are optionally mono- or di-substituted independently on carbon with halo, $(C_1-C_4)$alkyl, $(C_1-C_4)$alkoxy, hydroxy, amino, mono-N— or di-N,N—$(C_1-C_4)$alkylamino, carbamoyl, $(C_1-C_5)$alkoxycarbonyl or carbamoyl.

Within the immediately preceding second group of especially preferred compounds are the compounds wherein a. $R_1$ is 5-chloro;
$R_{10}$ and $R_{11}$ are H;
$R_4$ is benzyl;
$R_8$ is methyl; and
$R_9$ is 3-(dimethylamino)propyl;

b. the stereochemistry of carbon (a) is (S);
$R_1$ is 5-chloro;
$R_{10}$ and $R_{11}$ are H;
$R_4$ is benzyl;
$R_8$ is methyl; and
$R_9$ is 3-pyridyl;

c. the stereochemistry of carbon (a) is (S);
$R_1$ is 5-chloro;
$R_{10}$ and $R_{11}$ are H;
$R_4$ is benzyl;
$R_8$ is methyl; and
$R_9$ is 2-hydroxyethyl; and d. the stereochemistry of carbon (a) is (S);
$R_1$ is 5-fluoro;
$R_{10}$ and $R_{11}$ are H;
$R_4$ is 4-fluorophenylmethyl;
$R_8$ is methyl; and
$R_9$ is 2-morpholinoethyl.

A third group of especially preferred compounds within the first group of preferred compounds are the compounds wherein $R_4$ is H, phenyl$(C_1-C_2)$alkyl, thien-2- or -3-yl$(C_1-C_2)$ alkyl, fur-2- or -3-yl$(C_1-C_2)$alkyl wherein said $R_4$ rings are mono- or di-substituted independently with H or fluoro;

$R_6$ is C(O)NR$_8$R$_9$; and $R_8$ is H, $(C_1-C_5)$alkyl, hydroxy or $(C_1-C_4)$alkoxy; and $R_9$ is $(C_1-C_4)$alkoxy wherein said $(C_1-C_4)$alkoxy is optionally substituted with cyclo$(C_4-C_6)$alkenyl, phenyl, thienyl, pyridyl, pyrrolidinyl, oxazolyl, thiazolyl, imidazolyl, pyrazolyl, piperidinyl, morpholinyl, thiomorpholinyl, 1-oxothiomorpholinyl, or 1,1-dioxothiomorpholinyl and wherein said $(C_1-C_5)$ alkyl or ($C_1$–$C_4$)alkoxy is optionally additionally independently mono- or di-substituted with halo, hydroxy, ($C_1$–$C_5$)alkoxy, amino, mono-N— or di-N,N—($C_1$–$C_5$) alkylamino, cyano, carboxy, or ($C_1$–$C_4$) alkoxycarbonyl; and wherein the $R_9$ rings are optionally mono- or di-substituted independently on carbon with halo, ($C_1$–$C_4$)alkyl, ($C_1$–$C_4$)alkoxy, hydroxy, amino, mono-N— or di-N,N—($C_1$–$C_4$)alkylamino, carbamoyl, ($C_1$–$C_5$)alkoxycarbonyl or carbamoyl.

Within the immediately preceding third group of especially preferred compounds are the compounds wherein a. $R_1$ is 5-chloro;

$R_{10}$ and $R_{11}$ are H;

$R_4$ is benzyl;

$R_8$ is methyl; and $R_9$ is 2-hydroxyethoxy;

b. the stereochemistry of carbon (a) is (S);

$R_1$ is 5-chloro;

$R_{10}$ and $R_{11}$ are H;

$R_4$ is 4-fluorophenylmethyl;

$R_8$ is methyl; and $R_9$ is methoxy;

c. the stereochemistry of carbon (a) is (S);

$R_1$ is 5-chloro;

$R_{10}$ and $R_{11}$ are H;

$R_4$ is benzyl;

$R_8$ is methyl; and $R_9$ is methoxy;

A second group of preferred compounds of Formula I are those compounds wherein $R_1$ is 5-halo, 5-methyl, 5-cyano or trifluoromethyl;

$R_{10}$ and $R_{11}$ are each independently H or halo;

A is —C(H)=;

$R_2$ and $R_3$ are H;

$R_4$ is H, phenyl($C_1$–$C_2$)alkyl, thien-2- or -3-yl($C_1$–$C_2$) alkyl, fur-2- or 3-yl($C_1$–$C_2$)alkyl wherein said rings are mono- or di-substituted Independently with H or fluoro;

$R_5$ is H; and $R_6$ is ($C_1$–$C_5$)alkoxycarbonyl.

A third group of preferred compounds of Formula I are those compounds wherein $R_1$ is 5-halo, 5-methyl, 5-cyano or trifluoromethyl;

$R_{10}$ and $R_{11}$ are each independently H or halo;

A is —C(H)=;

$R_2$ and $R_3$ are H;

$R_4$ is H, methyl or phenyl($C_1$–$C_2$)alkyl, wherein said phenyl groups are mono- or di-substituted independently with H, halo, ($C_1$–$C_4$)alkyl, ($C_1$–$C_4$)alkoxy, trifluoromethyl, hydroxy, amino or cyano and wherein said phenyl groups are additionally mono- or di-substituted independently H or halo; or $R_4$ is thien-2- or -3yl($C_1$–$C_2$)alkyl, pyrid-2-, -3- or -4-yl ($C_1$–$C_2$)alkyl, thiazol-2-, -4- or -5-yl($C_1$–$C_2$)alkyl, imidazol-2-, -4- or -5-yl($C_1$–$C_2$)alkyl, fur-2- or -3-yl ($C_1$–$C_2$)alkyl, pyrrol-2- or -3-yl($C_1$–$C_2$)alkyl, oxazol-2-, -4- or -5-yl($C_1$–$C_2$)alkyl, pyrazol-3-, -4- or -5-yl ($C_1$–$C_2$)alkyl, isoxazol-3-, -4- or -5-yl($C_1$–$C_2$)alkyl, isothiazol-3-, -4- or -5-yl($C_1$–$C_2$)alkyl, pyridazin-3- or -4yl($C_1$–$C_2$)alkyl, pyrimidin-2-, -4-, -5- or -6-yl ($C_1$–$C_2$)alkyl, pyrazin-2- or -3-yl($C_1$–$C_2$)alkyl or 1,3, 5-triazin-2-yl($C_1$–$C_2$)alkyl wherein said preceding $R_4$ heterocycles are optionally mono- or di-substituted independently with halo, trifluoromethyl, ($C_1$–$C_4$) alkyl, ($C_1$–$C_4$)alkoxy, amino or hydroxy and said mono- or di-substituents are bonded to carbon;

$R_5$ is H; and $R_6$ is carboxy.

Within the third group of preferred compounds is a first group of especially preferred compounds wherein $R_{10}$ and $R_{11}$ are H; and $R_4$ is H.

Particularly preferred within the immediately preceding especially preferred group is a compound wherein $R_1$ is 5-chloro.

Another aspect of this invention is directed to intermediates useful for making some of the compounds of Formula I. The intermediates have the Formula QZ Formula QZ

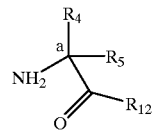

wherein $R_5$ is H;

$R_4$ is H, phenylmethyl, thien-2- or -3-ylmethyl, fur-2- or -3-ylmethyl wherein said rings are optionally mono- or di-substituted with fluoro; and $R_{12}$ is thiazolidin-3-yl, 1-oxothiazolidin-3-yl, 1,1-dioxothiazolidin-3-yl, pyrrolidin-1-yl, piperidin-1-yl, azetidin-1-yl, 1,2-oxazinan-2-yl, isoxazolidin-2-yl, isothiazolidin-2-yl, 1,2-oxazetidin-2-yl or oxazolidinyl, wherein said $R_{12}$ rings are optionally mono- or di-substituted independently with halo, ($C_1$–$C_5$)alkyl, ($C_1$–$C_5$)alkoxy, hydroxy, amino, mono-N— or di-N, N—($C_1$–$C_5$)alkylamino, formyl, carboxy, carbamoyl, mono-N— or di-N,N—($C_1$–$C_5$)alkylcarbamoyl, ($C_1$–$C_5$)alkoxycarbonyl, hydroxy($C_1$–$C_5$)alkyl, amino ($C_1$–$C_4$)alkyl, mono-N— or di-N,N—($C_1$–$C_4$) alkylamino($C_1$–$C_4$)alkyl, oxo, hydroxyimino or ($C_1$–$C_6$)alkoxyimino with the proviso that only the $R_{12}$ heterocycles thiazolidin-3-yl, pyrrolidin-1-yl, piperidin-1-yl, azetidin-1-yl, 1,2-oxazinan-2-yl, isoxazolidin-2-yl, or oxazolidin-3-yl are optionally mono- or di-substituted independently with oxo, hydroxyimino, or ($C_1$–$C_6$)alkoxyimino; and wherein said $R_{12}$ rings are optionally additionally mono- or di-substituted independently with ($C_1$–$C_5$)alkyl and with the proviso that $R_{12}$ is not 2-carboxy-4-hydroxy-pyrrolidin-1-yl, 2-(($C_1$–$C_5$)alkoxycarbonyl)-4-hydroxy-pyrrolidin-1-yl, 2-carboxy-piperidin-1-yl or 2-(($C_1$–$C_5$)alkoxycarbonyl)-piperdin-1-yl.

Particular compounds within the above group of intermediates are the compounds wherein a. $R_4$ is H; and $R_{12}$ is thiazolidin-3-yl;

b. $R_4$ is H; and $R_{12}$ is 1,1-dioxo-thiazolidin-3-yl; and c. $R_4$ is H; and $R_{12}$ is 1-oxo-thiazolidin-3-yl.

A first group of preferred compounds of Formula QZ are those compounds wherein

R$_4$ is phenylmethyl, said phenyl optionally mono- or di-substituted with fluoro; and R$_{12}$ is 3-mono-substituted azetidin-1-yl, 3-mono- or 3,4-disubstituted pyrrolidin-1-yl, 3-, 4-, or 5-mono- or di-substituted piperidin-1-yl, thiazolidin-3-yl, 1-oxothiazolidin-3-yl or 1,1-dioxothiazolidin-3-yl wherein said pyrrolidin-1-yl or piperidin-1-yl are mono- or di-substituted independently with hydroxy, oxo, hydroxyimino, amino, mono-N— or di-N,N—(C$_1$–C$_4$) alkylamino, (C$_1$–C$_5$)alkoxycarbonyl or carboxy and said R$_{12}$ rings are optionally additionally mono- or di-substituted independently with (C$_1$–C$_4$)alkyl.

Particular compounds within the above immediately preceding group of preferred compounds are the compounds wherein a. R$_4$ is benzyl;
R$_{12}$ is 3-hydroxypyrrolidin-3-yl; and
the stereochemistry of carbon (a) is (S);

b. R$_4$ is benzyl;
R$_{12}$ is 3-hydroxyazetidin-1-yl; and
the stereochemistry of carbon (a) is (S);

c. R$_4$ is benzyl;
R$_{12}$ is 3,4-hydroxypyrrolldin-1-yl; and
the stereochemistry of carbon (a) is (S);

d. R$_4$ is benzyl;
R$_{12}$ is 4-hydroxypiperidin-1-yl; and
the stereochemistry of carbon (a) is (S);

e. R$_4$ is 4-fluorophenylmethyl;
R$_{12}$ is 4-hydroxypiperidin-1-yl; and
the stereochemistry of carbon (a) is (S); and f. R$_4$ is benzyl;
R$_{12}$ is 4-hydroxyiminoazetidin-1-yl; and
the stereochemistry of carbon (a) is (S).

Yet another aspect of this invention is directed to a method for treating a glycogen phosphorylase dependent disease or condition in a mammal by administering to a mammal suffering from a glycogen phosphorylase dependent disease or condition a glycogen phosphorylase dependent disease or condition treating amount of a Formula I compound.

Yet another aspect of this invention is directed to a method for treating hyperglycemia in a mammal by administering to a mammal suffering from hyperglycemia a hyperglycemia treating amount of a Formula I compound.

Yet another aspect of this invention is directed to a method for treating diabetes in a mammal by administering to a mammal suffering from diabetes a diabetes treating amount of a Formula I compound. Included in the treatment of diabetes is the prevention or attenuation of long term complications such as neuropathy, nephropathy, retinopathy or cataracts.

Yet another aspect of this invention is directed to a method for treating hypercholesterolemia in a mammal by administering to a mammal suffering from hypercholesterolemia a hypercholesterolemia treating amount of a Formula I compound.

Yet another aspect of this invention is directed to a method for treating atherosclerosis in a mammal by administering to a mammal suffering from atherosclerosis an atherosclerosis treating amount of a Formula I compound.

Yet another aspect of this Invention is directed to a method for treating hyperinsulinemia in a mammal by administering to a mammal suffering from hyperinsulinemia a hyperinsulinemia treating amount of a Formula I compound.

Yet another aspect of this invention is directed to a method for treating hypertension In a mammal by administering to a mammal suffering from hypertension a hypertension treating amount of a Formula I compound.

Yet another aspect of this invention is directed to a method for treating hyperlipidemia in a mammal by administering to a mammal suffering from hyperlipidemia a hyperlipidemia treating amount of a Formula I compound.

Yet another aspect of this invention is directed to a method for preventing a myocardial ischemic injury in a mammal by administering to a mammal at risk for perioperative myocardial ischemic injury a perioperative myocardial ischemic injury preventing amount of a Formula I compound.

Yet another aspect of this invention is directed to a method for preventing a myocardial ischemic injury in a mammal by administering to a mammal at risk for perioperative myocardial ischemic injury a perioperative myocardial ischemic injury preventing amount of a glycogen phosphorylase inhibitor.

This invention is also directed to pharmaceutical compositions which comprise a therapeutically effective amount of a compound of Formula I and a pharmaceutically acceptable carrier.

Preferred compositions include pharmaceutical compositions for the treatment of glycogen phosphorylase dependent diseases or conditions in mammals which comprise a glycogen phosphorylase dependent disease or condition treating amount of a compound of Formula I and a pharmaceutically acceptable carrier.

Another aspect of this invention is directed to pharmaceutical compositions for the treatment of diabetes which comprise a therapeutically effective amount of a glycogen phosphorylase inhibitor;

one or more antidiabetic agents such as insulin and insulin analogs (e.g. LysPro insulin); GLP-1 (7–37) (insulinotropin) and GLP-1 (7–36)-NH$_2$; Sulfonylureas and Analogs: chlorpropamide, glibenclamide, tolbutamide, tolazamide, acetohexamide, glypizide®, glimepiride, repaglinide, meglitinide; Biguanides: metformin, phenformin, buformin; α2-Antagonists and Imidazolines: midaglizole, isaglidole, deriglidole, idazoxan, efaroxan, fluparoxan; Other insulin secretagogues: linogliride, A-4166; Glitazones: ciglitazone, pioglitazone, englitazone, troglitazone, darglitazone, BRL49653; Fatty Acid Oxidation Inhibitors: clomoxir, etomoxir; α-Glucosidase inhibitors: acarbose, miglitol, emiglitate, voglibose, MDL-25,637, camiglibose, MDL-73,945; β-Agonists: BRL 35135, BRL 37344, Ro 16-8714, ICI D7114, CL 316,243; Phosphodiesterase Inhibitors: L-386,398; Lipid-lowering Agents: benfluorex; Antiobesity Agents: fenfluramine; Vanadate and vanadium complexes (e.g. naglivan®) and peroxovanadium complexes; Amylin Antagonists; Glucagon Antagonists; Gluconeogenesis Inhibitors; Somatostatin Analogs; Antilipolytic Agents: nicotinic acid, acipimox, WAG 994; and optionally a pharmaceutically acceptable carrier.

Preferred pharmaceutical compositions within the immediately preceding group are those compositions wherein the glycogen phosphorylase inhibitor is a compound of Formula I.

Another aspect of this invention is a method of treating diabetes in a mammal with the above described combination compositions.

Glycogen phosphorylase dependent diseases or conditions refers to disorders which are mediated, initiated or maintained, in whole or in part, by the cleavage of the glycogen macromolecule by glycogen phosphorylase enzymes to release glucose-1 -phosphate and a new shortened glycogen molecule. These disorders are ameliorated by reduction of or characterized by an elevation of glycogen phosphorylase activity. Examples include diabetes, hyperglycemia, hypercholesterolemia, hypertension, hyperinsulinemia, hyperlipidemia, atherosclerosis and myocardial ischemia.

The term glycogen phosphorylase inhibitor refers to any substance or agent or any combination of substances and/or agents which reduces, retards, or eliminates the enzymatic action of glycogen phosphorylase. The currently known enzymatic action of glycogen phosphorylase is the degradation of glycogen by catalysis of the reversible reaction of a glycogen macromolecule and inorganic phosphate to glucose-1-phosphate and a glycogen macromolecule which is one glucosyl residue shorter than the original glycogen macromolecule (forward direction of glycogenolysis).

The term "treating" as used herein includes preventative (e.g., prophylactic) and palliative treatment.

By halo is meant chloro, bromo, iodo, or fluoro.

By alkyl is meant straight chain or branched saturated hydrocarbon. Exemplary of such alkyl groups (assuming the designated length encompasses the particular example) are methyl, ethyl, propyl, isopropyl, butyl, sec-butyl, tertiary butyl, pentyl, isopentyl, hexyl and isohexyl.

By alkoxy is meant straight chain or branched saturated alkyl bonded through an oxy. Exemplary of such alkoxy groups (assuming the designated length encompasses the particular example) are methoxy, ethoxy, propoxy, isopropoxy, butoxy, isobutoxy, tertiary butoxy, pentoxy, isopentoxy, hexoxy and isohexoxy.

The expression "pharmaceutically-acceptable anionic salt" refers to nontoxic anionic salts containing anions such as (but not limited to) chloride, bromide, iodide, sulfate, bisulfate, phosphate, acetate, maleate, fumarate, oxalate, lactate, tartrate, citrate, gluconate, methanesulfonate and 4-toluene-sulfonate.

The expression "pharmaceutically-acceptable cationic salts" refers to nontoxic cationic salts such as (but not limited to) sodium, potassium, calcium, magnesium, ammonium or protonated benzathine (N,N'-dibenzylethylenediamine), choline, ethanolamine, diethanolamine, ethylenediamine, meglamine (N-methylglucamine), benethamine (N-benzylphenethylamine), piperazine or tromethamine (2-amino-2-hydroxymethyl-1,3-propanediol).

The expression "prodrug" refers to compounds that are drug precursors, which following administration, release the drug in vivo via some chemical or physiological process (e.g., a prodrug on being brought to the physiological pH is converted to the desired drug form). Certain exemplary prodrugs upon cleavage release the corresponding free acid, and such hydrolyzable ester-forming residues of the compounds of this invention include but are not limited to carboxylic acid substituents (e.g., $R_6$ is carboxy, or $R_8$, $R_9$ or $R_{12}$ contains carboxy) wherein the free hydrogen is replaced by $(C_1-C_4)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3phthalidyl, 4-crotonolactonyl, gamma-butyrolacton-4-yl, di-N,N-$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-$(C_1-C_2)$alkyl and piperidino-, pyrrolidino- or morpholino$(C_2-C_3)$alkyl.

Other exemplary prodrugs release an alcohol of Formula I wherein the free hydrogen of the hydroxy substituent (e.g., $R_8$, $R_9$ or $R_{12}$ contains hydroxy) is replaced by $(C_1-C_6)$alkanoyloxymethyl, 1-$((C_1-C_6)$alkanoyloxy)ethyl, 1-methyl-1-$((C_1-C_6)$alkanoyloxy)ethyl, $(C_1-C_6)$alkoxycarbonyloxymethyl, N-$(C_1-C_6)$alkoxycarbonylaminomethyl, succinoyl, $(C_1-C_6)$alkanoyl, α-amino$(C_1-C_4)$alkanoyl, arylacyl and α-aminoacyl, or α-aminoacyl-α-aminoacyl wherein said α-aminoacyl moieties are independently any of the naturally occurring L-amino acids found in proteins, $P(O)(OH)_2$, —$P(O)(O(C_1-C_6)$alkyl$)_2$ or glycosyl (the radical resulting from detachment of the hydroxyl of the hemiacetal of a carbohydrate).

Other exemplary prodrugs include but are not limited to derivatives of Formula I wherein $R_2$ is a free hydrogen which is replaced by R-carbonyl, RO-carbonyl, NRR'-carbonyl where R and R' are each independently $(C_1-C_{10})$alkyl, $(C_3-C_7)$cycloalkyl, benzyl, or R-carbonyl is a natural α-aminoacyl or natural α-aminoacyl-natural α-aminoacyl, —$C(OH)C(O)OY$ wherein (Y is H, $(C_1-C_6)$alkyl or benzyl), —$C(OY_0)Y_1$ wherein $Y_0$ is $(C_1-C_4)$ alkyl and $Y_1$ is $((C_1-C_6)$alkyl, carboxy$(C_1-C_6)$alkyl, amino$(C_1-C_4)$alkyl or mono-N— or di-N,N—$(C_1-C_4)$alkylaminoalkyl, —$C(Y_2)Y_3$ wherein $Y_2$ is H or methyl and $Y_3$ is mono-N— or di-N,N—$(C_1-C_6)$alkylamino, morpholino, piperidin-1-yl or pyrrolidin-1-yl.

Other exemplary prodrugs include but are not limited to derivatives of Formula I bearing a hydrolyzable moiety at $R_3$, which release a compound of formula I wherein $R_3$ is a free hydrogen on hydrolysis. Such hydrolyzable moieties at $R_3$ are/include 1-hydroxy$(C_1-C_6)$alkyl or 1-hydroxy-1-phenylmethyl.

Other exemplary prodrugs include cyclic structures such as compounds of Formula I wherein $R_2$ and $R_3$ are a common carbon, thus forming a five-membered ring. The linking carbon may be mono- or di-substituted independently with H, $(C_1-C_6)$alkyl, $(C_3-C_6)$cycloalkyl or phenyl.

As used herein, the expressions "reaction-inert solvent" and "inert solvent" refers to a solvent which does not interact with starting materials, reagents, intermediates or products in a manner which adversely affects the yield of the desired product.

The chemist of ordinary skill will recognize that certain compounds of this invention will contain one or more atoms which may be in a particular stereochemical or geometric configuration, giving rise to stereoisomers and configurational isomers. All such isomers and mixtures thereof are included in this invention. Hydrates of the compounds of this invention are also included as an aspect of this invention.

The chemist of ordinary skill will recognize that certain combinations of heteroatom-containing substituents listed in this invention define compounds which will be less stable under physiological conditions (e.g. those containing acetal or aminal linkages). Accordingly, such compounds are less preferred.

The term "$R_x$ ring" wherein x is an integer, for example, "$R_9$ ring", "$R_{12}$ ring" or "$R_4$ ring" as used herein in reference to substitution on the ring refers to moieties wherein the ring is $R_x$ and also wherein the ring is contained within $R_x$.

As used herein the term mono-N— or di-N,N—$(C_1-C_x)$ alkyl . . . refers to the $(C_1-C_x)$alkyl moiety taken independently when it is di-N,N—$(C_1-C_x)$alkyl . . . (x refers to integers).

Other features and advantages will be apparent from the specification and claims which describe the invention.

DETAILED DESCRIPTION OF THE INVENTION

In general the compounds of Formula I can be made by processes which include processes known in the chemical arts, particularly in light of the description contained herein. Certain processes for the manufacture of Formula I compounds are provided as further features of the invention and are illustrated by the following reaction schemes.

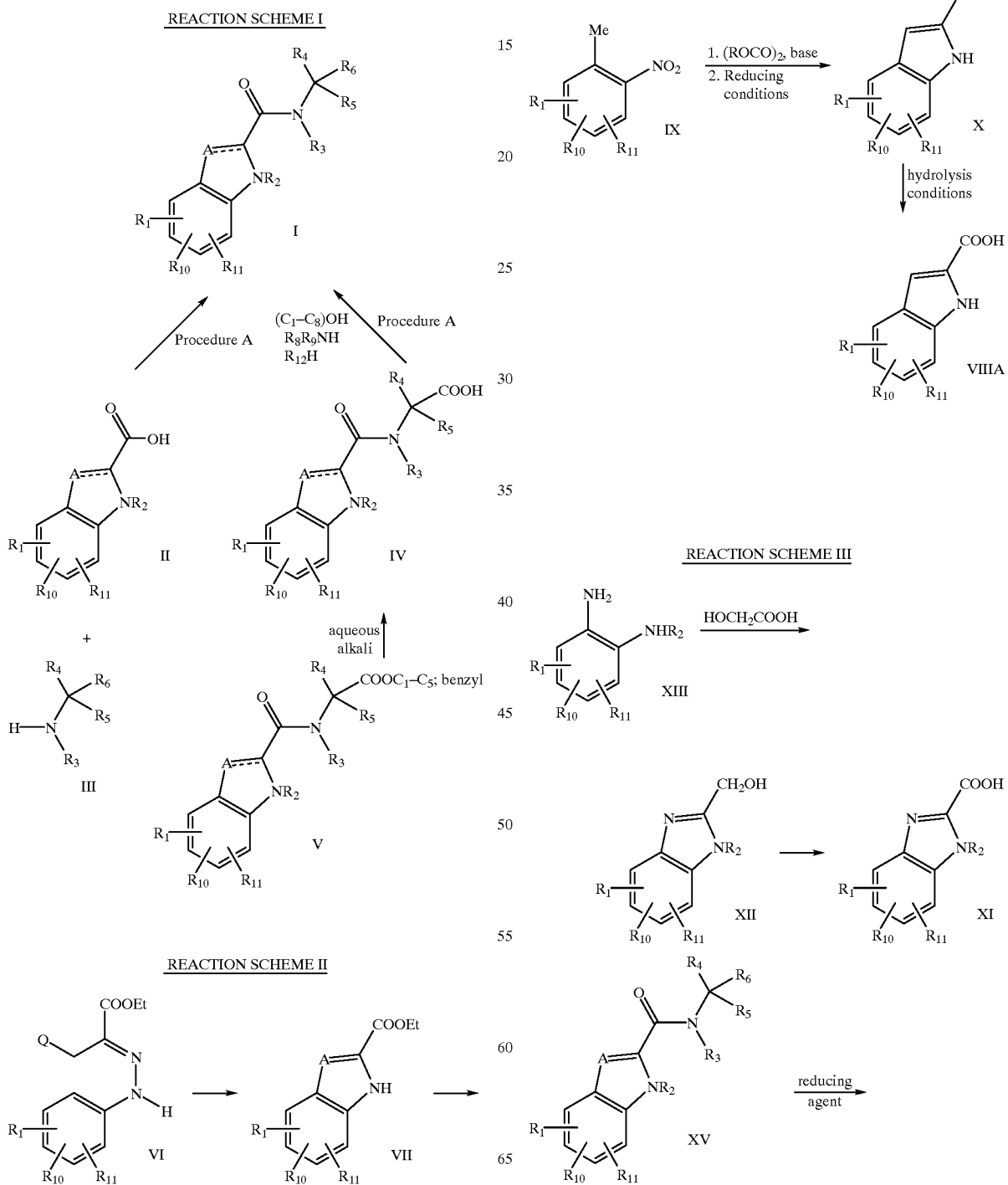

REACTION SCHEME V

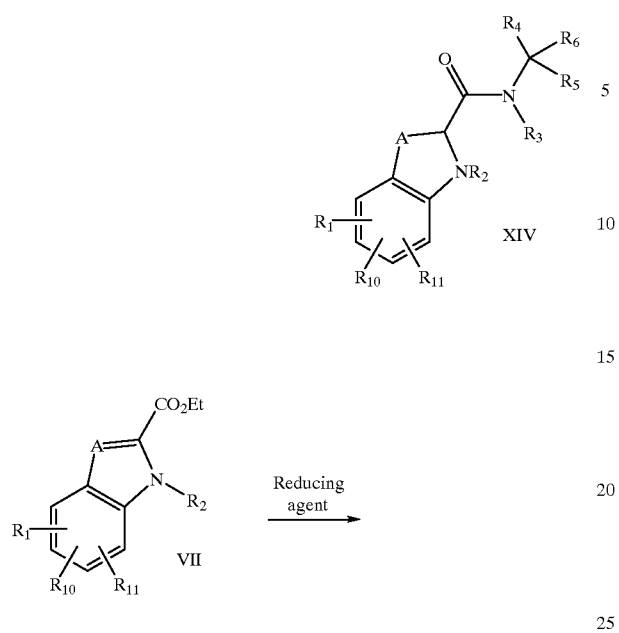

REACTION SCHEME VI

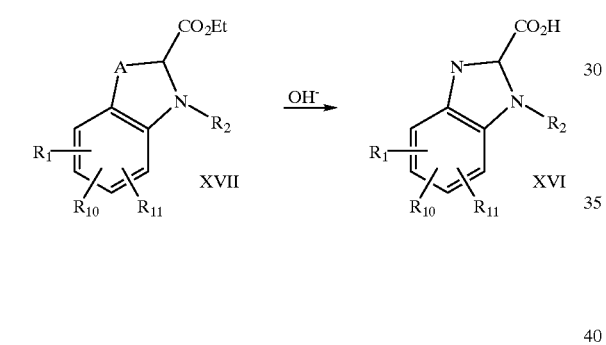

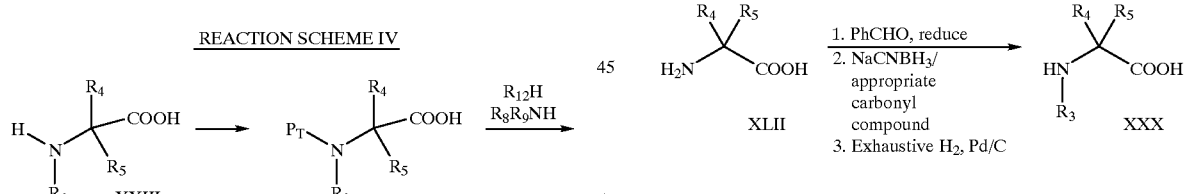

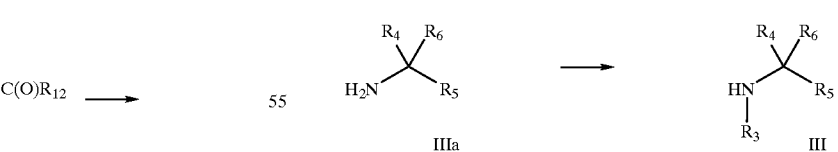

REACTION SCHEME IV

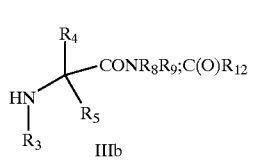

According to Reaction Scheme I the Formula I compounds, wherein $R_1$, $R_{10}$, $R_{11}$, A, $R_2$, $R_3$, $R_4$, $R_5$ and $R_6$ are as defined above may be prepared by either of two general processes. In the first process the desired Formula I compound may be prepared by coupling the appropriate Formula II indole-2-carboxylic acid, indoline-2-carboxylic acid or benzimidazole-2-carboxylic acid with the appropriate Formula III amine (i.e., acylating the amine). In the second process the desired Formula I compound may be prepared by coupling the appropriate Formula IV compound (i.e., a Formula I compound wherein $R_6$ is carboxy) with the appropriate alcohol or formula $R_8R_9NH$ or $R_{12}H$ amine, wherein $R_8$, $R_9$ and $R_{12}$ are as defined above (i.e., acylating the amine or alcohol). The first process (coupling Formula II compounds with Formula III compounds is typically preferred when $R_4$ is not H and $R_5$ is H.

Typically, the Formula II compound is combined with the Formula III compound (or Formula IV compound is combined with the appropriate amine (e.g., $R_{12}H$ or $R_8R_9NH$)) or alcohol in the presence of a suitable coupling agent. A suitable coupling agent is one which transforms a carboxylic acid into a reactive species which forms an amide or ester linkage on reaction with an amine or alcohol, respectively.

The coupling agent may be a reagent which effects this condensation in a one pot process when mixed together with the carboxylic acid and amine or alcohol. If the acid is to be condensed with an alcohol it is preferable to employ a large excess of the alcohol as the reaction solvent, with or without 1.0 to 1.5 equivalent added dimethylaminopyridine. Exemplary coupling reagents are 1-(3-dimethylaminopropyl)-3-ethylcarbodiimide hydrochloride-hydroxybenzotriazole (DEC/HBT), carbonyldiimidazole, dicyclohexylcarbodiimide/hydroxybenzotriazole (HBT), 2-ethoxy-1-ethoxycarbonyl-1,2-dihydroquinoline (EEDQ), carbonyldiimidazole/HBT, propanephosphonic anhydride (propanphosphonic acid anhydride, PPA) and diethylphosphorylcyanide. The coupling is performed in an inert solvent, preferably an aprotic solvent at a temperature of about $-20°$ C. to about $50°$ C. for about 1 to about 48 hours, in the optional presence of a tertiary amine base such as triethylamine. Exemplary solvents include acetonitrile, dichloromethane, ethyl acetate, dimethylformamide and chloroform or mixtures thereof. An example of a suitable coupling procedure is Procedure A, contained herein (just prior to the EXAMPLES).

The coupling agent may also be that agent which converts the carboxylic acid to an activated intermediate which is isolated and/or formed in a first step and allowed to react with the amine or alcohol in a second step. Examples of such coupling agents and activated intermediates are thionyl chloride or oxalyl chloride to form the acid chloride, cyanuric fluoride to form an acid fluoride or an alkyl chloroformate such as isobutyl or isopropenyl chloroformate (with a tertiary amine base) to form a mixed anhydride of the carboxylic acid. If the coupling agent is oxalyl chloride it is advantageous to employ a small amount of dimethylformamide as cosolvent with another solvent (such as dichloromethane) to catalyze the formation of the acid chloride. This acid chloride may be coupled by mixing with the Formula III intermediate in an appropriate solvent together with an appropriate base. Appropriate solvent/base combinations are for example, dichloromethane, dimethylformamide or acetonitrile or mixtures thereof in the presence of a tertiary amine base e.g., triethylamine. Other appropriate solvent/base combinations include water or a $(C_1-C_5)$ alcohol or a mixture thereof together with a cosolvent such as dichloromethane, tetrahydrofuran or dioxane and a base such as sodium or potassium carbonate, sodium potassium of lithium hydroxide or sodium bicarbonate in sufficient quantity to consume the acid liberated in the reaction. Use of a phase transfer catalyst (typically 1 to 10 mole %) such as a quaternary ammonium halide (e.g. tetrabutylammonium bromide or methyl trioctylammonium chloride) is advantageous when a mixture of only partially miscible cosolvents is employed (e.g dichloromethane-water or dichloromethane-methanol). Use of these coupling agents and appropriate selection of solvents and temperatures are known to those skilled in the art or can be readily determined from the literature. These and other exemplary conditions useful for coupling carboxylic acids are described in Houben-Weyl, Vol XV, part II E. Wunsch, Ed., G. Theime Verlag, 1974, Stuttgart, and M. Bodansky, Principles of Peptide Synthesis, Springer-Verlag Berlin 1984, and The Peptides. Analysis, Synthesis and Biology (ed. E. Gross and J. Meienhofer), vols 1–5 (Academic Press NY 1979–1983).

The Formula IV compounds wherein $R_1$, $R_{10}$, $R_{11}$, A, $R_2$, $R_3$, $R_4$ and $R_5$ are as defined above may be prepared from the corresponding Formula V ester (i.e., Formula I compounds wherein $R_6$ is $(C_1-C_5)$alkoxycarbonyl or benzyloxycarbonyl) by hydrolysis with aqueous alkali at a temperature of about $-20°$ C. to about $100°$ C., typically at about $20°$ C., for about 30 minutes to about 24 hours.

Alternatively, Formula IV compounds are prepared by activation of a Formula II indole carboxylic acid with a coupling agent (as described above) which gives an activated intermediate (such as an acid chloride, acid fluoride, or mixed anhydride) which is then allowed to react with a compound of Formula III wherein $R_3$, $R_4$ and $R_5$, are as described above and $R_6$ is carboxy, in a suitable solvent in the presence of a suitable base. Suitable solvents include water, or methanol or a mixture thereof, together with a cosolvent such as dichloromethane, tetrahydrofuran, or dioxane. Suitable bases include sodium, potassium or lithium hydroxides, sodium or potassium bicarbonate, sodium or potassium carbonate, or potassium carbonate together with tetrabutyl ammonium bromide (1 equivalent) in sufficient quantity to consume the acid liberated in the reaction (generally that quantity sufficient to maintain the pH of the reaction at greater than 8). The base may be added incrementally together with the activated intermediate to effect proper pH control of the reaction. The reaction is conducted generally between $-20°$ C. and $50°$ C. Isolation procedures are tailored by one skilled in the art to remove impurities, but typically consist of removal of water-miscible cosolvents by evaporation, extraction of impurities at high pH with an organic solvent, acidification to low pH (1–2) and filtration, or extraction of the desired product with a suitable solvent such as ethyl acetate or dichloromethane.

The Formula V compound may be prepared by coupling the appropriate Formula III compound wherein $R_6$ is alkoxycarbonyl and the appropriate Formula II compound in an analogous procedure to that described above (e.g., Procedure A).

Alternatively, Formula I compounds which contain sulfur atoms in the sulfoxide or sulfone oxidation state may be prepared from the corresponding Formula I compounds having the sulfur atom in the unoxidized form, by treatment with a suitable oxidizing agent, such as m-chloroperoxybenzoic acid in dichloromethane at a temperature of about $0°$ C. to about $25°$ C. for about 1 to about 48 hours using about 1 to about 1.3 equivalent for conversion to the sulfoxide oxidation state and greater than about 2 equivalents for conversion to the sulfone oxidation state.

Some of the preparation methods described herein may require protection of remote functionality (i.e., primary amine, secondary amine, carboxyl in Formula I precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene, *Protective Groups in Organic Synthesis,* John Wiley & Sons, New York, 1991.

For example, in Reaction Scheme I certain Formula I compounds contain primary amine, secondary amine or carboxylic acid functionality in the part of the molecule defined by $R_6$ which may interfere with the intended coupling reaction of Reaction Scheme I, if the Formula III intermediate or $R_{12}H$ or $R_8R_9NH$ amine is left unprotected. Accordingly, the primary amine, secondary amine or carboxylic acid functionality may be protected, where it is present in the $R_6$ moieties of the Formula III intermediate $R_8R_9NH$ or $R_{12}H$ amine by an appropriate protecting group during the coupling reaction of Reaction Scheme I. The product of such coupling reaction in such a case is a Formula I compound containing the protecting group. This protecting group is removed in a subsequent step to provide the Formula I compound. Suitable protecting groups for amine and carboxylic acid protection include those protecting groups commonly used in peptide synthesis (such as N-t-butoxycarbonyl, N-carbobenzyloxy, and 9-fluorenylmethylenoxycarbonyl for amines and lower alkyl or benzyl esters for carboxylic acids) which are not chemically reactive under the coupling conditions described above (and immediately preceding the Examples herein as Procedure A) and can be removed without chemically altering other functionality in the Formula I compound.

The starting indole-2-carboxylic acids and indoline-2-carboxylic acids used in Reaction Scheme I, when not commercially available or known in the prior art (such art is extensively published), are available by conventional synthetic methods. For example, according to Reaction Scheme II the Formula VII indole ester (wherein A is not nitrogen) may be prepared from the Formula VI compound (wherein Q is selected to achieve the desired A as defined above, except for N) via a Fischer indole synthesis (see *The Fischer Indole Synthesis* Robinson, B. (Wiley, New York, 1982)) followed by saponification of the resulting Formula VII indole ester to yield the corresponding Formula VIII acid. The starting aryl hydrazone may be prepared by condensation of a readily available hydrazine with the appropriate carbonyl derivative or via the Japp-Klingeman reaction (see *Organic Reactions,* Phillips, R. R., 1959, 10, 143).

Alternatively, the Formula VIIIA indole 2-carboxylic acid may be prepared by condensation of a Formula IX ortho methyl nitro compound with an oxalate ester to yield the Formula X indole ester followed by reduction of the nitro group and subsequent hydrolysis.

This three step process is known as the Reissert indole synthesis (Reissert, Chemische Berichte 1897, 30, 1030). Conditions for accomplishing this sequence, and references thereto, are described in the literature (Kermack, et al., J. Chem. Soc. 1921, 119, 1602; Cannon et al., J. Med. Chem. 1981, 24, 238; Julian, et al in Heterocyclic Compounds, vol 3 (Wiley, New York, N.Y., 1962, R. C. Elderfield, ed.) p 18). An example of the specific implementation of this sequence is Examples 10A–10C herein.

3Halo-5-chloro-1H-indole-2-carboxylic acids may also be prepared by halogenation of 5-chloro-1H-indole-2-carboxylic acids.

According to Reaction Scheme III the Formula XI benzimidazole-2carboxylic acid intermediates may be prepared by condensation of a Formula XIII ortho-diamino compound with glycolic acid, followed by oxidation of the resulting Formula XII benzimidazole-2-methanol (Bistrzycki, A. and Przeworski, G. Ber. 1912, 45, 3483).

Alternatively, (to Reaction Scheme II) the Formula XIV substituted indolines may be prepared by reduction of the corresponding Formula XV indoles with a reducing agent such as magnesium in methanol at a temperature of about 25° C. to about 65° C. for about 1 to about 48 hours (Reaction Scheme III).

Formula XVI indoline carboxylic acids are prepared by saponification of the corresponding Formula XVII ester (Reaction Scheme III). The Formula XVII ester is prepared by reduction of the corresponding Formula VII indole ester with a reducing agent such as magnesium in methanol as described for the conversion of the Formula XV compound to the Formula XIV compound above.

The following paragraphs describe ways to prepare the various amines which are used in the above Reaction Schemes.

According to Reaction Scheme IV a Formula XXIII alpha-amino acid may be protected on nitrogen with an appropriate protecting group ($P_t$) (e.g., t-Boc) to form a Formula XXIV compound. One skilled in the art can readily select an appropriate protecting group and a method for its introduction. For example, two common protecting groups are t-Boc (introduced by treating the amino acid with di-t-butyldicarbonate in a preferably protic suitable solvent or solvent mixture at high pH) and CBZ (introduced by treating the amino acid with benzylchloroformate in a suitable, preferably protic solvent or solvent mixture and base). The Formula XXIV compound is coupled (in an analogous procedure to the coupling process described in Reaction Scheme I) with an appropriate $R_8R_9NH$ or $HR_{12}$ amine to form a Formula XXV compound, which is then deprotected resulting in the Formula IIIb compound (i.e., Formula III compound wherein $R_6$ is $C(O)R_{12}$ or $C(O)NR_8R_9$). If the protecting group is t-Boc by treatment of the Formula XXV compound with an acid in a suitable, preferably aprotic, solvent. Acids for this deprotection include HCl, $MeSO_3H$ or trifluoroacetic acid.

According to Reaction Scheme V a Formula XXXI compound (N-protected Formula III amine where $R_6$ is $(C_1-C_8)$ alkoxycarbonyl or benzyloxycarbonyl) may be prepared from the corresponding Formula XXX unprotected amino acid via N-protection (yielding a Formula XXXIII protected amino acid) followed by esterification. For example, the Formula XXXIII compound may be esterified with the appropriate alcohol and an acid catalyst such as hydrogen chloride or thionyl chloride, or in the case of tert-butanol by treatment of the amino acid with isobutylene and an acid catalyst such as concentrated sulfuric acid or by treatment with an alkyl halide (e.g., methyl iodide) and base (e.g., potassium carbonate). Alternatively, the esterification may precede the protection step.

According to Reaction Scheme VI the Formula XXX compounds wherein $R_3$ is not H utilized in Reaction Scheme V may be prepared as follows. The Formula XLI amino acids may be prepared by N-alkylation of the Formula XL protected ($P_T$) amino acids by treatment with an appropriate base and alkylating agent. Specific procedures for this alkylation are described by Benoiton, Can. J. Chem 1977, 55, 906–910, and Hansen, J. Org. Chem. 1985, 50 945–950. For example, when $R_3$ is methyl, and $P_T$ is Boc, sodium hydride and methyl iodide in tetrahydrofuran are utilized. Deprotection of the Formula XLI compound yields the desired Formula XXX compound.

Alternatively, a Formula XLI amino acid may be N-alkylated by a three-step sequence involving reductive benzylation (such as with benzaldehyde, Pd/C-catalyzed hydrogenation) to give the mono-N-benzyl derivative and reductive amination with the appropriate carbonyl compound (for example with formaldehyde and sodium cyanoborohydride to introduce $R_3$ as methyl) to give the N-Benzyl, N-$R_3$-substituted amino acid. The N-benzyl protecting group is conveniently removed (for example by hydrogenation with an appropriate catalyst) to yield the Formula XXX compound. Specific conditions for this three step alkylation procedure are described by Reinhold et al., J. Med. Chem., 1968, 11, 258–260.

The immediately preceding preparation may also be used to introduce an $R_3$ moiety into a Formula IIIa Intermediate (which is a Formula III intermediate wherein $R_3$ is H).

The amino acids used in the schemes herein (e.g., XL, XLII), if not commercially available, or reported in the literature, may be prepared by a variety of methods known to those skilled in the art. For example, the Strecker synthesis or variations thereof may be used. Accordingly, an aldehyde ($R_4$CHO), sodium or potassium cyanide and ammonium chloride react to form the corresponding aminonitrile. The aminonitrile is hydrolyzed with mineral acid to form the desired Formula XLII $R_4$C(NH$_2$)COOH amino acid. Alternatively, the Bucherer-Berg method may be used wherein a hydantoin is formed by heating an aldehyde ($R_4$CHO) with ammonium carbonate and potassium cyanide followed by hydrolysis (for example, with barium hydroxide in refluxing dioxane) with acid or base to form the desired Formula XLII $R_4$C(NH$_2$)COOH amino acid.

Other methods for synthesis of α-amino acids are also reported in the literature which would permit one skilled in the art to prepare the desired Formula XLII $R_4$C(NH$_2$)COOH intermediate necessary for the synthesis of Formula I compounds.

Suitable methods for the synthesis and/or resolution of Formula XLII compounds are found in reviews by Duthaler (Tetrahedron 1994, 50, 1539–1650), or by Williams (R. M. Williams, Synthesis of optically active amino acids. Pergamon: Oxford, U.K., 1989).

A specific method for the synthesis of a Formula XLII intermediate in either enantiomeric form from the corresponding $R_4$X (X=Cl, Br, or I) intermediate is the procedure of Pirrung and Krishnamurthy (J. Org. Chem. 1993, 58, 957–958), or by the procedure of O'Donnell, et al. (J. Am. Chem. Soc. 1989, 111, 2353–2355). The required $R_4$X intermediates are readily prepared by many methods familiar to the chemist skilled In the art. For example, those compounds when $R_4$X is ArCH$_2$X may be prepared by radical halogenation of the compound ArCH$_3$ or by formylation of the arene Ar—H and conversion of the alcohol to the bromide.

Another specific method for the synthesis of Formula XLII intermediates in either enantiomeric form is that of Corey and Link (J. Am. Chem. Soc. 1992, 114, 1906–1908). Thus, an intermediate of formula $R_4$COCCl$_3$ is reduced enantiospecifically to intermediate $R_4$CH(OH)CCl$_3$, which is converted on treatment with azide and base to an Intermediate $R_4$CH(N$_3$)COOH, which is reduced by catalytic hydrogenation to the desired Formula XLII compound. The requisite trichloromethyl ketone $R_4$COCCl$_3$ is obtained by reaction of the aldehyde $R_4$CHO with trichloromethide anion followed by oxidation (Gallina and Giordano, Synthesis 1989, 466–468).

A compound of the formula $R_8$NH$_2$ or $R_9$NH$_2$ is monoalkylated with a carbonyl compound corresponding to $R_8$ or $R_9$, respectively, under appropriate reductive amination conditions, to give a formula $R_8R_9$NH amine. To avoid dialkylation, it may be preferable to protect the amines ($R_8$NH$_2$ or $R_9$NH$_2$) with a suitable protecting group $P_T$ to give $R_8(P_T)$NH or $R_9(P_T)$NH, for example by reaction with benzaldehyde and a reducing agent. The protected amines are monoalkylated with a carbonyl compound corresponding to $R_9$ or $R_8$ respectively, under suitable reductive amination conditions, to give $R_8R_9$N($P_T$). The protecting group ($P_T$) is removed (e.g. by exhaustive catalytic hydrogenation when $P_T$ is benzyl) to give a compound of formula $R_8R_9$NH. Appropriate reductive amination conditions are available from the literature to one skilled in the art. These conditions include those reported by Borch et al. (J. Am. Chem. Soc. 1971, 2897–2904) and those reviewed by Emerson (Organic Reactions, Wiley: New York, 1948 (14), 174), Hutchins et al. (Org. Prep. Proced. Int 1979 (11), 20, and Lane et al. (Synthesis 1975, 135). Reductive amination conditions favoring N-monoalkylation include those reported by Morales, et al. (Synthetic Communications 1984, 1213–1220) and Verardo et al. (Synthesis 1992 121–125). The $R_8$NH$_2$ or $R_9$NH$_2$ amines may also be monoalkylated with $R_9$X or $R_8$X, respectively, where X is chloride, bromide, tosylate or mesylate. Alternatively, an intermediate of formula $R_8(P_T)$NH or $R_9(P_T)$NH may be alkylated with $R_9$X or $R_8$X, and the protecting group removed to give a compound of formula $R_8R_9$NH.

Additional methods may be used to prepare formula $R_8R_8$NH amines wherein $R_8$—NH or $R_9$—NH are oxygen-nitrogen linked. Thus a readily available compound of formula (C$_1$–C$_4$)alkoxycarbonyl-NHOH or NH$_2$CONHOH is dialkylated on nitrogen and oxygen by treatment with base and excess suitable alkylating agent (R—X) to give the corresponding (C$_1$–C$_4$)alkoxycarbonyl-N(R)OR which is then hydrolyzed to give a compound of formula $R_8R_9$NH (wherein $R_8$=$R_9$=R). Suitable conditions, base, and alkylating agent include those described by Goel and Krolls (Org. Prep. Proced. Int. 1987, 19, 75–78) and Major and Fleck (J. Am. Chem. Soc. 1928, 50, 1479). Alternatively, N-hydroxyurea (NH$_2$CONH(OH)) may be sequentially alkylated, first on oxygen to give NH$_2$CONH(OR'), then on nitrogen to give NH$_2$CON(R")(OR'), by successive treatment with the alkylating agents R'X and R"X, respectively, in the presence of a suitable base. Suitable base and alkylating agents include those described by Kreutzkamp and Messinger (Chem. Ber. 100, 3463–3465 (1967) and Danen et al (J. Am. Chem. Soc. 1973, 95, 5716–5724). Hydrolysis of these alkylated hydroxyurea derivatives yields the amines R'ONH$_2$ and R'ONHR", which correspond to certain formula $R_8R_9$NH amines. The chemist skilled in the art can adapt the procedures described in this paragraph to other alkylating agents R, R' and R"—X to prepare other amines of formula $R_8R_9$NH wherein $R_8$—N or $R_9$—N are oxygen-nitrogen linked. Uno et al (SynLett 1991, 559–560) describe the BF$_3$-catalyzed addition of an organometallic reagent R—Li to an O-alkyl oxime of formula R'CH=N—OR", to give compounds of formula R'RCH—NH(OR"). This route may also be used to give compounds of formula $R_8R_9$NH wherein one of $R_8$—NH or $R_9$—NH are oxygen-nitrogen linked.

Prodrugs of this invention where a carboxyl group in a carboxylic acid of Formula I is replaced by an ester may be prepared by combining the carboxylic acid with the appropriate alkyl halide in the presence of a base such as potassium carbonate in an inert solvent such as dimethylformamide at a temperature of about 0 to 100° C. for about 1 to about 24 hours. Alternatively the acid is combined with appropriate alcohol as solvent in the presence of a catalytic amount of acid such as concentrated sulfuric acid at a temperature of about 20 to 120° C., preferably at reflux, for about 1 hour to about 24 hours. Another method is the reaction of the acid with a stoichiometric amount of the alcohol in the presence of a catalytic amount of acid in an inert solvent such as tetrahydrofuran, with concomitant removal of the water being produced by physical (e.g. Dean-Stark trap) or chemical (e.g. molecular sieves) means.

Prodrugs of this invention where an alcohol function has been derivatized as an ether may be prepared by combining the alcohol with the appropriate alkyl bromide or iodide in the presence of a base such as potassium carbonate in an inert solvent such as dimethylformamide at a temperature of about 0 to 100° C. for about 1 to about 24 hours. Alkanoylaminomethyl ethers may be obtained by reaction of the alcohol with a bis-(alkanoylamino)methane in the presence of a catalytic amount of acid in an inert solvent such as tetrahydrofuran, according to a method described in U.S. Pat. No. 4,997,984. Alternatively, these compounds may be prepared by the methods described by Hoffman et al. in J. Org. Chem. 1994, 59, 3530.

The dialkylphosphate esters may be prepared by reaction of the alcohol with a dialkyl chlorophosphate in the presence of a base in an inert solvent such as tetrahydrofuran. The dihydrogen phosphates may be prepared by reaction of the alcohol with a diaryl or dibenzyl chlorophosphate as described above, followed by hydrolysis or hydrogenation in the presence of a noble metal catalyst, respectively.

Glycosides are prepared by reaction of the alcohol and a carbohydrate in an inert solvent such as toluene in the presence of acid. Typically the water formed in the reaction is removed as it is being formed as described above. An alternate procedure is the reaction of the alcohol with a suitably protected glycosyl halide in the presence of base followed by deprotection.

N-(1-hydroxyalkyl) amides, N-(1-hydroxy-1-(alkoxycarbonyl)methyl) amides or compounds where $R_2$ has been replaced by C(OH)C(O)OY may be prepared by the reaction of the parent amide or indole with the appropriate aldehyde under neutral or basic conditions (e.g. sodium ethoxide in ethanol) at temperatures between 25 and 70° C. N-alkoxymethyl indoles or N-1-(alkoxy)alkyl indoles can be obtained by reaction of the N-unsubstituted indole with the necessary alkyl halide in the presence of a base in an inert solvent. 1-(N,N-dialkylaminomethyl) indole, 1-(1-(N,N-dialkylamino)ethyl) indole and N,N-dialkylaminomethyl amides (e.g. $R_3$=CH$_2$N(CH$_3$)$_2$) may be prepared by the reaction of the parent N-H compound with the appropriate aldehyde and amine in an alcoholic solvent at 25 to 70° C.

The prodrugs of this invention where $R_2$ and $R_3$ are a common carbon may be prepared by reaction of the parent compound (drug) with benzaldehyde or a ketone or its dimethyl acetal in an inert solvent in the presence of a catalytic amount of acid with concomitant water or methanol removal.

The starting materials and reagents for the above described reaction schemes (e.g., amines, substituted indole carboxylic acids, substituted indoline carboxylic acids, amino acids), although the preparation of most of which are described above, are also readily available or can be easily synthesized by those skilled in the art using conventional methods of organic synthesis. For example, many of the intermediates used herein to prepare compounds of Formula I are, are related to, or are derived from amino acids found in nature, in which there is a large scientific interest and commercial need, and accordingly many such intermediates are commercially available or are reported in the literature or are easily prepared from other commonly available substances by methods which are reported in the literature. Such intermediates include, for example, Formula XXX, Formula XLII, Formula XXXII and Formula XXXIII compounds.

Some compounds of Formula I have asymmetric carbon atoms and therefore are enantiomers or diastereomers. Diasteromeric mixtures can be separated into their individual diastereomers on the basis of their physical chemical differences by methods known per se., for example, by chromatography and/or fractional crystallization. Enantiomers (e.g., of Formula III, VIII or IX) can be separated by converting the enantiomeric mixture into a diasteromeric mixture by reaction with an appropriate optically active compound (e.g., alcohol), separating the diastereomers and converting (e.g., hydrolyzing) the individual diastereomers to the corresponding pure enantiomers. All such isomers, including diastereomers, enantiomers and mixtures thereof are considered as part of this invention.

Although many compounds of this invention are not ionizable at physiological conditions, some of the compounds of this invention are ionizable at physiological conditions. Thus, for example some of the compounds of this invention are acidic and they form a salt with a pharmaceutically acceptable cation. All such salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate.

In addition, some of the compounds of this invention are basic, and they form a salt with a pharmaceutically acceptable anion. All such salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate. In addition, when the compounds of this invention form hydrates or solvates they are also within the scope of the invention.

The utility of the compounds of the present invention as medical agents in the treatment of metabolic diseases (such as are detailed herein) in mammals (e.g., humans) is demonstrated by the activity of the compounds of this invention in conventional assays and the in vitro and in vivo assays described below. Such assays also provide a means whereby the activities of the compounds of this invention can be compared with the activities of other known compounds. The results of these comparisons are useful for determining dosage levels in mammals, including humans, for the treatment of such diseases.

The purified human liver glycogen phosphorylase a (HLGPa) is obtained by the following procedure.

Expression and fermentation:

The HLGP cDNA is expressed from plasmid pKK233-2 (Pharmacia Biotech. Inc., Piscataway, N.J.) in *E. coli* strain XL-1 Blue (Stratagene Cloning Systems, LaJolla, Calif.).

The strain is inoculated into LB medium (consisting of 10 g tryptone, 5 g yeast extract, 5 g NaCl, and 1 ml 1N NaOH per liter) plus 100 mg/L ampicillin, 100 mg/L pyridoxine and 600 mg/L $MnCl_2$ and grown at 37° C. to a cell density of $OD_{550}$=1.0. At this point, the cells are induced with 1 mM isopropyl-1-thio-β-D-galactoside (IPTG). Three hours after induction the cells are harvested by centrifugation and cell pellets are frozen at −70° C. until needed for purification.

Purification of Glycogen Phosphorylase:

The cells in pellets described above are resuspended in 25 mM β-glycerophosphate (pH 7.0) with 0.2 mM DTT, 1 mM $MgCl_2$, plus the following protease inhibitors:

| | |
|---|---|
| 0.7 μg/mL | Pepstatin A |
| 0.5 μg/mL | Leupeptin |
| 0.2 mM | Phenylmethylsulfonyl fluoride (PMSF), and |
| 0.5 mM | EDTA, | lysed by pretreatment with 200 μg/mL lysozyme and 3 μg/mL DNAase followed by sonication in 250 mL batches for 5×1.5 minutes on ice using a Branson Model 450 ultrasonic cell disrupter (Branson Sonic Power Co., Danbury Conn.). The lysates are cleared by centrifugation at 35,000×g for one hour followed by filtration through 0.45 micron filters. HLGP in the soluble fraction of the lysates (estimated to be less than 1% of the total protein) is purified by monitoring the enzyme activity (as described in HLGPa Activity Assay section, below) from a series of chromatographic steps detailed below.

Immobilized Metal Affinity Chromatography (IMAC):

This step is based on the method of Luong et al (Luong et al. Journal of Chromatography (1992) 584, 77–84.). 500 mL of the filtered soluble fraction of cell lysates (prepared from approximately 160 g of original cell pellet) are loaded onto a 130 mL column of IMAC Chelating-Sepharose (Pharmacia LKB Biotechnology, Piscataway, N.J.) which has been charged with 50 mM $CuCl_2$ and 25 mM β-glycerophosphate, 250 mM NaCl and 1 mM imidazole at pH 7 equilibration buffer. The column is washed with equilibration buffer until the $A_{280}$ returns to baseline. The sample is then eluted from the column with the same buffer containing 100 mM imidazole to remove the bound HLGP and other bound proteins. Fractions containing the HLGP activity are pooled (approximately 600 mL), and ethylenediaminetetraacetic acid (EDTA), DL-dithiothreitol (DTT), phenylmethylsulfonyl fluoride (PMSF), leupeptin and pepstatin A are added to obtain 0.3 mM, 0.2 mM, 0.2 mM, 0.5 μg/mL and 0.7 μg/mL concentrations respectively. The pooled HLGP is desalted over a Sephadex G-25 column (Sigma Chemical Co., St. Louis, Mo.) equilibrated with 25 mM Tris-HCl (pH 7.3), 3 mM DTT buffer (Buffer A) to remove imidazole and is stored on ice until the second chromatographic step.

5'-AMP-Seoharose Chromatoaraphy:

The desalted pooled HLGP sample (approximately 600 mL) is next mixed with 70 mL of 5'-AMP Sepharose (Pharmacia LKB Biotechnology, Piscataway, N.J.) which has been equilibrated with Buffer A (see above). The mixture is gently agitated for one hour at 22° C. then packed into a column and washed with Buffer A until the A280 returns to baseline. HLGP and other proteins are eluted from the column with 25 mM Tris-HCl, 0.2 mM DTT and 10 mM adenosine 5'-monophosphate (AMP) at pH 7.3 (Buffer B). HLGP-containing fractions are pooled following identification by determining enzyme (described below) activity and visualizing the M, approximately 97 kdal HLGP protein band by sodium dodecyl sulfate polyacrylamide gel electrophoresis (SDS-PAGE) followed by silver staining (2D-silver Stain II "Daiichi Kit", Daiichi Pure Chemicals Co., LTD., Tokyo, Japan) and then pooled. The pooled HLGP is dialyzed into 25 mM β-glycerophosphate, 0.2 mM DTT, 0.3 mM EDTA, 200 mM NaCl, pH 7.0 buffer (Buffer C) and stored on ice until use.

Determination of HLGP Enzyme Activity

A) Activation of HLGP: Conversion of HLGPb to HLGPa

Prior to the determination of HLGP enzyme activity, the enzyme is converted from the inactive form as expressed in *E. coli* strain XL-1 Blue (designated HLGPb) (Stragene Cloning Systems, La Jolla, Calif.) to the active form (designated HLGPa) by phosphorylation of HLGP using phosphorylase kinase as follows:

HLGPb reaction with Immobilized Phosrhorylase Kinase

Phosphorylase kinase (Sigma Chemical Company, St. Louis, Mo.) is immobilized on Affi-Gel 10 (BioRad Corp., Melvile, N.Y.) as per the manufacturer's instructions. In brief, the phosphorylase kinase enzyme (10 mg) is incubated with washed Affi-Gel beads (1 mL) in 2.5 mL of 100 mM HEPES and 80 mM $CaCl_2$ at pH 7.4 for 4 hours at 4° C. The Affi-Gel beads are then washed once with the same buffer prior to blocking with 50 mM HEPES and 1 M glycine methyl ester at pH 8.0 for one hour at room temperature. Blocking buffer is removed and replaced with 50 mM HEPES (pH 7.4), 1 mM β-mercaptoethanol and 0.2% $NaN_3$ for storage. Prior to use to convert HLGPb to HLGPa, the Affi-Gel immobilized phosphorylase kinase beads are equilibrated by washing in the buffer used to perform the kinase reaction, consisting of 25 mM β-glycerophosphate, 0.3 mM DTT, and 0.3 mM EDTA at pH 7.8 (kinase assay buffer).

The partially purified, inactive HLGPb obtained from 5'-AMP-Sepharose chromatography above is diluted 1:10 with the kinase assay buffer then mixed with the aforementioned phosphorylase kinase enzyme immobilized on the Affi-Gel beads. NaATP is added to 5 mM and $MgCl_2$ to 6 mM. The resulting mixture is mixed gently at 25° C. for 30 to 60 minutes. The sample is removed from the beads and the percent activation of HLGPb by conversion to HLGPa is estimated by determining HLGP enzyme activity in the presence and absence of 3.3 mM AMP. The percentage of total HLGP enzyme activity due to HLGPa enzyme activity (AMP-independent) is then calculated as follows:

$$\% \text{ of total } HLGP \text{ as } HLGP_a = \frac{HLGP \text{ activity} - AMP}{HLGP \text{ activity} + AMP}$$

B) HLGPa Activity Assay:

The hypoglycemic activity (also the other disease/condition treating/preventing activities described herein) of the compounds of this invention can be indirectly determined by assessing the effect of the compounds of this invention on the activity of the activated form of glycogen phosphorylase (GPa) by one of two methods; glycogen phosphorylase a activity is measured in the forward direction by monitoring the production of glucose-1-phosphate from glycogen or by following the reverse reaction, measuring glycogen synthesis from glucose-1-phosphate by the release of inorganic phosphate. All reactions are run in triplicate in 96-well microtiter plates and the change in absorbance due to formation of the reaction product is measured at the wavelength specified below in a MCC/340 MKII Elisa Reader (Lab Systems, Finland), connected to a Titertech Microplate Stacker (ICN Biomedical Co, Huntsville, Ala.).

To measure the HLGPa enzyme activity in the forward direction, the production of glucose-1-phosphate from glycogen is monitored by the multienzyme coupled general method of Pesce et al. [Pesce, M. A., Bodourian, S. H., Harris, R. C. and Nicholson, J. F. (1977) Clinical Chemistry 23,1711–1717] modified as follows: 1 to 100 µg phosphorylase a, 10 units phosphoglucomutase and 15 units glucose-6-phosphate dehydrogenase (Boehringer Mannheim Biochemicals, Indianapolis, Ind.) are diluted to 1 mL in Buffer A (described hereinafter). Buffer A is at pH 7.2 and contains 50 mM HEPES, 100 mM KCl, 2.5 mM ethyleneglycoltetraacetic acid (EGTA), 2.5 mM $MgCl_2$, 3.5 mM $KH_2PO_4$ and 0.5 mM dithiothreitol. 20 µl of this stock is added to 80 µl of Buffer A containing 0.47 mg/mL glycogen, 9.4 mM glucose, 0.63 mM of the oxidized form of nicotinamide adenine dinucleotide phosphate ($NADP^+$). The compounds to be tested are added as 5 µL of solution in 14% dimethylsulfoxide (DMSO) prior to the addition of the enzymes. The basal rate of HLGPa enzyme activity in the absence of inhibitors is determined by adding 5 µL of 14% DMSO and a fully-inhibited rate of HLGPa enzyme activity is obtained by adding 20 µL of 50 mM of the positive control test substance, caffeine. The reaction is followed at room temperature by measuring the conversion of oxidized $NADP^+$ to reduced NADPH at 340 nm.

To measure HLGPa enzyme activity in the reverse direction, the conversion of glucose-1-phosphate into glycogen plus inorganic phosphate is measured by the general method described by Engers et al. [Engers, H. D., Shechosky, S. and Madsen, N. B. (1970) Can. J. Biochem. 48, 746–754] modified as follows: 1 to 100 ug HLGPa is diluted to 1 mL in Buffer B (described hereinafter). Buffer B is at pH 7.2 and contains 50 mM HEPES, 100 mM KCl, 2.5 mM EGTA, 2.5 mM $MgCl_2$ and 0.5 mM dithiothreitol. 20 µL of this stock is added to 80 µL of Buffer B with 1.25 mg/mL glycogen, 9.4 mM glucose, and 0.63 mM glucose-1-phosphate. The compounds to be tested are added as 5 µL of solution in 14% DMSO prior to the addition of the enzyme. The basal rate of HLGPa enzyme activity in the absence of added inhibitors is determined by adding 5 µL of 14% DMSO and a fully-inhibited rate of HLGPa enzyme activity is obtained by adding 20 µL of 50 mM caffeine: This mixture is incubated at room temperature for 1 hour and the inorganic phosphate released from the glucose-1-phosphate is measured by the general method of Lanzetta et al. [Lanzetta, P. A., Alvarez, L. J., Reinach, P. S. and Candia, O. A. (1979) Anal. Biochem. 100, 95–97] modified as follows: 150 µL of 10 mg/mL ammonium molybdate, 0.38 mg/mL malachite green in 1 N HCl is added to 100 µL of the enzyme mix. After a 20 minute incubation at room temperature, the absorbance is measured at 620 nm.

The compounds of this invention are readily adapted to clinical use as hypoglycemic agents. The hypoglycemic activity of the compounds of this invention can be determined by the amount of test compound that reduces glucose levels relative to a vehicle without test compound in male ob/ob mice. The test also allows the determination of an approximate minimal effective dose (MED) value for the in vivo reduction of plasma glucose concentration in such mice for such test compounds.

Since the concentration of glucose in blood is closely related to the development of diabetic disorders, these compounds by virtue of their hypoglycemic action, prevent, arrest and/or regress diabetic disorders.

Five to eight week old male C57BL/6J-ob/ob mice (obtained from Jackson Laboratory, Bar Harbor, Me.) are housed five per cage under standard animal care practices. After a one week acclimation period, the animals are weighed and 25 microliters of blood are collected from the retro-orbital sinus prior to any treatment. The blood sample is immediately diluted 1:5 with saline containing 0.025% sodium heparin, and held on ice for metabolite analysis. Animals are assigned to treatment groups so that each group has a similar mean for plasma glucose concentration. After group assignment, animals are dosed orally each day for four days with the vehicle consisting of either: 1) 0.25% w/v methyl cellulose in water without pH adjustment; or 2) 0.1% Pluronic® P105 Block Copolymer Surfactant (BASF Corporation, Parsippany, N.J.) in 0.1% saline without pH adjustment. On day 5, the animals are weighed again and then dosed orally with the test compound or the vehicle alone. All drugs are administered in vehicle consisting of either: 1) 0.25% w/v methyl cellulose in water without pH adjustment; or 2) 10% DMSO/0.1% Pluronic® P105 (BASF Corporation, Parsippany, N.J.) in 0.1% saline without pH adjustment. The animals are then bled from the retro-orbital sinus three hours later for determination of blood metabolite levels. The freshly collected samples are centrifuged for two minutes at 10,000 xg at room temperature. The supematant is analyzed for glucose, for example, by the Abbott VP™ (Abbott Laboratories, Diagnostics Division, Irving, Tex.) and VP Super System® Autoanalyzer (Abbott Laboratories, Irving, Tex.), using the A-Gent™ Glucose-UV Test reagent system (Abbott Laboratories, Irving, Tex.) (a modification of the method of Richterich and Dauwalder, Schweizerische Medizinische Wochenschrift, 101, 860 (1971)) (hexokinase method) using a 100 mg/dL standard. Plasma glucose is then calculated by the equation: Plasma glucose (mg/dL)= Sample value×5×1.784=8.92× Sample value where 5 is the dilution factor and 1.784 is the plasma hematocrit adjustment (assuming the hematocrit is 44%).

The animals dosed with vehicle maintain substantially unchanged hyperglycemic glucose levels (e.g., greater than or equal to 250 mg/dL), animals treated with test compounds at suitable doses have significantly depressed glucose levels. Hypoglycemic activity of the test compounds is determined by statistical analysis (unpaired t-test) of the mean plasma glucose concentration between the test compound group and vehicle-treated group on day 5 The above assay carried out with a range of doses of test compounds allows the determination of an approximate minimal effective dose (MED) value for the in vivo reduction of plasma glucose concentration.

The compounds of this invention are readily adapted to clinical use as hyperinsulinemia reversing agents, triglyceride lowering agents and hypocholesterolemic agents. Such activity can be determined by the amount of test compound that reduces insulin, triglycerides or cholesterol levels relative to a control vehicle without test compound in male ob/ob mice.

Since the concentration of cholesterol in blood is closely related to the development of cardiovascular, cerebral vascular or peripheral vascular disorders, the compounds of this invention by virtue of their hypocholesterolemic action, prevent, arrest and/or regress atherosclerosis.

Since the concentration of insulin in blood is related to the promotion of vascular cell growth and increased renal sodium retention, (in addition to the other actions e.g., promotion of glucose utilization) and these functions are known causes of hypertension, the compounds of this invention by virtue of their hypolnsulinemic action, prevent, arrest and/or regress hypertension.

Since the concentration of triglycerides in blood contributes to the overall levels of blood lipids, the compounds of this invention by virtue of their triglyceride lowering activity prevent, arrest and/or regress hyperlipidemia.

Five to eight week old male C57BL/6J-ob/ob mice (obtained from Jackson Laboratory, Bar Harbor, Me.) are housed five per cage under standard animal care practices and fed standard rodent diet ad libitum. After a one week acclimation period, the animals are weighed and 25 microliters of blood are collected from the retro-orbital sinus prior to any treatment. The blood sample is immediately diluted 1:5 with saline containing 0.025% sodium heparin, and held on ice for plasma glucose analysis. Animals are assigned to treatment groups so that each group has a similar mean for plasma glucose concentration. The compound to be tested is administered by oral gavage as an about 0.02% to 2.0% solution (weight/volume (w/v)) in either 1) 10% DMSO/ 0.1% Pluronic® P105 Block Copolymer Surfactant (BASF Corporation, Parsippany, N.J.) in 0.1% saline without pH adjustment or 2) 0.25% w/v methylcellulose in water without pH adjustment. Single daily dosing (s.i.d.) or twice daily dosing (b.i.d.) is maintained for 1 to 15 days. Control mice receive the 10% DMSO/0.1% Pluronic® P105 in 0.1% saline without pH adjustment or the 0.25% w/v methylcellulose in water without pH adjustment only.

Three hours after the last dose is administered, the animals are sacrificed by decapitation and trunk blood is collected into 0.5 mL serum separator tubes containing 3.6 mg of a 1:1 weight/weight sodium fluoride: potassium oxalate mixture. The freshly collected samples are centrifuged for two minutes at 10,000 xg at room temperature, and the serum supernatant is transferred and diluted 1:1 volume/volume with a 1TIU/mL aprotinin solution in 0.1% saline without pH adjustment.

The diluted serum samples are then stored at −80° C. until analysis. The thawed, diluted serum samples are analyzed for insulin, triglycerides, and cholesterol levels. Serum insulin concentration is determined using Equate® RIA INSULIN kits (double antibody method; as specified by the manufacturer) purchased from Binax, South Portland, Me. The inter assay coefficient of variation is $\leq 10\%$. Serum triglycerides are determined using the Abbott VP™ and VP Super System® Autoanalyzer (Abbott Laboratories, Irving, Tex.), using the A-Gent™ Triglycerides Test reagent system (Abbott Laboratories, Diagnostics Division, Irving, Tex.) (lipase-coupled enzyme method; a modification of the method of Sampson, et al., Clinical Chemistry 21, 1983 (1975)). Serum total cholesterol levels are determined using the Abbott VP™ and VP Super System® Autoanalyzer (Abbott Laboratories, Irving, Tex.), and A-Gent™ Cholesterol Test reagent system (cholesterol esterase-coupled enzyme method; a modification of the method of Allain, et al. Clinical Chemistry 20, 470 (1974)) using a 100 and 300 mg/dL standards. Serum insulin, triglycerides, and total cholesterol levels are then calculated by the equations, Serum insulin ($\mu$U/mL)=Sample value×2

Serum triglycerides (mg/dL)=Sample value×2

Serum total cholesterol (mg/dL)=Sample value×2 where 2 is the dilution factor.

The animals dosed with vehicle maintain substantially unchanged, elevated serum insulin (e.g. 225 $\mu$U/mL), serum triglycerides (e.g. 225 mg/dl), and serum total cholesterol (e.g. 160 mg/dL) levels, while animals treated with test compounds of this invention generally display reduced serum insulin, triglycerides, and total cholesterol levels. The serum insulin, triglycerides, and total cholesterol lowering activity of the test compounds are determined by statistical analysis (unpaired t-test) of the mean serum insulin, triglycerides, or total cholesterol concentration between the test compound group and the vehicle-treated control group.

Activity in providing protection from damage to heart tissue for the compounds of this invention can be demonstrated in vitro along the lines presented in Butwell et al., Am. J. Physiol., 264, H1884–H1889, 1993 and Allard et al., Am. J. Physio., 1994, 267, H66–H74. Experiments are performed using an isovolumic isolated rat heart preparation, essentially as described in the above-referenced article. Normal male Sprague-Dawley rats, male Sprague-Dawley rats treated to possess cardiac hypertrophy by an aortic banding operation, acutely diabetic male BB/W rats, or non-diabetic BB/W age matched control rats are pretreated with heparin (1000 u, i.p.), followed by pentobarbital (65 mg/kg, i.p.). After deep anesthesia is achieved as determined by the absence of a foot reflex, the heart is rapidly excised and placed into iced saline. The heart is retrogradely perfused through the aorta within 2 minutes. Heart rate and ventricular pressure are determined using a latex balloon in the left ventricle with high pressure tubing connected to a pressure transducer. The heart is perfused with a perfusate solution consisting of (mM) NaCl 118, KCl 4.7, $CaCl_2$ 1.2, $MgCl_2$ 1.2, $NaHCO_3$ 25, glucose 11. The perfusion apparatus is tightly temperature-controlled with heated baths used for the perfusate and for the water jacketing around the perfusion tubing to maintain heart temperature at 37° C. Oxygenation of the perfusate is provided by a pediatric hollow fiber oxygenator (Capiax, Terumo Corp., Tokyo, Japan) immediately proximal to the heart. Hearts are exposed to perfusion solution±test compound for about 10 minutes or more, followed by 20 minutes of global ischemia and 60 minutes of reperfusion in the absence of the test compound. The heart beats of the control and test compound treated hearts are compared in the period following ischemia. The left ventricular pressure of the control and test compound treated hearts are compared in the period following ischemia. At the end of the experiment, hearts are also perfused and stained to determine the ratio of infarct area relative to the area at risk (%IA/AAR) as described below.

The therapeutic effects of the compounds of this invention in preventing heart tissue damage otherwise resulting from an ischemic insult can also be demonstrated in vivo along lines presented in Liu et al., Circulation, Vol. 84, No. 1, (July 1991), as described specifically herein. The in vivo assay tests the cardioprotection of the test compound relative to the control group which receives saline vehicle. As background information, it is noted that brief periods of myocardial ischemia followed by coronary artery reperfusion protects the heart from subsequent severe myocardial ischemia (Murry et al., Circulation 74:1124–1136, 1986). Cardioprotection, as indicated by a reduction in infarcted myocardium, can be induced pharmacologically using intravenously administered adenosine receptor agonists in intact, anesthetized rabbits studied as an in situ model of myocardial ischemic preconditioning (Liu et al., Circulation 84:350–356, 1991). The in vivo assay tests whether compounds can pharmacologically induce cardioprotection, i.e., reduced myocardial infarct size, when parenterally administered to intact, anesthetized rabbits. The effects of the compounds of this invention can be compared to ischemic preconditioning using the A1 adenosine agonist, $N^6$-1-(phenyl-2R-isopropyl) adenosine (PIA) that has been shown to pharmacologically induce cardioprotection in intact anesthetized rabbits studied in situ (Liu et al., Circulation 84:350–356, 1991). The exact methodology is described below.

Surgery: New Zealand White male rabbits (3–4 kg) are anesthetized with sodium pentobarbital (30 mg/kg, i.v.). A tracheotomy is performed via a ventral midline cervical incision and the rabbits are ventilated with 100% oxygen using a positive pressure ventilator. Catheters are placed in the left jugular vein for drug administration and in the left carotid artery for blood pressure measurements. The hearts are then exposed through a left thoracotomy and a snare (00 silk) placed around a prominent branch of the left coronary artery. Ischemia is induced by pulling the snare tight and clamping it in place. Releasing the snare allowed the affected area to reperfuse. Myocardial ischemia is evidenced by regional cyanosis; reperfusion was evidenced by reactive hyperemia.

Protocol: Once arterial pressure and heart rate has been stable for at least 30 minutes the experiment is started. Ischemic preconditioning is induced by twice occluding the coronary artery for 5 min followed by a 10 min reperfusion. Pharmacological preconditioning is induced by twice infusing test compound over, for example 5 minutes and allowing 10 minutes before further intervention or by infusing the adenosine agonist, PIA (0.25 mg/kg). Following ischemic preconditioning, pharmacological preconditioning or no conditioning (unconditioned, vehicle control) the artery is occluded for 30 minutes and then reperfused for two hours to induce myocardial infarction. The test compound and PIA are dissolved in saline or other suitable vehicle and delivered at 1 to 5 ml/kg, respectively.

Staining (Liu et al., Circulation 84:350–356, 1991): At the end of the 2 hour reperfusion period, the hearts are quickly removed, hung on a Langendorff apparatus, and flushed for 1 minute with normal saline heated to body temperature (38° C). The silk suture used as the snare is then tied tightly to reocclude the artery and a 0.5% suspension of fluorescent particles (1–10 $\mu$m) is infused with the perfusate to stain all of the myocardium except the area at risk (nonfluorescent ventricle). The hearts are then quickly frozen and stored overnight at –20° C. On the following day, the hearts are cut into 2 mm slices and stained with 1% triphenyl tetrazolium chloride (TTC). Since TTC reacts with living tissue, this stain differentiates between living (red stained) tissue, and dead tissue (unstained infarcted tissue). The infarcted area (no stain) and the area at risk (no fluorescent particles) are calculated for each slice of left ventricle using a pre-calibrated image analyzer. To normalize the ischemic injury for differences in the area at risk between hearts, the data is expressed as the ratio of infarct area vs. area at risk (%IA/ARR). All data is expressed as Mean±SEM and compared statistically using single factor ANOVA or unpaired t-test. Significance is considered as $p<0.05$.

Administration of the compounds of this invention can be via any method which delivers a compound of this invention preferentially to the liver and/or cardiac tissues. These methods include oral routes, parenteral, intraduodenal routes, etc. Generally, the compounds of the present invention are administered in single (e.g., once daily) or multiple doses.

However, the amount and timing of compound(s) administered will, of course, be dependent on the particular disease/condition being treated, the subject being treated, on the severity of the affliction, on the manner of administration and on the judgment of the prescribing physician. Thus, because of patient to patient variability, the dosages given below are a guideline and the physician may titrate doses of the drug to achieve the activity (e.g., glucose lowering activity) that the physician considers appropriate for the patient. In considering the degree of activity desired, the physician must balance a variety of factors such as starting level, other risk (cardiovascular) factors, presence of preexisting disease, and age of the patient and the patient's motivation.

In general an effective dosage for the activities of this invention, for example, the blood glucose, triglycerides, and cholesterol lowering activities and hyperinsulinemia reversing activities of the compounds of this invention is in the range of 0.005 to 50 mg/kg/day, preferably 0.01 to 25 mg/kg/day and most preferably 0.1 to 15 mg/kg/day.

Generally, the compounds of this invention are administered orally, but parenteral administration (e.g., intravenous, intramuscular, subcutaneous or intramedullary) may be utilized, for example, where oral administration is inappropriate for the instant target or where the patient is unable to ingest the drug. Topical administration may also be indicated, for example, where the patient is suffering from gastrointestinal disorders or whenever the medication is best applied to the surface of a tissue or organ as determined by the attending physician.

The compounds of the present invention are generally administered in the form of a pharmaceutical composition comprising at least one of the compounds of this invention together with a pharmaceutically acceptable vehicle or diluent. Thus, the compounds of this invention can be administered individually or together in any conventional oral, parenteral or transdermal dosage form.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of transdermal (e.g.,topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in this art. For examples, see *Remington's Pharmaceutical Sciences,* Mack Publishing Company, Easter, Pa., 15th Edition (1975).

Pharmaceutical compositions according to the invention may contain 0.1%–95% of the compound(s) of this invention, preferably 1%–70%. In any event, the composition or formulation to be administered will contain a quantity of a compound(s) according to the invention in an amount effective to treat the disease/condition of the subject being treated, i.e., a glycogen phosphorylase dependent disease/condition.

General Experimental Procedures for Examples 1–99 and 166–172

NMR spectra were recorded on a Varian XL-300 (Varian Co., Palo Alto, Calif.) or Bruker AM-300 spectrometer (Bruker Co., Billerica, Mass.) at about 23° C. at 300 MHz for proton and 75.4 mHz for carbon nuclei. Chemical shifts are expressed in parts per million downfield from trimethylsilane. Resonances designated as exchangeable did not appear in a separate NMR experiment where the sample was shaken with several drops of $D_2O$ in the same solvent. FAB-MS spectra were obtained on a VG70-2505 spectrometer (V4 analytical LTD., Wythanshaw, Manchester, U.K.) using a liquid matrix consisting of 3:1 dithiothreitol/dithioerythritol. Thermospray MS (TSPMS) were obtained on a Fisons Trio-1000 spectrometer (Fisons Co., Valencia, Calif.) using ammonia ionization. Chemical ionization mass spectra were obtained on a Hewlett-Packard 5989 instrument (Hewlett-Packard Co., Palo Alto, Calif.) (ammonia ionization, PBMS). Where the intensity of chlorine or bromine-containing ions are described the expected intensity ratio was observed (approximately 3:1 for $^{35}Cl/^{37}Cl$-containing ions) and 1:1 for $^{79}Br/^{81}Br$-containing ions) and the intensity of only the lower mass ion is given.

HPLC was performed with 214 nM detection on a 250× 4.6 mm Rainin Microsorb C-18 column (Rainin Co., Woburn, Mass.) eluted isocratically by a two-pump/mixer system supplying the indicated mixture of acetonitrile and aqueous pH 2.1 (with $H_3PO_4$) 0.1M $KH_2PO_4$, respectively, at 1.5 mL/min. Samples were injected in a 1:1 mixture of acetonitrile and pH 7.0 phosphate buffer (0.025 M in each $Na_2HPO_4$ and $KH2PO_4$). Percent purities refer to percent of total integrated area usually over a 10 to 15 minute run. Melting points are uncorrected and were determined on a Buchi 510 melting point apparatus (Buchi Laboratorums-Technik Ag., Flawil, Switzerland) where melting points of 120.5–122° C. for benzoic acid and 237.5–240.5° C. for p-chlorobenzoic acid (Aldrich 99+% grades) were obtained. Column chromatography was performed with Amicon silica gel (30 uM, 60A pore size) (Amicon D Vision, W. R. Grace & Co., Beverly, Mass.) in glass columns under low nitrogen pressure. Unless otherwise specified, reagents were used as obtained from commercial sources. Dimethylformamide, 2-propanol, tetrahydrofuran, and dichloromethane used as reaction solvents were the anhydrous grade supplied by Aldrich Chemical Company (Milwaukee, Wis.). Microanalyses were performed by Schwarzkopf Microanalytical Laboratory, Woodside, N.Y. The terms "concentrated" and coevaporated refer to removal of solvent at water aspirator pressure on a rotary evaporator with a bath temperature of less than 45° C. Reactions conducted at "0–20° C." or "0–25° C." were conducted with initial cooling of the vessel in an insulated ice bath which was allowed to want to room temperature over several hours. The abbreviation "min" and "h" stand for "minutes" and "hours" respectively.

Procedure A (Peptide Coupling Using DEC)

An 0.1–0.7 M solution of the primary amine (1.0 equiv, or a primary amine hydrochloride and 1.0 to 1.3 equivalents of triethylamine per equiv HCl) in dichloromethane (unless other solvent specified), is treated sequentially at 25° C. with 0.95 to 1.2 equivalent of the specified carboxylic acid, 1.2 to 1.8 equivalent hydroxybenzotriazole hydrate (usually 1.5 equivalent relative to the carboxylic acid), and 0.95–1.2 equivalent (corresponding in mole ratio to the carboxylic acid) 1-(3-dimethylaminopropyl)3-ethylcarbodiimide hydrochloride (DEC) and the mixture is stirred for 14 to 20 hours. (See Note 1 below). The mixture is diluted with ethyl acetate, washed 2 to 3 times with 1 or 2N NaOH, 2 to 3 times with 1 or 2N HCl (Note 2), the organic layer dried over $MgSO_4$, and concentrated giving crude product which is purified by chromatography on silica gel, trituration, or recrystallization, as specified using the specified solvents. Purified products were analyzed by RP-HPLC and found to be of greater than 95% purity unless otherwise noted. Reactions conducted at 0 to 25° C. were conducted with initial cooling of the vessel in an insulated ice bath which was allowed to warm to room temperature over several hours.

Note 1: On larger scale couplings (>50 mL solvent) the mixture was concentrated at this point and the residue dissolved in ethyl acetate.

Note 2: If the product contained ionizable amine functionality the acid wash was omitted. Exceptions in the use of Procedure A are noted individually (where appropriate below) usually in parentheses, immediately following mention of Procedure A.

EXAMPLE 1

(2S)-[(5-Chloro-1H-indole-2-carbonyl)-amino]-3-phenyl-propionic acid methyl ester L-Phenylalanine methyl ester hydrochloride (77.0 mmol) and 5-chloro-1 H-indole-2-carboxylic acid (77 mmol) were coupled according to procedure A (0–25° C.) and the product purified by chromatography on silica gel in 10 and 20% ethyl acetate-hexanes giving the title substance as an off-white solid (22.12 g, 81%): mp 156–157° C.; HPLC (60/40) 9.5 minutes (98%); PBMS 357/359 (MH+, 100%).

$^1$H NMR ($CDCl_3$) δ9.40 (br, 1H), 7.60 (d, 1H, J=ca 1 Hz), 7.35 (d, 1H, J=8.9 Hz), 7.3–7.2 (m, 4H), 7.13 (m, 2H), 6.74 (d, 1H, J=1.7 Hz), 6.62 (d, 1H, J=7.5 Hz), 5.11 (m, 1H), 3.77 (s, 3H), 3.26 (m, 2H);

Anal. Calcd for $C_{19}H_{17}ClN_2O_3$: C, 63.96; H, 4.80; N, 7.85.

Found: C, 64.24; H, 4.84; N, 8.02.

EXAMPLE 2

2-[(5-Chloro-1H-indole-2-carbonyl)-amino]phenyl-propionic acid

Aqueous 2M LiOH (33.10 ml) was added to a solution of (2S)-[(5-chloro-1H-indole-2carbonyl)-amino]-3-phenyl-propionic acid methyl ester (21.47 g, 60 mmol) in THF (140 ml) at 0–5° C. After 0.5 hour, the mixture was partially concentrated, acidified to pH 1–2 with 6N HCl, concentrated to dryness, and the solids washed with water and then ether to yield a colorless solid (18.78 g, 91%): mp 248–255° C.; HPLC (60/40) 5.21 minutes (98%); TSPMS 343/345 (MH+, 100%).

$^1$H NMR (DMSO-$d_6$) δ12.85 (br, 1H), 11.75 (d, 1H, J=<1 Hz), 8.84 (d, 1H, J=8.4 Hz), 7.35–7.14 (m, 7H), 4.65 (m, 1H), 3.20 (A of AB, 1H, J=4.5, 13.9 Hz), 3.07 (B of AB, 1H, J=10.8, 13.8 Hz);

Anal. Calcd for $C_{18}H_{15}ClN_2O_3$: C, 63.07; H, 4.41; N. 8.17.

Found: C, 62.90; H, 4.60; N, 8.04.

EXAMPLE 3

[(5-Chloro-1H indole-2carbonyl)-amino]-acetic acid methyl ester

Glycine methyl ester hydrochloride (50 mmol) and 5-chloro-1H-indole-2-carboxylic acid (50 mmol) were coupled according to procedure A, substituting the following workup: the reaction mixture was stirred in ethyl acetate (250 mL), hexanes (50 mL) and 1N NaOH (50 mL) and the suspension was filtered. The solid was washed with 1N NaOH, 1N HCl, with water, ethyl acetate, and dried: Yield 11.5 g, 86%; mp 252–254° C. with decomposition;

$^1$H NMR (DMSO-$d_6$) δ11.87 (br,1H), 9.05 (t, 1H, J=6.0 Hz), 7.72 (d, 1H, J=2.0 Hz), 7.45 (d, 1H, J=8.7 Hz), 7.19 (dd, 1H, J=2.0, 8.7 Hz), 4.05 (d, 2H, J=6.0 Hz), 3.91 (s, 3H);

Anal. Calcd for $C_{12}H_{11}ClN_2O_3$: C, 54.05; H, 4.16; N, 10.50.

Found: C, 54.11; H, 4.23; N, 10.56.

EXAMPLE 4

[(5-Chloro-1H-indole-2-carbonyl)-amino]-acetic acid

1N NaOH (35 ml) was added to a suspension of [(5-chloro-1H-indole-2-carbonyl)-amino]-acetic acid methyl ester (8.0 g, 30 mmol) in THF (100 ml) and the resulting mixture stirred for 18 hours at 25° C. The solution was acidified with 6N HCl (7 mL), the mixture concentrated, the solids suspended in water, filtered, and washed with water (7.42 g, 98%): HPLC (60/40) 2.89 minutes (100 %;)

$^1$H NMR (300 MHz, DMSO-$d_6$) δ12.68 (br, 1H), 11.85 (br, 1H), 8.95 (t, 1H, J=5.9 Hz), 7.72 (d, 1H, J=2.0 Hz), 7.44 (d, 1H, J=8.7 Hz), 7.19 (dd, 1H, J=2.0, 8.7 Hz), 7.14 (d, 1H, J=<2 Hz), 3.96 (d, 2H, J=5.9 Hz)

Anal. Calcd for $C_{11}H_9N_2O_3Cl$: C, 52.29; H, 3.59; N, 11.09.

Found: C, 52.26; H, 3.73; N, 11.20.

EXAMPLE 5

5-Chloro-1H-indole-2-carboxylic acid [2-((3RS)-hydroxy-pyrrolidin-1-yl)-2-oxo-ethyl]-amide 3-Pyrrolidinol (1.25 mmol) and [(5chloro-1H-indole-2-carbonyl)-amino]-acetic acid (1.19 mmol) were coupled according to Procedure A with the following workup: the reaction mixture was diluted with ethyl acetate and 2 N HCl, stirred 1 hour, the mixture filtered, and the resulting solids washed successively with 2 N HCl, 2 N NaOH, 2 N HCl, dried, triturated with 1:1 ether/hexanes and dried, giving an off-white solid: Yield 280 mg, 73 %; HPLC (60/40) 4.66 minutes (96%); PBMS 322/324 (MH+, 100%).

$^1$H NMR (DMSO-$d_6$) δ11.87 (br, 1H), 8.71 (q, 1H), 7.71 (d, 1H, J=2.1 Hz), 7.45 (d, 1H, J=8.8 Hz), 7.19 (dd, 1H, J=3.1, 8.8 Hz), 7.16 (s, 1H), 5.07 (d, 0.5H, J=3.6 Hz), 4.97 (d, 0.5H, J=3.1 Hz), 4.35 (m, 1H), 4.27 (m, 1H), 4.10 (t, 1H), 4.03 (d, 1H), 3.59 (m, 1H), 3.49–3.27 (m, 2H), 2.04–1.79 (m, 2H).

EXAMPLE 6

5-Chloro-1H-indole-2-carboxylic acid [2-(Cis-3.4-dihydroxy-pyrrolidin-1-yl)-2-oxo-ethyl]-amide (3R,4S)-3,4-Dihydroxypyrrolidine hydrochloride (the cis, or meso isomer, 1.79 mmol) and [(5-chloro-1H-indole-2-carbonyl)-amino]-acetic acid (0.85 mmol) were coupled according to procedure A (1:1 $CH_2Cl_2$/DMF reaction solvent) with the following workup: the reaction mixture was concentrated, the residue suspended in 10 ml EtOAc and 10 ml 2 N NaOH, the solids filtered and washed successively with aqueous 1 N NaOH, EtOAc, aqueous 1 N HCl, $H_2O$, and ether. This washing sequence was repeated and the resulting solids were suspended in EtOAc, stirred for 1 hour, filtered and dried: Yield 252 mg, 88%; HPLC (60/40) 2.33 minutes (93%); TSPMS 338/340 (MH+, 100%);

$^1$H NMR (DMSO-$d_6$) δ11.82 (s, 1H), 8.72 (t, 1H), 7.73 (d, 1H), 7.45 (d, 1H), 7.20 (dd, 1H), 7.15 (s, 1H), 5.05 (d, 1H), 4.98 (d, 1H), 4.10 (m, 1H), 4.03 (m, 3H), 3.68 (dd, 1H), 3.42 (dd, 1H), 3.33 (dd, 1H), 3.23 (dd, 1H).

EXAMPLE 7

5-Chloro-1H-indole-2-carboxylic acid [2-(4-hydroxy-piperidin-1-yl)-2-oxo-ethyl]-amide 4-Hydroxypiperidine (0.83 mmol) and [(5-chloro-1H-indole-2-carbonyl)-amino]-acetic acid (0.8 mmol) were coupled according to procedure A (dimethylformamide-dichloromethane reaction solvent) with the following workup: the reaction mixture was stirred with ethyl acetate and aqueous 2 N HCl, the resulting suspension filtered and the collected solid washed successively with aqueous 2 N HCl, aqueous 2 N NaOH, ether and dried: Yield 180 mg, 68%; TSPMS 336/338 (MH+, 100%);

$^1$H NMR (DMSO-$d_6$) δ11.84 (br, 1H), 8.68 (br, 1H), 7.71 (d, 11H), 7.43 (d, 1H), 7.17 (dd, 1H), 7.14 (s, 1H), 4.80 (br, 1H), 4.15 (m, 2H), 3.91 (m, 1H), 3.72 (m, 2H), 3.20 (m, 1H), 3.05 (m, 1H), 1.75 (m, 2H), 1.48 (m, 1H), 1.38 (m, 1H).

EXAMPLE 8

5-Chloro-1H-indole-2-carboxylic acid [1-benzyl-2-(3-hydroxy-pyrrolidin-1-yl)-2-oxo-ethyl]-amide Racemic3-pyrrolidinol (2.0 mmol) and 2-[(5-chloro-1H-indole-2-carbonyl)-amino]-3phenyl-propionic acid (1 mmol) were coupled according to procedure A (0–25° C. reaction temperature, washing first with acid then base), and the product purified by column chromatography on silica gel eluted with 0.5–16% ethanol in dichloromethane to give a colorless foam: Yield 260 mg, 63%; HPLC (60/40) 100%, 3.86 minutes; PBMS 412/414 (MH+, 100%);

Anal. Calcd for $C_{22}H_{22}ClN_3O_3$+0.2 $H_2O$: C, 63.60; H, 5.43; N, 10.11.

Found: C, 63.90; H, 5.93; N, 10.11.

EXAMPLE 9

5-Chloro-1H-indole-2-carboxylic acid (1-diethylcarbamoyl-2-phenyl-ethyl)-amide

Diethylamine(1.2 mmol) and 2-[(5-chloro-1H-indol-2-carbonyl)-amino]3-phenyl-propionic acid (0.6 mmol) were coupled according to procedure A (0–25° C. for 5 days) substituting the following workup: the crude product was suspended in 1:1 chloroform/dichloromethane, sonicated, filtered to remove solids, concentrated, and the residue purified by column chromatography on silica gel eluted with 10, 20 and 30% ethyl acetate in hexanes: Yield 14 mg, 6%; HPLC (60/40) 8.88 minutes (98%); PBMS 398/400 (MH+, 100%);

$^1$H NMR (CDCl$_3$) δ9.31 (br, 1H), 7.61 (d, 1H), 7.32 (d, 1H, J=8.7 Hz), 7.28–7.18 (m, 7H), 6.87 (d, 1H, J=1.4 Hz), 5.26 (m, 1H), 3.6 (m, 1–1.5H), 3.2–2.9 (m, 4.5–5H), 1.07 (t, 3H, J=7.2 Hz), 1.02 (t, 3H, J=7.2 Hz).

Anal. Calcd for $C_{22}H_{24}ClN_3O_2+0.25\ H_2O$: C, 65.66; H, 6.14; N, 10.44.

Found: C, 65.61; H, 6.20; N, 10.11.

EXAMPLE 10

4-{2-[(5-Chloro-1H-indole-2-carbonyl)-amino]-3-phenyl-propionyl}-piperazine-1-carboxylic acid tert-butyl ester 1-Piperazinecarboxylic acid t-butyl ester (1.2 mmol) and 2-[(5chloro-1H-indole-2-carbonyl)-amino]-3-phenyl-propionic acid (0.6 mmol) were coupled according to procedure A (0–25° C. reaction temperature, reaction time 4 days, extraction with acid first, then base), and the crude product purified by column chromatography on silica gel eluted with 30% ethyl acetate in hexanes to give a colorless foam: Yield 290 mg, 95%; HPLC (70/30) 6.23 min (99%); PBMS 512/514 (MH+, 100%);

$^1$H NMR (CDCl$_3$) δ9.32 (br, 1H), 7.60 (d, 1H, J=1.9 Hz), 7.32 (d, 1H, J=8.7 Hz), 7.3–7.15 (m, ca. 7H), 6.87 (d, 1H, J=1.5 Hz), 5.33 (m, 1H), 3.65–2.9 (overlapping m, 9H), 2.70 (m, 1H), 1.43 (s, 9H).

Anal. Calcd for $C_{27}H_{31}ClN_4O_4$: C, 63.46; H, 6.11; N, 10.96.

Found: C, 63.33; H, 5.97; N, 10.97.

EXAMPLE 11

5-Chloro-1H-indole-2-carboxylic acid [1-benzyl-2-(4-methylamino-piperidin-1-yl)-2-oxo-ethyl]-amide Dimethylamine hydrochloride (1.1 mmol), sodium acetate (2.1 mmol), activated 3A molecular seives, and sodium cyanoborohydride (0.25 mmol) were added in this order to 5-chloro-1H-indole-2-carboxylic acid [1-benzyl-2-oxo-2-(4-oxo-piperidin-1-yl)-ethyl]-amide (0.21 mmol) in methanol (2 mL) at 0° C. After 18 hours, the mixture was concentrated, the residue taken up in ethyl acetate, the resulting solution washed with 2N NaOH and brine, dried with Na$_2$SO$_4$ and concentrated. The product was purified by chromatography on silica gel eluted with 1–8% ethanol in dichloromethane containing 0.5 % NH$_4$OH followed by trituration with ether: Yield 82%; HPLC (60/40) 2.79 minutes (98%); PBMS 439/441 (MH+,100%);

$^1$H NMR (DMSO-d$_6$) δ11.75 (br, 1H), 8.94 (d, 0.5H, J=8.8 Hz), 8.90 (d, 0.5H), 7.71 (d, 1H, J=1.8 Hz), 7.40 (d, 1H, J=8.7 Hz), 7.31–7.20 (m, 6–7H), 7.17 (dd, 1H, J=2.1, 8.7 Hz), 5.15 (m, 1H), 4.22 (m, 0.5H), 4.08 (m, 0.5H), 3.96 (m, 0.5H), 3.85 (m, 0.5H), 3.2–2.9 (m,4H), 2.78 (m, 0.5H), 2.72 (m, 0.5H), 2.25 (s, 1.5H), 2.24 (s, 1.5H), 1.75 (m, 2H), 1.3–0.8 (m, 2H).

Anal. Calcd for $C_{24}H_{27}ClN_4O_2+1.0\ H_2O$: C, 63.08; H, 6.40; N, 12.26.

Found: C, 63.18; H, 6.16; N, 12.46.

EXAMPLE 12

5-Chloro-1H-indole-2-carboxylic acid (1-benzyl-2-morpholin-4-yl-2-oxo-ethyl)-amide Morpholine (0.33 mmol) and 2-[(5chloro-1H-indole-2-carbonyl)-amino]-3-phenyl-propionic acid (0.30 mmol) were coupled according to Procedure A (0–25° C. reaction temperature, 48 hour reaction time). The crude product was chromatographed on silica gel eluted with 1:1 ethyl acetate/hexanes, the desired fractions concentrated, the residue dissolved in chloroform and methanol and the resulting solution stirred 18 hours with approx. 128 mg dimethylaminopyridine-polystyrene resin (Fluka Chemical Co.). The solution was filtered, concentrated and the residue triturated with ether: Yield, 51%; HPLC (60/40) 5.92 min (98%);

PBMS 412/414 (MH+,100%);

$^1$H NMR (DMSO-d$_6$) δ11.75 (br, 1H), 8.95 (d, 1H), 7.72 (d, 1H), 7.39 (d, 1H, J=8.7 Hz), 7.35–7.15 (m, 7H), 5.13 (m, 1H), 3.65–3.10 (m, 8H), 3.05 (m, 2H).

Anal. Calcd for $C_{22}H_{22}ClN_3O_3+0.33H_2O$: C, 63.23; H, 5.47; N, 10.06.

Found: C, 63.28; H, 5.32; N, 10.10.

EXAMPLE 13

5-Chloro-1H-indole-2-carboxylic acid (1-butylcarbamoyl-2-phenyl-ethyl)-amide n-Butyl amine (0.66 mmol) and 2-[(5-chloro-1H-indole-2-carbonyl)-amino]-3-phenyl-propionic acid (0.60 mmol) were coupled according to procedure A (0–25° C. reaction temperature). The crude product was dissolved in chloroform and methanol and the resulting solution stirred 18 hours with 50 mg dimethylaminopyridine-polystyrene resin (Fluka Chemical Co.), the solution filtered, concentrated and the solids triturated with ether: Yield 83%; HPLC (60/40) 8.88 minutes (92%); mp 192–193° C.; TSPMS 398/400 (MH+,100%);

$^1$H NMR (DMSO-d$_6$) δ11.71 (br, 1H), 8.70 (d, 1H, J=8.3 Hz), 8.10 (t, 1H), 7.72 (d, 1H, J=2.0 Hz), 7.39 (d, 1H, J=8.7 Hz), 7.35–7.15 (m, 7H), 4.70 (m, 1H), 3.13–2.93 (m, 4H), 1.38 (m, 2H), 1.25 (m, 2H), 0.86 (t, 3H, J=7.2 Hz);

Anal. Calcd for $C_{22}H_{24}ClN_3O_2$: C, 66.41; H, 6.08; N, 10.56.

Found: C, 66.15; H, 6.04; N, 10.52.

EXAMPLE 14

5-Chloro-1H-indole-2-carboxylic acid [1-benzyl-2-oxo-2-(4-oxo-piperidin-1-yl)-ethyl]-amide 4-Piperidone monohydrate (2.0 mmol) and 2-[(5-chloro-1H-indole-2-carbonyl)-amino]-3-phenyl-propionic acid (1.0 mmol) were coupled according to procedure A (0–25° C. reaction temperature) substituting the following workup: the reaction mixture was diluted with ethyl acetate, the resulting solution washed with 2 N NaOH and 2 N HCl, the suspension filtered and the solids dried: Yield 111 mg, 26%; HPLC (60/40) 8.88 minutes (92%); PBMS 424/426 (MH+, 100%); mp 258–261° C.; PBMS 424/426 (MH+, 100%);

$^1$H NMR (DMSO-d$_6$) δ11.75 (br, 1H), 9.03 (d, 1H, J=8.1 Hz), 7.72 (d, 1H, J=1.9 Hz), 7.39 (d, 1H, J=8.7 Hz), 7.4–7.15 (m, 7H), 5.20 (m, 1H, J=8.2 Hz), 3.88 (m, 1H), 3.73 (m, 3H), 3.1 (m, 3H), 2.5–2.22 (m, 3H), 2.05 (m, 1H).

Anal. Calcd for $C_{23}H_{22}ClN_3O_3+0.75\ H_2O$: C, 63.16; H, 5.42; N, 9.61.

Found: C, 63.11; H, 5.15; N, 9.53.

EXAMPLE 15

5-Chloro-1H-indole-2-carboxylic acid (1-benzyl-2-oxo-2-pyrrolidin-1-yl-ethyl)-amide Pyrrolidine (0.35 mmol) and 2-[(5-chloro-1H-indole-2-carbonyl)-amino]-3-phenyl-propionic acid (0.31 mmol)

were coupled according to procedure A (0–25° C. reaction temperature, 140 hour reaction time) and the crude product triturated with ether: Yield 89 mg, 71%; HPLC (70/30) 7.57 minutes (98%); PBMS 396/398 (MH+, 100/80%);

Anal. Calcd for $C_{22}H_{22}ClN_3O_2+0.33 H_2O$: C, 65.75; H, 5.68; N, 10.48.

Found: C, 65.56; H, 5.81; N, 10.44.

EXAMPLE 16

5-Chloro-1H-indole-2-carboxylic acid {1-[(3-dimethylamino-propyl)methyl-carbamoyl]-2-phenyl-ethyl}-amide N,N,N'-Trimethyl-1,3-diaminopropane (0.31 mmol) and 2-[(5-chloro-1H-indole-2-carbonyl)-amino]-3-phenyl-propionic acid (0.28 mmol) were coupled according to Procedure A (0–25° C. reaction temperature, 120 hour reaction time) and the product purified by chromatography on silica gel eluted with 1–8% ethanol in dichloromethane containing 0.5% ammonium hydroxide: Yield 86 mg, 69%; HPLC (40/60) 7.57 minutes (>99%); mp 187–190.5° C.; TSPMS 441/443 (MH+, 100%);

Anal. Calcd for $C_{24}H_{29}ClN_4O_2+0.25 H_2O$: C, 64.71; H, 6.68; N, 12.58.

Found: C, 64.73; H, 6.94; N, 12.86.

EXAMPLE 17

5-Chloro-1H-indole-2-carboxylic acid [1-(3-morpholin-4-yl-propylcarbamoyl)-2-phenyl-ethyl]-amide 4-(3Aminopropyl)morpholine (0.34 mmol) and 2-[(5-chloro-1H-indole-2-carbonyl)-amino]-3-phenyl-propionic acid (0.30 mmol) were coupled according to Procedure A (0–25° C. reaction temperature) substituting the following workup: the reaction was diluted with ethyl acetate, the resulting solution washed three times with 2 N NaOH and once with brine, dried over $Na_2SO_4$, and concentrated. The residue was stirred under ether for 1 hour, the solid filtered and dried: Yield 125 mg, 87%; HPLC (60/40) 2.85 minutes (98%); PBMS 469/471 (MH+, 100/90%);

Anal. Calcd for $C_{25}H_{29}ClN_4O_3+0.25 H_2O$: C, 63.42; H, 6.28; N, 11.83.

Found: C, 63.31; H, 6.57; N, 12.04.

EXAMPLE 18

5-Chloro-1H-indole-2-carboxylic acid (1-dimethylcarbamoyl-2-phenyl-ethyl)-amide

Dimethylamine hydrochloride (0.96 mmol) and 2-[(5-chloro-1H-indole-2-carbonyl)-amino]-3-phenyl-propionic acid (0.90 mmol) were coupled according to Procedure A (0–25° C. reaction temperature, 60 hour reaction time, washed first with acid, then base), and the resulting solid triturated with ether: Yield 320 mg, 99%; HPLC (60/40) 5.87 minutes (100%);

mp 224–225° C.; PBMS 370/372 (MH+, 100%).

A sample was recrystallized from hot ethyl acetate for analysis (mp 224–225° C.).

Anal. Calcd for $C_{20}H_{20}ClN_3O_2+0.5 C_4H_8O_2$: C, 63.80; H, 5.84; N, 10.15.

Found: C, 63.81; H, 5.80; N, 10.21.

EXAMPLE 19

5-Chloro-1H-indole-2-carboxylic acid [2-((3R,4R)-dihydroxy-pyrrolidin-1-yl)-2-oxo-ethyl]-amide (3R,4R)-3,4-dihydroxypyrrolidine (from unnatural tartaric acid by the procedure described in U.S. Pat. No. 4,634,775, 1.0 mmol) and [(5-chloro-1H-indole-2-carbonyl)-amino]-acetic acid (1.1 mmol) were coupled according to Procedure A (dimethyl-formamide reaction solvent) substituting the following workup: the reaction mixture was concentrated, diluted with 20 mL ethyl acetate and 20 mL 2 N NaOH, the suspension stirred 0.5 hours, filtered, and the resulting solids washed successively with 2N NaOH, water, 1N HCl and ethyl acetate: Yield 77%; HPLC (40/60) 10.7 minutes (99%); TSPMS 338/340 (MH+, 100%);

$^1$H NMR (DMSO-$d_6$) δ11.84 (br, 1H, exchanges), 8.72 (t, 1H, exchanges), 7.72 (d, 1H, J=1.9 Hz), 7.44 (d, 1H, J=8.7 Hz), 7.19 (dd, 1H, J=2.1, 8.8 Hz), 7.16 (s, 1H), 5.26 (d, 1H, J=4.4 Hz, exchanges), 5.17 (d, 1H, J=3.2 Hz, exchanges), 4.04 (m, 3H), 3.92 (m, 1H), 3.66 (dd, 1H, J=4.0, 10.8 Hz), 3.42–3.28 (m, 3H);

Anal. Calcd for $C_{15}H_{16}ClN_3O_4+0.25 H_2O$: C, 52.64; H, 4.86; N, 12.28.

Found: C, 52.61; H, 4.85; N, 12.23.

EXAMPLE 20

5-Chloro-1H-indole-2-carboxylic acid [2-((3S,4S)-dihydroxy-pyrrolidin-1-yl)-2-oxo-ethyl]-amide (3S,4S)-3,4-Dihydroxypyrrolidine (from naturally occurring tartaric acid by the procedure described in U.S. Pat. No. 4,634,775, 1.0 mmol) and [(5-chloro-1H-indole-2-carbonyl)-amino]-acetic acid (1.0 mmol) were coupled according to Procedure A (dimethylformamide reaction solvent) substituting the following workup: the reaction was diluted with ethyl acetate and 2N NaOH, the resulting suspension filtered, the solids washed with ethyl acetate, water and dried: Yield 135 mg, 40%; HPLC (40/60) 7.29 minutes (98%); TSPMS 338/340 (MH+, 100%);

$^1$H NMR (DMSO-$d_6$) δ12.1 (br, 1H), 8.86 (br, 1H), 7.71 (d, 1H, J=2 Hz), 7.43 (d, 1H, J=8.8 Hz), 7.17 (dd, 1H, J=2, 8.8 Hz), 7.13 (s, 1H), 5.35 (br, 1H, exchanges with $D_2O$), 5.28 (br, 1H, exchanges with $D_2O$), 4.03 (m, 3H), 3.92 (s, 1H), 3.66 (dd, 1H, J=4, 11 Hz), 3.4–3.2 (m, 3H).

Anal. Calcd for $C_{15}H_{16}ClN_3O_4+1.5 H_2O$: C, 49.39; H, 5.25; N, 11.52.

Found: C, 49.50; H, 5.04; N, 11.27.

EXAMPLE 21

5-Chloro-1H-indole-2-carboxylic acid [1-benzyl-2-(4-methoxymethoxy-piperidin-1-yl)-2-oxo-ethyl]-amide 4-Methoxymethoxy-piperidine (1.0 mmol) and 2-[(5-chloro-1H-indole-2carbonyl)-amino]-3-phenyl-propionic acid (1.0 mmol) were coupled according to Procedure A and the product purified by chromatography on silica gel eluted with 1:1 ethyl acetate-hexanes:

Yield 241 mg, 50%; HPLC (60/40) 7.67 minutes (94%); PBMS 470/472 (MH+, 100%);

Anal. Calcd for $C_{25}H_{28}ClN_3O_4$: C, 63.89; H, 6.01; N, 8.94.

Found: C, 63.91; H, 6.00; N, 8.95.

EXAMPLE 22

5-Chloro-1H-indole-2-carboxylic acid [2-phenyl-1-(2,2,6,6-tetramethyl-piperidin-4-ylcarbamoyl)-ethyl]-amide 2,2,6,6-Tetramethyl-piperidine (1.0 mmol) and 2-[(5-chloro-1H-indole-2-carbonyl)-amino]-3-phenyl-propionic acid (1.0 mmol) were coupled according to Procedure A. The resulting yellow foam was triturated with ether, 1:5 dichloromethane-ether. The resulting solid was dissolved in dichloromethane and the resulting solution treated with 0.20 mL 4 N HCl in dioxane. A precipitate formed which was filtered, washed with dichloromethane and dried: Yield 220 mg, 42%; HPLC (60/40) 3.19 minutes (96%);

PBMS 481/483 (MH+, 100%);

Anal. Calcd for $C_{27}H_{33}ClN_4O_2$+HCl+1.5 $H_2O$: C, 59.56; H, 6.85; N, 10.29.

Found: C, 59.30; H, 6.90; N, 10.22.

EXAMPLE 23

(1-{2-[(5-Chloro-1H-indole-2-carbonyl)-amino]-3-phenyl-propionyl}-pyrrolidin-(3RS)-yl)-carbamic acid tert-butyl ester Racemic Pyrrolidine-3-carbamic acid tert-butyl ester (1.0 mmol) and 2-[(5-chloro-1H-indole-2-carbonyl)-amino]-3-phenyl-propionic acid (1.0 mmol) were coupled according to Procedure A and the product purified by chromatography on silica gel eluted with 1:1 ethyl acetate-hexanes: Yield 302 mg, 59%; PBMS 511/513 (MH+, 100%);

Anal. Calcd for $C_{27}H_{31}ClN_4O_4$: C, 63.46; H, 6.11; N, 10.96.

Found: C, 63.32; H, 6.26; N, 10.89.

EXAMPLE 24

5-Chloro-1H-indole-2-carboxylic acid (2-morpholin-4-yl-2-oxo-ethyl)-amide

Morpholine (1.0 mmol) and [(5-chloro-1H-indole-2-carbonyl)-amino]-acetic acid (1.0 mmol) were coupled according to Procedure A. The resulting solid was suspended in ether, filtered and dried to give a beige solid: Yield, 264 mg, 71%; HPLC (60/40) 3.28 minutes (100%); TSPMS 322/324 (MH+, 100%);

$^1$H NMR (DMSO-$d_6$) δ11.85 (s, 1H), 8.68 (t, 1H), 7.72 (d, 1H, J=2.0 Hz), 7.43 (d, 1H, J=8.8 Hz), 7.19 (dd, 1H, J=2.1, 8.8 Hz), 7.16 (s, 1H), 4.17 (d, 2H, J=5.7 Hz), 3.65–3.45 (m, 8H).

Anal. Calcd for $C_{15}H_{16}ClN_3O_3$+0.25 $H_2O$: C, 55.22; H, 5.10; N, 12.88.

Found: C, 55.22; H, 5.08; N, 12.82.

EXAMPLE 25

5-Chloro-1H-indole-2-carboxylic acid [(methoxy-methyl-carbamoyl)-methyl]-amide

Methoxymethylamine hydrochloride (1.0 mmol) and [(5-chloro-1H-indole-2-carbonyl)-amino]-acetic acid (1.0 mmol) were coupled according to Procedure A. The resulting solid was suspended in ether, filtered and dried: Yield 158 mg, 53%; PBMS 296/298 (MH+, 100%);

$^1$H NMR (DMSO-$d_6$) δ11.82 (s, 1H), 8.77 (t, 1H, J=6 Hz), 7.73 (d, 1H, J=2.0 Hz), 7.43 (d, 1H, J=8.7 Hz), 7.19 (dd, 1H, J=2.0, 8.7 Hz), 7.16 (s, 1H), 4.22 (d, 2H, J=5.7 Hz), 3.76 (s, 3H), 3.14 (s, 3H).

Anal. Calcd for $C_{13}H_{14}ClN_3O_3$: C, 52.80; H, 4.77; N, 14.21.

Found: C, 52.51; H, 4.82; N, 14.01.

EXAMPLE 26

5-Chloro-1H-indole-2-carboxylic acid [1-benzyl-2-(4-dimethylamino-piperidin-1-yl)-2-oxo-ethyl]-amide 4-Dimethylaminopiperidine (1.0 mmol) and 2-[(5-chloro-1H-indole-2-carbonyl)-amino]-3-phenyl-propionic acid (1.0 mmol) were coupled according to Procedure A. The residue was purified by chromatography on silica gel eluted with 5–30% ethanol in dichloromethane containing 0.5% ammonium hydroxide, followed by trituration with ether: Yield 21 mg, 5%; PBMS 453/455 (MH+, 100%);

$^1$H NMR (DMSO-$d_6$, partial) δ11.75 (br, 1H), 8.94 (m, 1H), 7.72 (d, 1H, J=2 Hz), 7.45–7.10 (m, 8H), 5.17 (m, 1H), 4.63 (m), 4.38 (m), 4.03 (m), 3.50 (m), 3.15–2.8 (m), 2.51 (s, 3H), 2.50 (s, 3H).

EXAMPLE 27

5-Chloro-1H-indole-2-carboxylic acid (1-benzyl-2-oxo-2-piperazin-1-yl-ethyl)-amide Trifluoroacetic acid (4 ml) was added to 4-{2-[(5-chloro-1H-indole-2-carbonyl)-amino]-3-phenyl-propionyl}-piperazine-1-carboxylic acid tert-butyl ester (0.6 mmol) at 0° C. and the resulting solution was stirred for 0.3 hours and concentrated. The residue was partitioned between ethyl acetate and 2 N NaOH, the organic layer separated and washed with brine, dried over $Na_2SO_4$, concentrated and the resulting solid triturated with ether: Yield 189 mg, 77%; HPLC (60/40) 2.63 minutes (99%);

mp 166.5–168° C.; TSPMS 411/413 (MH+, 100%);

Anal. Calcd for $C_{22}H_{23}ClN_4O_2$+0.5 $H_2O$: C, 62.93; H, 5.76; N, 13.34.

Found: C, 62.64; H, 5.52; N, 13.34.

EXAMPLE 28

5-Chloro-1H-indole-2-carboxylic acid [2-((3RS)-amino-pyrrolidin-1-yl)-1-benzyl-2-oxo-ethyl]-amide 4N HCl in 1,4-dioxane (5 ml) was added to (1-{2-[(5-chloro-1H-indole-2-carbonyl)-amino]-3-phenyl-propionyl}-pyrrolidin-(3RS-yl)-carbamic acid tert-butyl ester (0.5 mmol). The resulting solution was stirred at 25° C. for 0.5 hours, concentrated and the residue triturated with ether: Yield 190 mg, 85%; HPLC (60/40) 2.62 minutes (98%); PBMS 411/413 (MH+, 100%);

Anal. Calcd for $C_{22}H_{23}ClN_4O_2$+HCl+1.7 $H_2O$: C, 55.28; H, 5.78; N, 11.72.

Found: C, 55.14; H, 5.86; N, 11.45.

EXAMPLE 29

1-{(2RS)-[(5-Chloro-1H-indole-2-carbonyl)-amino]-3-phenyl-propionyl}-pyrrolidine-(2S)-carboxylic acid Trifluoroacetic acid was added to 1-{2(RS)-[(5-chloro-1H-indole-2-carbonyl)-amino]-3-phenyl-propionyl}-pyrrolidine-(2S)-carboxylic acid tert-butyl ester (1.0 mmol) at 25° C. After 1.5 hours, the reaction was concentrated and the residue triturated first with ether then with a mixture of ether and hexanes. Yield 360 mg, 82%; HPLC (60/40) 4.84 minutes (99%); PBMS 440/442 (MH+, 40%), 396/398 (MH−44, 100%);

Anal. Calcd for $C_{23}H_{22}ClN_3O_4$+0.8 $H_2O$: C, 60.81; H, 5.24; N, 9.25.

Found: C, 60.74; H, 5.42; N, 8.96.

EXAMPLE 29a

1-{(R,S)-[(5-chloro-1H-indole-2-carbonyl)-amino]3-phenyl-propionyl}-pyrrolidine-(2S)-carboxylic acid tert-butyl ester L-Proline-t-butyl ester (2.0 mmol) and 2-[(5-chloro-1H-indole-2-carbonyl)-amino]-3-phenyl-propionic acid (2.0 mmol) were coupled according to Procedure A and the crude product purified by chromatography on silica gel eluting with 1:2 ethyl acetate-hexanes: Yield 611 mg, 62%; HPLC (60/40) 13.45 minutes (57%) and 14.48 minutes (41%).

EXAMPLE 30

5Chloro-1H-indole-2-carboxylic acid ((1S)-methylcarbamoyl-2-thiazol-4-yl-ethyl)-amide (S)-2-Amino-N-methyl-3-thiazol-4-yl-propionamide hydrochloride (0.6 mmol) and 5-chloro-1H-indole-2-carboxylic acid (0.51 mmol) were coupled according to Procedure A (0–25° C. reaction temperature, reaction solvent dimethyl-formamide). The crude product was stirred in ether for 0.5 hours then filtered giving a beige solid: 182 mg, 98%; HPLC (60/40) 3.41 minutes (98%); mp >260° C. (dec); TSPMS 363/365 (MH+, 100%);

$^1$H NMR (DMSO-$d_6$) δ11.82 (br, 1H), 9.0 (d, 1H), 8.82 (br, 1H), 8.10 (br, 1H), 7.70 (m, 1H), 7.44–7.38 (m, 2H), 7.21–7.15 (m, 2H), 4.80 (m, 1H), 3.24 (m, 1H), 3.05 (m, 1H), 2.60 (d, 3H).

EXAMPLE 30a (S)-2-Amino-N-methyl-3-thiazol-4-yl-propionamide hydrochloride (S)-(1-Methylcarbamoyl-2-thiazol-4-yl-ethyl)-carbamic acid tert-butyl ester (248 mg, 0.87 mmol) was dissolved in 4 M HCl-dioxane at 0° C. The resulting mixture was stirred for 1 hour at 25° C., concentrated and the residue triturated with ether. Yield, 202 g, 102%; HPLC (70/30) 2.41 minutes (96%);

EXAMPLE 30b (S)-2-(N-t-Butoxycarbonylamino)-N-methyl-3-thiazol-4-yl-propionamide Methylamine hydrochloride (1.2 mmol) and Boc-L-3-(4-thiazolyl)alanine (1.0 mmol) were coupled according to Procedure A (0–25° C. reaction temperature, acid wash omitted) and the product used without further purification. Yield, 250 mg, 88%.

EXAMPLE 31

(±)-[(5-Chloro-1H-indole-2-carbonyl)-amino]-3-hydroxy-propionic acid methyl ester D,L-Serine methyl ester hydrochloride (2.1 mmol) and 5-chloro-1H-indole-2-carboxylic acid (2.0 mmol) were coupled according to Procedure A (0–25° C. reaction temperature, washed with acid first then with saturated NaHCO$_3$) and the product purified by chromatography on silica gel eluted with 10, 20, 40 and 60% ethyl acetate in hexanes: Yield 565 mg, 95%; HPLC (60/40) 3.46 minutes (98%); mp 153–155 ° C.; TSPMS 297/299 (MH+, 100/40%);

Anal. Calcd for $C_{13}H_{13}ClN_2O_4$: C, 52.62; H, 4.42; N, 9.44.

Found: C, 52.62; H, 4.54; N, 9.53.

EXAMPLE 32

5-Chloro-1H-indole-2-carboxylic acid ((1S)-dimethylcarbamoyl-2-thiazol-4-yl-ethyl)-amide (S)-2-Amino-N,N-dimethyl-3-thiazol-4-yl-propionamidehydrochlodide(0.43mmol) and 5-chloro-1H-indole-2-carboxylic acid (0.40 mmol) were coupled according to Procedure A (0–25° C. reaction temperature) and the crude product triturated first with 1:1 ether-hexanes, then with hexanes. Yield 115 mg, 75%; HPLC (60/40) 3.72 minutes (99%); mp 198–202° C. (shrinks on insertion at 192° C.); PBMS 377/379 (MH+, 100%);

$^1$H NMR (DMSO-$d_6$) δ11.75 (s, 1H), 9.02 (d, 1H, J=2 Hz), 8.9 (d, 1H, J=8.2 Hz), 7.7 (d, 1H, J=1.8 Hz), 7.41 (d, 1H, J=6.7 Hz), 7.39 (s, 1H), 7.22 (s, 1H), 7.17 (dd, 1H, J=2.2, 8.7 Hz), 5.30 (m, 1H), 3.24 (dd, A of AB, 1H, J=7, 13 Hz), 3.16 (dd, B of AB, 1H, J=8.5, 16 Hz), 3.07 (s, 3H), 2.84 (s, 3H).

Anal. Calcd for $C_{17}H_{17}ClN_4O_2S+0.125\ H_2O$: C, 53.86; H, 4.59; N, 14.78.

Found: C, 53.92; H, 4.47; N, 14.42.

EXAMPLE 32a (S)-2-Amino-N,N-dimethyl-3-thiazol-4-yl-propionamide hydrochloride (S)-(1-Dimethylcarbamoyl-2-thiazol-4-yl-ethyl)-carbamic acid tert-butyl ester was dissolved in 4M HCl-dioxanes at 0° C. and stirred at 25° C. for 2 hours. The mixture was concentrated and the residue triturated with ether. Yield, 3.06 g, 105%; HPLC (70/30) 2.12 minutes (97%); PBMS 200 (MH+, 100%).

EXAMPLE 32b (S)-(1-Dimethylcarbamoyl-2-thiazol-4-yl-ethyl)-carbamic acid tert-butyl ester Dimethylamine hydrochloride (1.2 mmol) and Boc-L-3-(4-thiazolyl)alanine (1.0 mmol) were coupled according to Procedure A (0–25° C. reaction temperature) and the product purified by chromatography on silica gel eluted with 1–16% ethanol In dichloromethane containing 0.5% ammonium hydroxide. Yield 124 mg, 41%.

EXAMPLE 33

5-Chloro-1H-indole-2-carboxylic acid [(1S)-benzyl-2-((3R,4S)-dihydroxy-pyrrolidin-1-yl)-2-oxo-ethyl]-amide (3R, 4S)-Dihydroxypyrrolidine hydrochloride (0.5 mmol) and 5-chloro-1H-indole-2-carboxylic acid (0.5 mmol) were coupled according to Procedure A and the product purified by chromatography on silica gel eluted with 2–10% ethanol in dichloromethane. Yield 180 mg, 86%; HPLC (60/40) 3.14 minutes (98%); TSPMS 428/430 (MH+, 100%);

$^1$H NMR (DMSO-$d_6$) δ11.75 (br, 1H), 8.94 (d, 1H, J=8 Hz), 7:72 (s, 1H), 7.4–7.1 (m, 8H), 5.03 (d, 0.5H, J=5 Hz), 4.95 (d, 0.5H, J=5 Hz), 4.90 (d, 1H, J=5 Hz), 4.87 (m, 1H), 4.08 (m, 0.5H), 4.00 (m, 0.5H), 3.88 (m, 1.5H), 3.5–3.3 (m, 2.5H), 3.2 (m, 0.5H), 3.0 (m, 2H).

Anal. Calcd for $C_{22}H_{22}ClN_3O_4+0.25\ H_2O$: C, 61.11; H, 5.25; N, 9.72.

Found: C, 60.91; H, 5.46; N, 9.43.

EXAMPLE 33a (Cis-3,4-)-Dihydroxyopyrrolidine hydrochloride

Cis-3,4-Dihyohoxy-pyrrolidine-1-carboxylic acid tert-butyl ester (1.99 g, 9.8 mmol) was dissolved in 4M HCl-dioxane at 5° C. and the resulting suspension stirred at 25° C. for 1 hour. The mixture was concentrated and the residue triturated with ether giving a light purple powder (1.30 g, 95%).

EXAMPLE 33b

Cis-3,4-Dihydroxy-pyrrolidine-1-carboxylic acid tert-butyl ester

A solution of crude 2,5-dihydro-pyrrole-1-carboxylic acid tert-butyl ester (10.5 g, 62.1 mmol) in tetrahydro-furan (300 ml) was treated sequentially with osmium tetroxide (2.5% in t-butanol, 6 mL) and N-methylmorpholine-N-oxide at 25° C. After 48 hours, aqueous 10% sodium thiosulfate solution was added and the mixture was stirred 30 minutes, partially concentrated to remove tetrahydro-furan, and the resulting aqueous mixture extracted twice with ether. The ether extracts were washed with 10% sodium thiosulfate, 0.1 N HCl, dried and concentrated giving a dark orange oil which was chromatographed on silica eluted with 1%, 2%, 4%, 8% and 10% ethanol-dichloromethane giving an amber syrup (4.09 g).

EXAMPLE 33c

2,5-Dihydro-pyrrole-1-carboxylic acid tert-butyl ester

Di-t-butyldicarbonate (83 g, 380 mmol) was added to a solution of 3-pyrroline (containing 35% pyrrolidine, 25 g, 362 mmol) in tetrahydrofuran (500 mL) at 0° C. The mixture was stirred at 25° C. for 1 hour and concentrated giving 76.2 g of a yellow oil which was used without purification.

EXAMPLE 34

(3S)-[(5-Chloro-1H-indole-2-carbonyl)-amino]-4-(4-hydroxy-piperidin-1-yl)-4-oxo-butyric acid tert-butyl ester (S)-3-Amino-4-(4-hydroxy-piperindin-1-yl)-4-oxo-butyric acid tert-butyl ester (0.8 mmol) and 5-chloro-1H-indole-2-carboxylic acid (0.8 mmol) were coupled according to Procedure A and the product purified by chromatography on silica gel eluted with 25, 40, 50, 75 and 100% ethyl acetate in hexanes. Yield 330 mg, 94%; HPLC (60/40) 4.18 minutes (97%); TSPMS 450/452 (MH+, 100%).

EXAMPLE 34a

(S)-3-Amino-4-(4-hydroxy-piperidin-1-yl)-4-oxo-butyric acid tert-butyl ester Diethylamine (1.0 mmol) was added to (S)-3-(9H-fluoren-9-ylmethoxycarbonyl-amino)-4-(4-hydroxy-piperidin-1-yl)-4-oxo-butyric acid tert-butyl ester in dimethyl-formamide (5 ml) at 25° C. After 1 hour, the reaction mixture was concentrated, the residue suspended in 1:1 ether/dichloromethane, filtered and concentrated. The residue was purified by chromatography on silica gel eluted with 1–50% ethanol in dichloromethane containing 0.5% ammonium hydroxide. Yield 217 mg, 80%.

EXAMPLE 34b

(S)-3-(9H-Fluoren-9-ylmethoxycarbonylamino)-4-(4-hydroxy-piperidin-1-yl)-4-oxo-butyric acid 4-Hydroxypiperidine (2.1 mmol) and N-FMOC-L-aspartic acid-β-t-butyl ester (2.0 mmol) were coupled according to Procedure A (96 hour reaction time, washed with acid only) and the product purified by chromatography on silica gel eluted with 1–4 % ethanol in dichloromethane. Yield 516 mg, 52%; HPLC (60/40) 5.33 minutes (93 %).

EXAMPLE 35

5-Chloro-1H-indole-2-carboxylic acid [(1R)-benzyl-2-(4-hydroxy-piperidin-1-yl-2-oxo-ethyl]-amide (R)-2-Amino-1-4-hydroxy-piperidin-1-yl)phenyl-propan-1-one hydrochloride (3.1 mmol) and 5-chloro-1H-indole-2-carboxylic acid (3.4 mmol) were coupled according to Procedure A (0–25° C. reaction temperature, 60 hour reaction time) and the product purified by chromatography on silica gel eluted with 50, 75 and 100% ethyl acetate in hexanes followed by trituration wit 1:1 ether-hexanes. Yield 1.1 g, 84%; HPLC (60/40) 4.06 minutes (99%); PBMS 426/428 (MH+, 100%);

Anal. Calcd for $C_{23}H_{24}ClN_3O_3 + 0.25\ H_2O$: C, 64.18; H, 5.74; N, 9.76.

Found: C, 64.28; H, 5.94; N, 9.41.

EXAMPLE 35a

(R)-2-Amino-1-(4-hydroxy-piperidin-1-yl)-3-phenyl-propan-1-one hydrochloride (R)-2-(N-t-butoxycarbonylamino)-1-(4-hydroxy-piperidin-1-yl)-3-phenyl-propan-1-one (12.5 mmol) was dissolved in 4M HCl-dioxane at 0° C. and the resulting suspension stirred at 25° C. for 1 hour. The mixture was concentrated and the residue triturated with ether. Yield, 3.44 g, 97%.

EXAMPLE 35b

(R)-2-(N-t-butoxycarbonylamino)-1-(4-hydroxy-piperidin-1-yl)-3-phenyl-propan-1-one (R)-2-(N-t-butoxycarbonylamino)-3-phenyl-propan-1-one (14 mmol) and 4-hydroxypiperidine (21.5 mmol) were coupled according to Procedure A (0–25° C. reaction temperature, washed with acid first then base) and the product used without further purification. Yield 4.7 g, 94%; HPLC (60/40) 3.52 minutes (98%).

EXAMPLE 36

1H-indole-2-carboxylic acid [2-(1,1-dioxo-1-thiazolidin-3-yl)-2-oxo-ethyl]-amide 2-Amino-1(1,1-dioxo-1-thiazolidin-3-yl)-ethanone hydrochloride (1.0 mmol) and 1H-indole-2-carboxylic acid (1.0 mmol) were coupled according to Procedure A (0–25° C. reaction temperature, 60 hour reaction time) with the following workup: the reaction mixture was diluted with ethyl acetate and 2 N NaOH, the resulting precipitate was collected and washed with 2N NaOH, 1 N HCl and water. Yield 135 mg, 42%; HPLC (60/40) 2.97 minutes (97%); PBMS 322 (MH+, 100%);

Anal. Calcd for $C_{14}H_{15}N_3O_4S + 0.25\ H_2O$: C, 51.60; H, 4.79; N, 12.90.

Found: C, 51.31; H, 4.66; N, 12.88.

EXAMPLE 36a

2-Amino-1-(1,1-dioxo-1-thiazolidin-3-yl)-ethanone hydrochloride

[2-(1,1-Dioxo-1-thiazolidin-3-yl)-2-oxo-ethyl]-carbamic acid tert-butyl ester (11 mmol) was dissolved in 4M HCl-dioxane at 0° C. and the resulting suspension stirred at 25° C. for 1 hour. The mixture was concentrated and the residue triturated with ether. Yield, 2.3 g, 100%.

EXAMPLE 36b

[2-(1,1-Dioxo-1-thiazolidin-3-yl)-2-oxo-ethyl]-carbamic acid tert-butyl ester m-Chloroperoxybenzoic acid (35 mmol) was added slowly to (2-oxo-2-thiazolidin-3yl-ethyl)-carbamic acid tert-butyl ester (14 mmol) in dichloromethane (35 ml) at 0° C. After foaming subsided, the mixture was stirred an additional 2.5 hours at 25° C. The mixture was diluted with ethyl acetate, the resulting solution washed three times with a 1:1 mixture of saturated aqueous $NaHCO_3$ and 10% aqueous $NaS_2O_3$ solution, once with saturated $NaHCO_3$, dried, concentrated and the residue triturated with 1:1 ether/hexanes. Yield, 3.6 g, 92%.

EXAMPLE 36c (2-Oxo-2-thiazolidin-3-yl-ethyl)-carbamic acid tert-butyl ester

Thiazolidine (85 mmol) and Boc-glycine (57 mmol) were coupled according to Procedure A (0–25° C. reaction temperature, 60 hour reaction time) and the product used without purification. Yield 12.7 g, 90%.

EXAMPLE 37

5-Fluoro-1H-indole-2-carboxylic acid [(1S)-benzyl-2-(4-hydroxy-piperidin-1-yl)-2-oxo-ethyl]-amide (S)-2-Amino-1-(4-hydroxy-piperidin-1-yl)-3-phenyl-propan-1-one hydrochloride (0.65 mmol) and 5-fluoro-1H-indole-2-carboxylic acid (0.73 mmol) were coupled according to Procedure A (0–25° C. reaction temperature) and the product purified by chromatography on silica gel eluted with 20, 30, 40, 50, 75 and 100% ethyl acetate in hexanes. Yield 228 mg, 84%; HPLC (60/40) 3.57 minutes (98%); PBMS 410 (MH+, 100%);

Anal. Calcd for $C_{23}H_{24}FN_3O_3 + 0.25\ H_2O$: C, 66.73; H, 5.97; N, 10.15.

Found: C, 66.68; H, 6.19; N, 9.94.

EXAMPLE 38

1H-indole-2-carboxylic acid [(1S)-benzyl-2-(4-hydroxy-piperidin-1-yl)-2-oxo-ethyl]-amide (S)-2-Amino-1-(4-hydroxy-piperdin-1-yl)-3-phenyl-propan-1-one hydrochloride (3.4 mmol) and 1H-indole-2-carboxylic acid (3.7 mmol) were coupled according to Procedure A (0–25° C. reaction temperature, 48 hour reaction time). The product was purified by chromatography on silica gel eluted with 50, 75 and 100% ethyl acetate in hexanes, followed by trituration with 1:1 ether-hexanes. Yield 1.14 g, 88%; HPLC (60/40) 3.52 minutes (98%); PBMS 392 (MH+, 100%);

Anal. Calcd for $C_{23}H_{25}N_3O_3 + 0.25\ H_2O$: C, 69.77; H, 6.49; N, 10.61.

Found: C, 69.99; H, 6.72; N, 10.47.

EXAMPLE 39

5-Fluoro-1H-indole-2-carboxylic acid [(1S)-(4-fluoro-benzyl)-2-morpholin-4-yl-2-oxo-ethyl]-amide (S)-2-Amino-3-(4-fluoro-phenyl)-1-morpholin-4-yl-propan-1-one hydrochloride (0.48 mmol) and 5-fluoro-1H-indole-2-carboxylic acid (0.48 mmol) were coupled according to Procedure A (0–25° C. reaction temperature, 48 hour reaction time, washed with acid first then base) and the product purified by chromatography on silica gel eluted with 20, 30, 40, 50 and 75% ethyl acetate in hexanes. Yield 189 mg, 95%; HPLC (60/40) 4.76 minutes (97%); PBMS 414 (MH+, 100%);

$^1$H NMR (CDCl$_3$) δ9.23 (br, 1H), 7.4–7.1 (m, 5H), 7.1–6.94 (m, 3H), 6.9 (d, 1H, J=2 Hz), 5.30 (m, 1H), 3.72–3.48 (m, 5H), 3.42 (m, 1H), 3.03 (m, 4H).

Anal. Calcd for $C_{22}H_{21}F_2N_3O_3$: C, 63.92; H, 5.12; N, 10.16.

Found: C, 64.30; H, 5.34; N, 9.82.

EXAMPLE 39a (S)-2-Amino-3-(4-fluoro-phenyl)-1-morpholin-4-yl-propan-1-one hydrochloride (S)-2-(N-t-Butoxycarbonylamino)-3-(4-fluoro-phenyl)-1-morpholin-4-yl-propan-1-one (3.1 mmol) was dissolved in 4M HCl-dioxane at 0° C. and the resulting suspension stirred at 25° C. for 1 hour. The mixture was concentrated and the residue triturated with ether. Yield, 776 mg, 88%; HPLC (60/40) 2.31 minutes (99%).

EXAMPLE 39b (S)-2-(N-t-Butoxycarbonylamino)-3-(4-fluoro-phenyl)-1-morpholin4-yl-propan-1-one Morpholine (3.7 mmol) and (S)-Boc-4-fluoro-phenyl-alanine (3.5 mmol) were coupled according to Procedure A (0–25° C. reaction temperature, 60 hour reaction time, washed first with acid, then base) and the product purified by chromatography on silica gel eluted with 20, 30 and 40% ethyl acetate in hexanes. Yield 1.08 g oil, 87%.

EXAMPLE 40

5-Fluoro-1H-indole-2-carboxylic acid [(1S)-benzyl-2-(1,1-dioxo-1-thiazolidin-3-yl)-2-oxo-ethyl]-amide (S)-2-Amino-1-(1,1-dioxo-1-thiazolidin-3-yl)-3-phenyl-propan-1-one hydrochloride (1.0 mmol) and 5-fluoro-1H-indole-2-carboxylic acid (1.0 mmol) were coupled according to Procedure A (0–25° C. reaction temperature, reaction time 48 hour, washed with acid first, then base) and the product purified by chromatography on silica gel eluted with 20, 30, 40 and 50% ethyl acetate in hexanes. Yield 404 mg, 94%; HPLC (60/40) 4.74 min (98%); PBMS 430 (MH+, 100%);

$^1$H NMR (CDCl$_3$) δ9.53 (br, 0.5H), 9.44 (br, 0.5H), 7.44 (d, 0.5H, J=9 Hz), 7.4–7.1 (m, 7H), 7.02 (M, 1H), 6.84 (s, 0.5H), 6.81 (s, 0.5H), 5.20 (m, 0.5H), 4.96 (m, 0.5H), 4.68 (d, 0.5H, J=11 Hz), 4.52 (d, A of AB, 0.5H, J=11.5 Hz), 4.37 (d, B of AB, 0.5H, J=11.5 Hz), 4.20 (m, 0.5H), 4.03 (m, 0.5H), 3.80 (m, 0.5H), 3.50 (d, 0.5H, J=11 Hz), 3.3–3.0 (m, 4H), 2.69 (m, 0.5H).

EXAMPLE 40a (S)-2-Amino-1-(1,1-dioxo-1-thiazolidin-3-yl)-3-phenyl-propan-1-one hydrochloride (S)-2-(N-t-Butoxycarbonylamino)-1-(1,1-dioxo-1-thiazolidin-3-yl)-3-phenyl-propan-1-one was dissolved in 4M HCl-dioxanes at 0° C. The solution was stirred at 25° C. for 1 hour, concentrated and the residue triturated with ether. Yield, 866 mg, 84%.

EXAMPLE 40b (S)-2-(N-t-Butoxycarbonylamino)-1-(1,1-dioxo-1-thiazolidin-3-yl)-3-phenyl-propan-1-one A solution of m-chloroperoxybenzoic acid (9 mmol) and (S)-(1-benzyl-2-oxo-2-thiazolidin-3-yl-ethyl)-carbamic acid-tert-butyl ester (3 mmol) in dichloromethane (9 ml) were heated at reflux for 6 hours. The mixture was diluted with ethyl acetate, the resulting solution washed three times with a 1:1 mixture of 10% aqueous $NaS_2O_3$ and saturated aqueous $NaHCO_3$, dried and concentrated. The resulting foam was purified by chromatography on silica gel eluted with 20, 30 and 40% ethyl acetate in hexanes giving a colorless foam (979 mg, 89% yield).

EXAMPLE 40c (S)-(1-Benzyl-2-oxo-2-thiazolidin-3-yl-ethyl)-carbamic acid tert-butyl ester Thiazolidine (38 mmol) and Boc-L-phenylalanine (19 mmol) were coupled according to Procedure A (0–25° C. reaction temperature, washed with acid then base) and the product used without further purification. Yield 5.5 g, 86%.

EXAMPLE 41

5-Fluoro-1H-indole-2-carboxylic acid [2-(1,1-dioxo-1-thiazolidin-3-yl)-2-oxo-ethyl]-amide 2-Amino-1-(1,1-dioxo-1-thiazolidin-3-yl)-ethanone hydrochloride (1.0 mmol) and 5-fluoro-1H-indole-2-carboxylic acid (1.0 mmol) were coupled according to Procedure A (0–25° C. reaction temperature, 48 hour reaction time) with the following workup. The reaction mixture was diluted with ethyl acetate and 1 N HCl, the resulting suspension was filtered and the collected solid washed with 2 N HCl, 2 N NaOH and water. The filtered solid was boiled in acetone, filtered and dried. Yield 134 mg, 40%; HPLC (60/40) 3.06 minutes (97%); mp 239–241° C. (with discoloration); PBMS 340 (MH+, 70%), 357 (100%)

$^1$H NMR (DMSO-$d_6$) δ11.74 (s, 1H), 8.82 (m, 1H), 7.43 (m, 2H), 7.17 (s, 1H), 7.05 (dt, 1H, J=3, 9 Hz), 4.86 (s, 1.2H), 4.52 (s, 0.8H), 4.27 (d, 0.8H, J=5.5 Hz), 4.13 (d, 1.2H, J=6 Hz, superimposed on m, 1.2H), 3.86 (t, 1.2H, J=7.4 Hz), 3.58 (t, 0.8H, J=7 Hz), 3.46 (t, 1.2H, J=7.2 Hz).

Anal. Calcd for $C_{14}H_{14}FN_3O_4S+0.6$ $H_2O$: C, 48.02; H, 4.38; N, 12.00.

Found: C, 47.99; H, 4.04; N, 12.00.

EXAMPLE 42

5-Cyano-1H-indole-2-carboxylic acid ((1S)-benzyl-2-oxo-2-thiazolidin-3-yl-ethyl)-amide (S)-2-Amino-3-phenyl-1-thiazolidin-3-yl-propan-1-one hydrochloride (4.0 mmol) and 5-cyano-1H-indole-2-carboxylic acid (4.0 mmol) were coupled according to Procedure A (0–25° C. reaction temperature, 48 hours reaction time) with the following workup: the reaction mixture was diluted with ethyl acetate and 2 N HCl, the resulting precipitate collected by filtration, washed with 2 N HCl and 2 N NaOH. The crude product was purified by chromatography on silica gel eluted with 30, 40 and 60% ethyl acetate in hexanes. Yield 1.22 g, 75%; HPLC (60/40) 4.74 minutes (97%); PBMS 405 (MH+, 100%);

Anal. Calcd for $C_{22}H_{20}N_4O_2S+0.5$ $H_2O$: C, 63.90; H, 5.12; N, 13.55.

Found: C, 64.18; H, 5.04; N, 13.47.

EXAMPLE 42a (S)-2-Amino-3-phenyl-1-thiazolidin-3-yl-propan-1-one hydrochloride (S)-(1-Benzyl-2-oxo-2-thiazolidin-3-yl-ethyl)-carbamic acid tert-butyl ester (16 mmol) was dissolved in 4 M HCl-dioxanes at 0° C., the solution stirred at 25° C. for 1 hour, the reaction concentrated and the residue triturated with ether. Yield, 4.2 g, 95 %.

EXAMPLE 42b

5-Cyano-1H-indole-2-carboxylic acid

5-Cyano-1H-indole-2-carboxylic acid ethyl ester (1.71 g, 8.0 mmol) was added to a solution of ethanol (10 mL) and potassium hydroxide (2 g) and the resulting mixture heated at reflux for 1 hour. Water was added to dissolve the precipitate, and 6 N HCl was added to bring the pH to 1. A precipitate formed. The mixture was cooled in an ice bath, filtered, and the resulting colorless solid washed with cold water and dried (1.51 g). A portion (1.4 g) was suspended in hot acetic acid (40 mL) and cooled giving a solid which was filtered, washed with cold ethyl acetate and dried: Yield 980 mg (70%); HPLC (60/40) 3.09 minutes (97%).

EXAMPLE 43

1H-indole-2-carboxylic acid [(1S)-benzyl-2-(1,1-dioxo-1-thiazolidin-3-yl)-2oxo-ethyl]-amide (S)-2-Amino-1-(1,1-dioxo-1-thiazolidin-3-yl)-3-phenyl-propan-1-one hydrochloride (0.56 mmol) and 1H-indole-2-carboxylic acid (0.56 mmol) were coupled according to Procedure A (0–25° C. reaction temperature) and the product triturated with 1:1 ether-hexanes. Yield 213 mg, 92%; HPLC (60/40) 4.15 minutes (99%); PBMS 412 (MH+, 100%);

Anal. Calcd for $C_{21}H_{21}N_3O_4S+0.5$ $H_2O$: C, 59.99; H, 5.27; N, 9.99.

Found: C, 60.25; H, 5.27; N, 9.98.

EXAMPLE 44

5-Chloro-1H-indole-2-carboxylic acid [2-(1,1-dioxo-1-thiazolidin-3-yl)-2-oxo-ethyl]-amide 2-Amino-1-(1,1-dioxo-1-thiazolidin-3-yl)-ethanol hydrochloride (0.6 mmol) and 5-chloro-1H-indole-2-carboxylic acid (0.6 mmol) were coupled according to Procedure A (0–25° C. reaction temperature, 120 hour reaction time) with the following work up: the reaction mixture was diluted with ethyl acetate and 2N HCl, the resulting precipitate was collected by filtration followed by washing with 2 N HCl, 2 N NaOH, water and ether. Yield 110 mg, 52%; HPLC (60/40) 3.37 minutes (99%); m.p 236–239° C. (dec); PBMS 356/358 (MH+, 100%);

$^1$H NMR (acetone-$d_6$) δ11.0 (br, 1H), 8.0 (br, 1H), 7.66 (d, 1H, J=2 Hz), 7.55 (d, 1H, J=8.7 Hz), 7.21 (dd, 1H, J=2.0, 8.7 Hz), 7.15 (d, 1H, J=2 Hz), 4.77 (s, 1.1H), 4.49 (s, 0.9H), 4.37 (d, 0.9H, J=5.3 Hz), 4.27 (d, ca. 1H, J=5.3 Hz, superimposed on m, ca. 1H), 4.04 (t, 1.1H, J=7 Hz), 3.54 (t, 0.9H, J=7 Hz), 3.40 (t, 1.1H, J=7 Hz).

Anal. Calcd for $C_{14}H_{14}ClN_3O_4S+1.6$ $H_2O$: C, 43.72; H, 4.51; N, 10.93.

Found: C, 44.05; H, 3.88; N, 10.99.

EXAMPLE 45

5-Chloro-1H-indole-2-carboxylic acid (2-oxo-2-thiazolidin-3-yl-ethyl)-amide

2-Amino-1-thiazolidin-3-yl-ethanone hydrochloride (3.1 mmol) and 5-chloro-1H-indole-2-carboxylic acid (3.4 mmol) were coupled according to Procedure A (0–25° C., 120 hour reaction time) substituting the following work up:

the reaction mixture was stirred with ethyl acetate and 2N HCl, filtered, and the filtered solid washed with 2N HCl, 2N NaOH and ether. Yield 988 mg, 98%; HPLC (70/30) 3.25 minutes (99%); mp 253–255° C. (dec, darkening at 243° C.); PBMS 324/326 (MH+, 100%);

$^1$H NMR (acetone-d$_6$) δ11.03 (br, 1H), 7.88 (br, 1H), 7.66 (d, 1H, J=2 Hz), 7.54 (d, 1H, J=8.3 Hz), 7.21 (dd, 1H, J=2, 8.3 Hz), 4.67 (s, 0.8H), 4.53 (s, 1.2H), 4.24 (m, 2H), 3.87 (t, 1.2H, J=7 Hz), 3.78 (t, 0.8H, J=7 Hz), 3.18 (t, 1.2H, J=7 Hz), 3.05 (t, 0.8H, J=7 Hz).

A sample was recrystallized from acetic acid for analysis (mp 262–264° C.):

Anal. Calcd for C$_{14}$H$_{14}$ClN$_3$O$_2$S: C, 51.93; H, 4.36; N, 12.98.

Found: C, 51.78; H, 4.38; N, 12.95.

EXAMPLE 45a

2-Amino-1thiazolidin-3-yl-ethanol hydrochloride (2-Oxo-2-thiazolidin-3-yl-ethyl)-carbamic acid tert-butyl ester (5.41 g, 22 mmol) was dissolved in 4M HCl-dioxane (80 mL) at 0° C. The resulting solution was stirred at 25° C. for 2 hours, concentrated and the residue triturated with ether. Yield, 3.9 g, 97%.

EXAMPLE 46

5-Chloro-1H-indole-2-carboxylic acid [(1S)-benzyl-2-(4-hydroxy-piperidin-1-yl)-2-oxo-ethyl]-amide (S)-2-Amino-1-(4-hydroxy-piperidin-1-yl)-3-phenyl-propan-1-one hydrochloride (0.8 mmol) and 5-chloro-1H-indole-2-carboxylic acid (0.9 mmol) were coupled according to Procedure A (0–25° C. reaction temperature, 48 hour reaction time) and the product purified by chromatography on silica gel eluted with 50, 75 and 100% ethyl acetate in hexanes followed by trituration from 1:1 ether-hexanes. Yield 266 mg, 76%; HPLC (60/40) 4.09 minutes (99%); PBMS 426/428 (MH+, 100%);

Anal. Calcd for C$_{23}$H$_{24}$ClN$_3$O$_3$+0.33 H$_2$O: C, 63.96; H, 5.76; N, 9.73.

Found: C, 63.90; H, 5.74; N, 9.58.

EXAMPLE 46a (S)-2-Amino-1-(4-hydroxy-piperidin-1-yl)-3-phenyl-propan-1-one hydrochloride (S)-[1-Benzyl-2-(4-hydroxy-piperidin-1-yl)-2-oxo-ethyl]-carbamic acid tert-butyl ester (3.66 g, 10.5 mmol) was dissolved in 4M HCl-dioxane (39 mL) at 0° C. The mixture was stirred at 25° C. for 1 hour, concentrated and the residue triturated with ether. Yield 3.06 g, 102%.

EXAMPLE 46b (S)-[1-Benzyl-2-(4-hydroxy-piperidin-1-yl)-2-oxo-ethyl]-carbamic acid tert-butyl ester 4-Hydroxypiperidine (75 mmol) and Boc-L-phenylalanine (38 mmol) were coupled according to Procedure A (0–25° C. reaction temperature, 144 hour reaction time) and the product used without further purification. Yield 12.2 g, 96%; HPLC (60/40) 3.45 minutes (97%).

EXAMPLE 47

5-Bromo-1H-indole-2-carboxylic acid [(1S)-benzyl-2-(1,1-dioxo-1-thiazolidin-3-yl)-2-oxo-ethyl]-amide (S)-2-Amino-1-(1,1-dioxo-1-thiazolidin-3-yl)-3-phenyl-propan-1-one hydrochloride (0.3 mmol) and 5-bromo-1H-indole-2-carboxylic acid (0.3 mmol) were coupled according to Procedure A (0–25° C. reaction temperature, washed with acid first, then base) and the product purified by chromatography on silica gel eluted with 30, 40 and 50% ethyl acetate in hexanes. The product was collected as an off-white foam and triturated with 1:1 ether-hexanes to give 107 mg, 73%; HPLC (60/40) 6.21 minutes (99%); PBMS 490/492 (MH+, 100%);

$^1$H NMR (CDCl$_3$) δ9.53 (br, 0.5H), 9.44 (br, 0.5H), 7.78 (d, 0.5H, J=2 Hz), 7.76 (d, 0.5H, J=2 Hz), 7.4–7.2 (m, 7H), 7.10 (d, 0.5H, J=9 Hz), 7.02 (d, 0.5H, J=9 Hz), 6.86 (s, 0.5H), 6.81 (s, 0.5H), 5.21 (m, 0.5H), 4.95 (m, 0.5H), 4.62 (d, 0.5H, J=11 Hz), 4.47 (d, A of AB, 0.5H, J=13 Hz), 4.38 (d, B of AB, 0.5H, J=13 Hz), 4.20 (m, 0.5H), 4.03 (m, 0.5H), 3.82 (m, 0.5H), 3.44 (d, 0.5H, J=11 Hz), 3.33–3.0 (m, 4H), 2.70 (m, 0.5H).

Anal. Calcd for C$_{21}$H$_{20}$BrN$_3$O$_4$S+0.2 H$_2$O: C, 51.06; H, 4.16; N, 8.51.

Found: C, 51.44; H, 4.36; N, 7.93.

EXAMPLE 48

5-Chloro-1H-indole -2-carboxylic acid [(1S)-benzyl-2-oxo-2-(3-oxo-pyrrolidin-1-yl)-ethyl]-amide (S)-1-(2-Amino-3-phenyl-propionyl)-pyrrolidin-3-one hydrochloride (0.6 mmol) and 5-chloro-1H-indole-2-carboxylic acid (0.6 mmol) were coupled according to Procedure A (0–25° C. reaction temperature, washed with acid first, then base) and the product purified by chromatography on silica gel eluted with 40 and 50% ethyl acetate in hexanes, followed by trituration of the resulting foam with ether. Yield 112 mg, 45%; HPLC (60/40) 5.13 minutes (>99%); PBMS 410/412 (MH+, 100%);

$^1$H NMR (CDCl$_3$) δ9.19 (m, 1H), 7.60 (m, 1H), 7.3–7.15 (m, 8H), 6.86 (m, 1H), 4.23 (m, 0.5H), 4.95 (m, 0.5H), 4.0–3.7 (m, 3H), 3.27 (m, 1H), 3.15 (m, 1H), 3.05 (m, 0.5H), 2.85 (d, 0.5H, J=28 Hz), 2.45 (m, 1.5H), 2.15 (m, 0.5H).

Anal. Calcd for C$_{22}$H$_{20}$ClN$_3$O$_3$+0.55 H$_2$O: C, 62.95; H, 5.07; N, 10.01.

Found: C, 63.31; H, 5.09; N, 9.61.

EXAMPLE 48a (S)-1-(2-Amino-3-phenyl-propionyl)-pyrrolidin-3-one hydrochloride (S)-[1-Benzyl-2-oxo-2-(3-oxo-pyrrolidin-1-yl)-ethyl]-carbamic acid tert-butyl ester (552 mg, 1.7 mmol) was dissolved in 4M HCl-dioxane (6.2 mL) at 0° C. The mixture was stirred at 25° C. for 1 hour, concentrated and the residue triturated with ether to give alight brown solid. Yield, 482 mg, 108%.

EXAMPLE 48b (S)-[1-Benzyl-2-oxo-2-(3-oxo-pyrrolidin-1-yl)-ethyl]-carbamic acid tert-butyl ester A solution of dimethyl sulfoxide (4.07 g, 52 mmol) and oxalyl chloride (3.61 g, 28 mmol) were added slowly in that order to dichloromethane (50 ml) at −78° C. (S)-[1-Benzyl-2-(3-hydroxy-pyrrolidin-1-yl)-2-oxo-ethyl]-carbamic acid tert-butyl ester (24 mmol) in dichloromethane (30 ml) was added to the above solution via canula, the reaction temperature brought to −30° C. for 0.5 hours, then lowered to −78° C. followed by the additon of triethylamine (118 mmol). The reaction was then warmed to 25° C., diluted with ethyl acetate, washed three times with 1:1 saturated NaHCO₃/brine, the organics dried over MgSO₄ and concentrated. The resulting foam was purified by chromatography on silica gel eluted with 30, 40 and 50% ethyl acetate in hexanes to give a light yellow foam (7.5 g, 95% yield).

EXAMPLE 48c (S)-[1-Benzyl-2-(3RS)-hydroxy-pyrrolidin-1-yl)-2-oxo-ethyl]-carbamic acid tert-butyl ester (±)-3-Pyrrolidinol (75 mmol) and Boc-L-phenylalanine (38 mmol) were coupled according to Procedure A (0–25° C. reaction temperature, washed with acid first, then base) and the product used without further purification. Yield 12.2 g, 96%; HPLC (60/40) 3.45 minutes (96%).

EXAMPLE 49

5-Chloro-1H-indole-2-carboxylic acid ((1S)-benzyl-2-oxo-2-thiazolidin-3-yl-ethyl)-amide (S)-2-Amino-3-phenyl-1-thiazolidin-3-yl-propan-1-one hydrochloride (2.6 mmol) and 5-chloro-1H-indole-2-carboxylic acid (2.6 mmol) were coupled according to Procedure A (0–25° C. reaction temperature, 96 hour reaction time, washed with acid first then base). The crude product was triturated with 1:1 ether-hexanes and dried. Yield 966 mg, 91%; HPLC (60/40) 7.99 minutes (97%); PBMS 414/416 (MH+, 100%);

$^1$H NMR (CDCl₃) δ9.26 (br, 1H), 7.59 (m, 1H), 7.35–7.20 (m, 8H), 6.84 (m, 1H), 5.14 (m, 1H), 4.61 (d, A of AB, 0.6H, J=10.3 Hz), 4.52 (d, 0.4H, J=11.6 Hz), 4.42 (d, B of AB, 0.6H, J=10.3 Hz), 3.88 (m, 0.4H), 3.80–3.65 (m, ca 1.5H), 3.2 (m, ca 2.5H) 3.04 (m, 0.4H), 2.95–2.8 (m, 1.2H), 2.63 (m, 0.6H).

Anal. Calcd for C₂₁H₂₀ClN₃O₂S+0.6 H₂O: C, 59.39; H, 5.03; N, 9.89.

Found: C, 59.39; H, 4.96; N, 9.52.

EXAMPLE 50

5-Chloro-1H-indole-2-carboxylic acid ((1S)-benzyl-2-oxo-2-thiomorpholin-4-yl-ethyl)-amide (S)-2-Amino-3-phenyl-1-thiomorpholin-4-yl-propan-1-one hydrochloride (2.6 mmol) and 5-chloro-1H-indole-2-carboxylic acid (2.6 mmol) were coupled according to Procedure A (0–25° C. reaction temperature, washed with acid first, then base). The crude product was then triturated with 1:1 ether-hexanes and dried. Yield 1.03 g, 94%; HPLC (60/40) 8.74 minutes (99%); PBMS 428/430 (MH+, 100%);

Anal. Calcd for C₂₂H₂₂ClN₃O₂S: C, 61.75; H, 5.18; N, 9.82. Found: C, 62.04; H, 5.58; N, 9.72.

EXAMPLE 50a (S)-2-Amino-3-phenyl-1-thiomorpholin-4-yl-propan-1-one hydrochloride (S)-(1-Benzyl-2-oxo-2-thiomorpholin-4-yl-ethyl)-carbamic acid tert-butyl ester (17.8 mmol) was dissolved in 4M HCl-dioxane (67 mL) at 0° C., the solution stirred at 25° C. for 1 hour, the reaction concentrated and the residue triturated with ether. Yield, 5.0 g, 98%; PBMS 251 (MH+, 100%).

EXAMPLE 50b (S)-(1-Benzyl-2-oxo-2-thiomorpholin-4-yl-ethyl)-carbamic acid tert-butyl ester Thiomorpholine (38 mmol) and Boc-L-phenylalanine (19 mmol) were coupled according to Procedure A (0–25° C. reaction temperature) with the following work up: the reaction mixture was concentrated, diluted with ethyl acetate, then washed first with 1 N HCl three times, then with 2 N NaOH, the organic layer dried over MgSO₄ and concentrated. The resulting foam was used without further purification. Yield 6.3 g, 95%.

EXAMPLE 51

5-Chloro-1H-indole-2-carboxylic acid [(1S)-benzyl-2-(1,1-dioxo-1-thiazolidin-3-yl)-2-oxo-ethyl]-amide (S)-2-Amino-1-(1,1-dioxo-1-thiazolidin-3-yl)-3-phenyl-propan-1-one hydrochloride (0.8 mmol) and 5-chloro-1H-indole-2-carboxylic acid (0.8 mmol) were coupled according to Procedure A (0–25° C. reaction temperature, washed with acid first, then base). The product was purified by chromatography on silica gel eluted with 30, 40 and 50% ethyl acetate in hexanes followed by trituration with 1:1 ether-hexanes. Yield 266 mg, 75%; HPLC (60140) 5.52 minutes (>99%); PBMS 446/448 (MH+, 100%);

$^1$H NMR (CDCl₃) δ9.21 (br, 0.5H), 9.15 (br, 0.5H), 7.62 (br, 0.5H, J=2 Hz), 7.60 (d, 0.5H, J=2 Hz), 7.35–7.20 (m, 7H), 7.10 (d, 0.5H, J=8.5 Hz), 7.02 (d, 0.5H, J=8.5 Hz), 6.84 (d, 0.5H, J=2 Hz), 6.81 (d, 0.5H, J=2 Hz), 5.21 (m, 0.5H), 4.93 (m, 0.5H), 4.62 (d, 0.5H, J=11 Hz), 4.47 (d, A of AB, 0.5H, J=13 Hz), 4.39 (d, B of AB, 0.5H, J=13 Hz), 4.22 (m, 0.5H), 4.03 (m, 0.5H), 3.83 (m, 0.5H), 3.44 (d, 0.5H, J=11Hz), 3.3–3.0 (m, 4H), 2.67 (m, 0.5H).

EXAMPLE 52

5-Chloro-1H-indole-2-carboxylic acid [(1S)-4-chloro-benzyl)-2-(4-hydroxy-piperidin-1-yl)-2-oxo-ethyl]-amide (S)-2-Amino-3-(4-chloro-phenyl)-1-(4-hydroxy-piperidin-1-yl)-propan-1-one hydrochloride (0.98 mmol) and 5-chloro-1H-indole-2-carboxylic acid (0.92 mmol) were coupled according to Procedure A and the product purified by chromatography on silica gel eluted with 50, 75 and 100% ethyl acetate in hexanes. Yield 362 mg, 86%; HPLC (60/40) 5.06 minutes (97%); m.p 227–229° C.; TSPMS 460/462 (MH+, 100%);

Anal. Calcd for C₂₃H₂₃Cl₂N₃O₃: C, 60.01; H, 5.04; N, 9.13. Found: C, 59.83; H, 5.18; N, 9.16.

EXAMPLE 52a (S)-2-Amino-3-(4-chloro-phenyl)-1-(4-hydroxy-piperidin-1-yl)-propan-1-one hydrochloride (S)-[1-(4-Chloro-benzyl)-2-(4-hydroxy-piperidin-1-yl)-2-oxo-ethyl]-carbamic acid tert-butyl ester (475 mg, 1.2 mmol) was dissolved in 4M HCl-dioxane (5 mL) at 0° C. The mixture was stirred for 1.5 hour at 25° C., concentrated and the residue triturated with ether. Yield, 422 mg, 105%; TSPMS 283 (MH+, 100%).

EXAMPLE 52b (S)-[1-(4-Chloro-benzyl)-2-(4-hydroxy-piperidin-1-yl)-2-oxo-ethyl]-carbamic acid tert-butyl ester 4-Hydroxypiperidine (2.6 mmol) and Boc-L-p-chlorophenylalanine (2.5 mmol) were coupled according to Procedure A and the product purified by chromatography on silica gel eluted with 1:1 and 3:1 ethyl acetate/hexanes. Yield 662 mg, 69%.

EXAMPLE 53

5-Chloro-1H-indole-2-carboxylic acid [2-(4-hydroxy-piperidin-1-yl)-(1S)-(1H-imidazol-4-ylmethyl)-2-oxo-ethyl]-amide (S)-2-Amino-1-(4-hydroxy-piperidin-1-yl)-3-(1H-imidazol-4-yl)-propan-1-one hydrochloride (0.7 mmol) and 5-chloro-1H-indole-2-carboxylic acid (0.7 mmol) were coupled according to Procedure A (120 hour reaction time, acid wash omitted). The crude product was triturated twice with ether, with 1:1 ether-hexanes and the residue purified by chromatography on silica gel eluted with 5–20% ethanol in dichloromethane containing 0.5% ammonium hydroxide. Yield 232 mg, 81%; HPLC (40/60) 2.57 minutes (98%); PBMS 416/418 (MH+, 100%);

Anal. Calcd for $C_{20}H_{22}ClN_5O_3+0.55\ H_2O$: C, 56.42; H, 5.47; N, 16.45.

Found: C, 6.07; H, 5.65; N, 16.08.

EXAMPLE 53a (S)-2-Amino-1-(4-hydroxy-piperidin-1-yl)-3-(1H-imidazol-4-yl)-propan-1-one hydrochloride (S)-{2-(4-Hydroxy-piperidin-1-yl)-2-oxo-1-[1-(toluene-4-sulfonyl)-1H-imidazo-4-ylmethyl]-ethyl}-carbamic acid tert-butyl ester (512 mg, 1.0 mmol) was dissolved in 4 M HCl-dioxane (3 mL) at 0° C. The mixture was stirred at 25° C. for 1.5 hours, concentrated and the residue triturated with ether. Yield, 422 mg, 105%; TSPMS 283 (MH+, 100%).

EXAMPLE 53b (S)-{2-(4-Hydroxy-piperidin-1-yl)-2-oxo-1-[1-(toluene-4-sulfonyl)-1H-imidazol-4-ylmethyl]-ethyl}-carbamic acid tert-butyl ester 4-Hydroxypiperidine (303 mg, 3.0 mmol), triethylamine (394 mg, 3.9 mmol) and diethyl cyanophosphonate (636 mg, 3.9 mmol) were added in that order to Boc-$N_{im}$-tosyl-L-histidine (*J Med Chem* 30 536 (1987); 1.32 g, 3.9 mmol) in dichloromethane (10 ml) at 25° C. After 120 hours, the solution was diluted with ethyl acetate, washed twice with saturated NaHCO₃, dried and concentrated. The residue was purified by chromatography on silica gel eluted with 1–8% ethanol in dichloromethane. Yield, 517 mg, 35%; HPLC (50/50) 4.75 minutes (97%).

EXAMPLE 54

5-Chloro-1H-indole-2-carboxylic acid (2S)-[(5-chloro-1H-indole-2-carbonyl)amino]-3-(4-hydroxy-piperidin-1-yl)-3-oxo-propyl ester (S)-2-Amino-3-hydroxy-1-(4-hydroxy-piperidin-1-yl)-propan-1-one hydrochloride (0.89 mmol) and 5-chloro-1H-indole-2-carboxylic acid (0.85 mmol) were coupled according to Procedure A and the product isolated by chromatography, along with the more polar serine analog (40%) on silica gel eluted with 1–16% ethanol in dichloromethane. Yield 51 mg, 16%; HPLC (60/40) 7.06 minutes (96%); PBMS 348/350 (100%), 543/545 (MH+, <5%).

Anal. Calcd for $C_{26}H_{24}Cl_2N_4O_5+0.57\ H_2O$: C, 56.40; H, 4.58; N, 10.12.

Found: C, 56.79; H, 4.90; N, 9.65.

EXAMPLE 54a (S)-2-Amino-3-hydroxy-1-(4-hydroxy-piperidin-1-yl)-propan-1-one hydrochloride (S)-[1-Hydroxymethyl-2-(4-hydroxy-piperidin-1-yl)-2-oxo-ethyl]-carbamic acid tert-butyl ester (595 mg, 2.0 mmol) was dissolved in 4M HCl-dioxanes (2 mL) at 0° C. The mixture was stirred at 25° C. for 1 hour, concentrated and the residue triturated with ether. Yield, 506 mg, 105%; MS 189 (MH+, 100%).

EXAMPLE 54b (S)-[1-Hydroxymethyl-2-(4-hydroxy-piperidin-1-yl)-2-oxo-ethyl]-carbamic acid tert-butyl ester 4-Hydroxypiperidine (6.7 mmol) and Boc-L-serine (6.4 mmol) were coupled according to Procedure A (60 hour reaction time) with the following workup: the reaction mixture was concentrated, the residue dissolved in chloroform and 1N NaOH (6 mL), and the resulting solution extracted repeatedly (ten or mor times) with chloroform. The chloroform extracts were concentrated and the residue purified by chromatography on silica gel eluted with 1–16% ethanol in dichloromethane. Yield 751 mg, 41%; HPLC (40/60) 2.72 minutes (96%).

EXAMPLE 55

5-Chloro-1H-indole-2-carboxylic acid [(1S)-(4-hydroxy-benzyl)-2-(4-hydroxy-piperidin-1-yl)-2-oxo-ethyl]-amide (S)-2-Amino-3-(4-hydroxy-phenyl)-1-(4-hydroxy-piperidin-1-yl)-propan-1-one hydrochloride (0.68 mmol) and 5-chloro-1H-indole-2-carboxylic acid (0.65 mmol) were coupled according to Procedure A (0–25° C. reaction temperature) with the following workup: the reaction mixture was diluted with ethyl acetate, the resulting solution washed with 1N NaOH (2 ml), the aqueous layer extracted three times with ethyl acetate, the combined organic extracts washed with 1N HCl, dried and concentrated. The residue was purified by chromatography on silica gel eluted with 1–16% ethanol in dichloromethane. Yield, 150 mg, 52%; HPLC (60/40) 3.53 minutes (99%); PBMS 442/444 (MH+, 100%);

Anal. Calcd for $C_{23}H_{24}ClN_3O_4+0.5\ H_2O$: C, 61.26; H, 5.59; N, 9.32.

Found: C, 61.52; H, 5.89; N, 8.98.

EXAMPLE 55a (S)-2-Amino-3-(4-hydroxy-phenyl)1-(4-hydroxy-piperidin-1-yl)-propan-1-one hydrochloride (S)-[1-(4-Hydroxy-benzyl)-2-(4-hydroxy-piperidin-1-yl)-2-oxo-ethyl]-carbamic acid tert-butyl ester (450 mg, 1.2 mmol) was dissolved in 4M HCl-dioxane (2 mL) at 0° C. The mixture was stirred at 25° C. for 1 hour, concentrated and the residue triturated with ether. Yield, 400 mg, 107%; MS 265 (MH+, 100%).

EXAMPLE 55b (S)-[1-(4Hydroxy-benzyl)-2-(4-hydroxy-piperidin-1-yl)-2-oxo-ethyl]-carbamic acid tert-butyl ester 4-Hydroxypiperidine (3.9 mmol) and Boc-L-tyrosine (3.7 mmol) were coupled according to Procedure A (0–25° C. reaction temperature, 60 hour reaction time) with the following workup: the reaction mixture was diluted with ethyl acetate and washed once with base, the base layer was acidified with 2 N HCl and extracted three times with chloroform, and the chloroform extracts concentrated. The resulting foam was purified by chromatography on silica gel eluted with 1–8% ethanol in dichloromethane containing 0.5% NH$_4$OH. Yield 550 mg, 41%; HPLC (40/60) 5.02 minutes (87%).

EXAMPLE 56

5-Chloro-1H-indole-2-carboxylic acid [2-(4-hydroxy-piperidin-1-yl)-2-oxo-(1S)-pyridin-3-ylmethyl-ethyl]-amide (S)-2-Amino-1-(4-hydroxy-piperidin-1-yl)-3-pyridin-3-yl-propan-1-one dihydrochloride (0.8 mmol) and 5-chloro-1H-indole-2-carboxylic acid (0.7 mmol) were coupled according to Procedure A (0–25° C. reaction temperature) and the product purified by chromatography on silica gel eluted with 1–16% ethanol in dichloromethane. Yield 26 mg, 8%; HPLC (50/50) 5.02 minutes (99%); PBMS 427/429 (MH+, 100%);

Anal. Calcd for C$_{22}$H$_{23}$ClN$_4$O$_3$+0.5 H$_2$O: C, 60.62; H, 5.55; N, 12.85.

Found: C, 60.57; H, 5.74; N, 12.53.

EXAMPLE 56a (S)-2-Amino-1-(4-hydroxy-piperidin-1-yl)-3-pyridin-3-yl-propan-1-one dihydrochloride (S)-[2-(4-Hydroxy-piperidin-1-yl)-2-oxo-1-pyridin-3-ylmethyl-ethyl]-carbamic acid-tert-butyl ester (367 mg, 1.05 mmol) was dissolved in 4M HCl-dioxane at 0° C. The resulting suspension was stirred for 1.5 hours at 25° C., concentrated and the residue triturated with ether. Yield, 450 mg, 100%.

EXAMPLE 56b (S)-[2-(4-Hydroxy-piperidin-1-yl)-2-oxo-1-pyridin-3-yl-methyl-ethyl]-carbamic acid-tert-butyl ester 4-Hydroxypiperidine (2.9 mmol) and N-t-Boc-L-3-(3-pyridyl)alanine (2.8 mmol) were coupled according to Procedure A (0–25° C. reaction temperature, 96 hour reaction time, acid wash omitted) and the product purified by chromatography on silica gel eluted with 1–8% ethanol in dichloromethane. Yield 454 mg, 46%; MS 350 (MH+, 100%).

EXAMPLE 57

1H-indole-2-carboxylic acid [(1R)-(4-fluoro-benzyl)-2-(4-hydroxy-piperidin-1-yl)-2-oxo-ethyl]-amide (R)-2-Amino-3-(4-fluoro-phenyl)-1-(4-hydroxy-piperidin-1-yl)-propan-1-one hydrochloride (0.5 mmol) and 1H-indole-2-carboxylic acid (0.5 mmol) were coupled according to Procedure A (0–25° C. reaction temperature) and the product purified by chromatography on silica gel eluted with 25, 30, 50, 75 and 80% ethyl acetate in hexanes. Yield 150 mg, 60%; HPLC (60/40) 3.66 minutes (97%); mp 204–207° C.; PBMS 410 (MH+, 100%);

Anal. Calcd for C$_{23}$H$_{24}$FN$_3$O$_3$: C, 67.47; H, 5.91; N, 10.26.

Found: C, 67.18; H, 6.03; N, 10.21.

EXAMPLE 57a (R)-2-Amino-3-(4-fluoro-phenyl)-1-(4-hydroxy-piperidin-1-yl)-propan-1-one hydrochloride (R)-[1-(4-Fluoro-benzyl)-2-(4-hydroxy-piperidin-1-yl)-2-oxo-ethyl]carbamic acid-tert-butyl ester (2.6 mmol) was dissolved in 4M HCl-dioxane (2 mL) at 0° C. The solution was stirred 2 hours at 25° C., concentrated and the residue triturated with ether. Yield, 920 mg, 124%; HPLC (60/40) 2.23 minutes (98%).

EXAMPLE 57b (R)-[1-(4-Fluoro-benzyl)-2-(4-hydroxy-piperidin-1-yl)-2-oxo-ethyl]-carbamic acid-tert-butyl ester 4-Hydroxypiperidine (3.7 mmol) and (R)-N-t-Boc-p-fluoro-phenylalanine (3.5 mmol) were coupled according to Procedure A giving a foam which was used without further purification. Yield 940 mg, 73%; HPLC (60/40) 3.64 minutes (95%); MS 367 (MH+, 100%).

EXAMPLE 58

5-Chloro-1H-indole-2-carboxylic acid [(1R)-(4-fluoro-benzyl)-2-(4-hydroxy-piperidin-1-yl)-2-oxo-ethyl]-amide (R)-2-Amino-3-(4-fluoro-phenyl)-1-(4-hydroxy-piperidin-1-yl)-propan-1-one hydrochloride (0.6 mmol) and 5-chloro-1H-indole-2-carboxylic acid (0.6 mmol) were coupled according to Procedure A and the crude product purified by chromatography on silica gel eluted with 50, 75 and 100% ethyl acetate in hexanes. Yield 171 mg, 765%; HPLC (60/40) 4.23 minutes (97%); MS 444/446 (MH+, 100%); TSPMS 444/446 (MH+, 100%);

[1] H NMR (CDCl$_3$) δ9.20 (br, 1H), 7.57 (d, 1H, J=2 Hz), 7.33 (d, 1H, J=8 Hz), 7.3–7.2 (m, 2H), 7.14 (m, 2H), 6.97 (m, 2H), 6.85 (m, 1H), 5.34 (m, 1H), 4.05–3.80 (m, 2H), 3.7–3.3 (m, 1.5H), 3.25 (m, 1H), 3.10 (m, 2H), 2.93 (m, 0.5H), 1.9–1.7 (m, 2.5H), 1.45 (m, 2H), 1.15 (m, 0.5H).

Anal. Calcd for C$_{23}$H$_{23}$ClFN$_3$O$_3$+0.05 H$_2$O: C, 62.11; H, 5.23; N, 9.45.

Found: C, 62.51; H, 5.66; N, 9.19.

EXAMPLE 59

5-Fluoro-1H-indole-2-carboxylic acid [(1S)-(4-fluoro-benzyl)-2-(4-hydroxy-piperidin-1-yl)-2-oxo-ethyl]-amide (S)-2-Amino-3-(4-fluoro-phenyl)-1-(4-hydroxy-piperidin-1-yl)-propan-1-one hydrochloride (0.5 mmol) and 5-fluoro-1H-indole-2-carboxylic acid (0.5 mmol) were coupled according to Procedure A. The crude product was triturated once with 1:1 ether-hexanes and once with hexanes. The resulting solid was boiled in ethyl acetate, the resulting suspension filtered, and the collected solid dried. Yield 103 mg, 48%; HPLC (60/40) 3.69 minutes (95%); PBMS 428 (MH+, 100%);

Anal. Calcd for C$_{23}$H$_{23}$F$_2$N$_3$O$_3$+0.25 H$_2$O: C, 63.95; H, 5.48; N, 9.73.

Found: C, 63.93; H, 5.66; N, 9.87.

EXAMPLE 59a (S)-2-Amino-3-(4-fluoro-phenyl)-1-(4-hydroxy-piperidin-1-yl-propan-1-one hydrochloride

[(S)-1-(4-Fluoro-benzyl)-2-(4-hydroxy-piperidin-1-yl)-2-oxo-ethyl]-carbamic acid tert-butyl ester (20.2 g, 55 mmol) was dissolved in 4M HCl-dioxane (25 mL) at 25° C. After 3 hours a thick syrup had precipitated, and an additional 4M HCl-dioxanes (10 mL) was added. The mixture was stirred for 2 hours, concentrated and the solid residue suspended in 4M HCl-dioxanes. After 2 hours at 25° C., the mixture was concentrated and the residue coevaporated twice with ether. The resulting solid was stirred in a mixture of ether (75 mL) and hexanes (10 mL) at 25° C. for 18 hours, the mixture filtered, and the filtered solid washed with 1:1 ether-hexanes and dried giving a hygroscopic solid (16.3 g, 97%).

EXAMPLE 59b

[(S)-1-(4-Fluoro-benzyl)-2-(4-hydroxy-piperidin-1-yl)-2-oxo-ethyl]-carbamic acid tert-butyl ester 4-Hydroxypiperidine (0.29 mol) and (S)-N-t-Boc-p-fluoro-phenylalanine (0.28 mol) were coupled according to Procedure A giving crude product as a foam in 84% yield. A portion of this material (81.6 g) was dissolved in hot ethyl acetate (400 mL) and hexanes (25° C.) was added to the resulting solution until slight turbidity occurred. The mixture was heated to boiling and the resulting clear solution allowed to cool to 25° C. overnight. The resulting suspension was filtered and the collected solid washed with ethyl acetate-hexanes and dried (68.1 g, 67%).

EXAMPLE 60

1-{(2S)-[(5-Chloro-1H-indole-2-carbonyl)-amino]-3-phenyl-propionyl}-(4R)-hydroxy-pyrrolidine-(2S)-carboxylic acid benzyl ester 1-((2S)-Amino-3-phenyl-propionyl)-(4R)-hydroxy-pyrrolidine-(2S)-carboxylic acid benzyl ester hydrochloride (0.56 mmol) and 5-chloro-1H-indole-2-carboxylic acid (0.53 mmol) were coupled according to Procedure A (0–25° C. reaction temperature, 60 hour reaction time) and the product purified by chromatography on silica gel eluted with 20, 30 and 50% ethyl acetate in hexanes. Yield, 26 mg, 8%; HPLC (60/40) 8.14 minutes (98%); PBMS 546/548 (MH+, 100%);

Anal. Calcd for $C_{30}H_{28}ClN_3O_5$: C, 65.99; H, 5.17; N, 7.70.

Found: C, 66.14; H, 5.37; N, 7.60.

EXAMPLE 60a 1-((2S)-Amino-3-phenyl-propionyl)-(4R)-hydroxy-pyrrolidine-(2S)-carboxylic acid benzyl ester hydrochloride 1-((2S)-tert-Butoxycarbonylamino-3-phenyl-propionyl)-(4R)-hydroxy-pyrrolidine-(2S)-carboxylic acid benzyl ester (3.0 mmol) was dissolved in 4M HCl-dioxane at 0° C. The mixture was stirred at 25° C. for 1 hour, concentrated and the residue triturated with ether. Yield 1.16 g, 96%.

EXAMPLE 60b 1-((2S)-tert-Butoxycarbonylamino-3-phenyl-propionyl)-(4R)-hydroxy-pyrrolidine-(2S)-carboxylic acid benzyl ester Trans-L-Hydroxyproline benzyl ester (3.15 mmol) and L-Boc-phenylalanine (3.0 mmol) were coupled according to Procedure A (0–25° C. reaction temperature, 1:1 dichloromethane/dimethylformamide) and the product used without further purification. Yield 1.31 g, 99%; HPLC (60/40) 6.1 minutes (95%).

EXAMPLE 61

5-Chloro-1H-indole-2-carboxylic acid [(1S)-(4-fluoro-benzyl)-2-(4-hydroxy-piperidin-1-yl)-2-oxo-ethyl]-amide (S)-2-Amino-3-(4-fluoro-phenyl)-1-(4-hydroxy-piperidin-1-yl)-propan-1-one hydrochloride (0.051 mol) and 5-chloro-1H-indole-2-carboxylic acid (0.051 mol) were coupled according to Procedure A and the product purified by chromatography on silica gel eluted with 50%, 75%, 80% and 100% ethyl acetate-hexanes giving a foam (yield 78%), HPLC (60/40) 4.21 minutes (99%). A portion of this material was recrystallized by dissolving in hot ethyl acetate (approximately 5–7 mL/g), and adding an approximately equal volume of hexanes at reflux, followed by slow cooling of the solution to 25° C. The solid was filtered and washed with 1:4 ethyl acetate-hexanes and dried (70–90% recovery): mp 175–177° C.;

$^1$H NMR (CDCl$_3$) δ9.41 (m, 0.5H), 9.36 (m, 0.5H), 7.59 (d, 1H, J=2 Hz), 7.37 (d, 1H, J=8 Hz), 7.29 (dd, 1H, J=2, 9 Hz), 7.20 (dd, 1H, J=2.0, 8.9 Hz), 7.14 (m, 2H), 6.95 (m, 2H), 6.86 (m, 1H), 5.34 (m, 1H), 4.05 (m, 0.5H), 3.90 (m, 1.5H), 3.65 (m, 0.5H), 3.45 (m, 1H), 3.25 (m, 1H), 3.10 (m, 2H), 2.93 (m, 0.5H), 1.88 (br, 1H, exchanges with D$_2$O), 1.80 (m, 1.5H), 1.45 (m, 2H), 1.12 (m, 0.5H).

PBMS 444/446 (MH+, 100%);

Anal. Calcd for $C_{23}H_{23}ClFN_3O_3+0.2\ H_2O$: C, 61.73; H, 5.27; N, 9.39.

Found: C, 61.40; H, 5.37; N, 9.11.

EXAMPLE 62

5-Chloro-1H-indole-2-carboxylic acid [(1S)-(methoxy-methyl-carbamoyl)-2-pyridin-3-yl-ethyl]-amide (2S)-Amino-N-methoxy-N-methyl-3-pyridin-3-yl-propionamide dihydrochloride (1.3 mmol) and 5-chloro-1H-indole-2-carboxylic acid (1.25 mmol) were coupled according to Procedure A (0–25° C. reaction temperature, 1:1 dichloromethane/DMF reaction solvent) and the product purified by chromatography on silica gel eluted with ethyl acetate. Yield 313 mg, 65%; HPLC (60/40) 2.84 minutes (99%); TSPMS 387/389 (MH+, 100%);

$^1$H NMR (CDCl$_3$) δ9.1 (br, 1H), 8.48 (dd, 1H), 8.43 (m, 1H), 7.60 (d, 1H), 7.50 (m, 1H, J=ca. 8 Hz), 7.37 (d, 1H, J=ca. 8 Hz), 7.23 (d, 1H), 7.18 (dd, 1H, J=ca. 8 Hz), 7.10 (d, 1H, J=ca. 8 Hz), 6.82 (d, 1H), 5.42 (m, 1H), 3.78 (s, 3H), 3.25 (s, 3H), 3.32 (dd, A of AB, 1H, J=ca. 7, 14 Hz), 3.10 (dd, B of AB, 1H, J=ca. 7, 14 Hz).

Anal. Calcd for $C_{19}H_{19}ClN_4O_3+0.4\ H_2O$: C, 57.91; H, 5.07; N, 14.22.

Found: C, 58.19; H, 5.23; N, 13.82.

EXAMPLE 62a (2S)-Amino-N-methoxy-N-methyl-3-pyridin-3-yl-propionamide dihydrochloride

[(1S)-(Methoxy-methyl-carbamoyl)-2-pyridin-3-yl-ethyl]-carbamic acid tertbutyl ester (1.5 mmol) was dissolved in 4M HCl-dioxane at 0° C. The resulting solution was stirred for 2 hours at 25° C., concentrated and the residue triturated with ether. Yield, 390 mg, 95%.

EXAMPLE 62b (S)-[1-(Methoxy-methyl-carbamoyl)-2-pyridin-3-yl-ethyl]-carbamic acid tert-butyl ester N,O-Dimethylhydroxylamine hydrochloride (1.7 mmol) and Boc-3-pyridyl-L-alanine (1.6 mmol) were coupled according to Procedure A (0–25° C. reaction temperature, 2:1 dichloromethane/dimethylformamide reaction solvent, acid wash omitted, Na$_2$SO$_4$ used for drying). The residue was triturated with ether giving 428 mg (86% yield) of a yellow solid.

EXAMPLE 63

(R,S)-2-[(5-Chloro-1H-indole-2-carbonyl)-amino]-3-(3-fluoro-phenyl)-propionic acid methyl ester (R,S)-2-Amino-3-(3-fluoro-phenyl)-propionic acid methyl ester (2.05 mmol) and 5-chloro-1H-indole-2-carboxylic acid (2.03 mmol) were coupled according to Procedure A (0–25° C. reaction temperature, 1:1 dichloromethane/DMF reaction solvent) and the product purified by chromatography on silica gel eluted with 10, 20 and 40% ethyl acetate in hexanes. The residue was triturated with 1:1 ether-hexanes, and hexanes giving an off-white solid (484 mg, 63%): HPLC (60/40) 8.13 minutes (95%); TSPMS 375/377 (MH+, 100%);

$^1$H NMR (CDCl$_3$) δ9.26 (br, 1H), 7.60 (d, 1H, J=ca. 1 Hz), 7.35 (d, 1H, J=8.7 Hz), 7.25 (m, 2H), 6.95 (m, 1H), 6.91 (m, 1H), 6.84 (m, 1H), 6.77 (d, 1H, J=1.5 Hz), 6.63 (d, 1H, J=7.7 Hz), 5.08 (m, 1H), 3.78 (s, 3H), 3.28 (dd, 1H, A of AB, J=5.7, 14 Hz), 3.21 (dd, 1H, B of AB, J=5.5, 14 Hz).

Anal. Calcd for C$_{19}$H$_{16}$ClFN$_2$O$_3$: C, 60.89; H, 4.30; N, 7.47.

Found: C, 60.79; H, 4.58; N, 7.18.

EXAMPLE 63a (R,S)-2-Amino-3-(3-fluoro-phenyl)-propionic acid methyl ester hydrochloride Trimethylsilylchloride (1.07 g, 9.9 mmol) was added to a suspension of m-fluoro-DL-phenylalanine (0.404 g, 2.2 mmol) in methanol (4 mL) at 25° C. The resulting solution was brought to reflux for 1 hour, cooled and concentrated. The residue was triturated with ether. Yield, 515 mg, 100%; HPLC (60/40) 2.31 minutes (95%).

EXAMPLE 64

5-Chloro-1H-indole-2-carboxylic acid [(1S)-(methoxy-methyl-carbamoyl)-2-thiophen-2-yl-methyl]-amide (S)-2-Amino-N-methoxy-N-methyl-3-thiophen-2-yl-propionamide hydrochloride (1.2 mmol) and 5-chloro-1H-indole-2-carboxylic acid (1.2 mmol) were coupled according to Procedure A (0–25° C. reaction temperature, 2:1 dichloromethane/dimethylformamide reaction solvent). The crude product was purified by chromatography on silica gel eluted with 10, 20, 30 and 40% ethyl acetate in hexanes. Yield 375 mg, 80%; HPLC (60/40) 6.36 minutes (99%); PBMS 392/394 (MH+, 100%);

$^1$H NMR (CDCl$_3$) δ9.33 (br, 1H), 7.60 (d, 1H, J=ca. 1 Hz), 7.30 (d, 1H, J=8.8 Hz), 7.20 (dd, 1H, J=2.0, 8.7 Hz), 7.15 (dd, 1H, J=1, 5.0 Hz), 6.91 (dd, 1H, J=3.4, 5.1 Hz), 6.86 (d, 1H, J=1.6 Hz), 6.84 (d, 1H, J=ca 2 Hz), 5.40 (m, 1H), 3.77 (s, 3H), 3.46 (dd, 1H, A of AB, J=6.2, ca. 14 Hz), 3.37 (dd, 1H, B of AB, J=6.2, ca. 14.2 Hz), 3.25 (s, 3H).

Anal. Calcd for C$_{18}$H$_{18}$ClN$_3$O$_3$S+0.25 C$_4$H$_8$O$_2$: C, 55.14; H, 4.87; N, 10.15.

Found: C, 55.41; H, 4.79; N, 10.17.

EXAMPLE 64a (S)-2-Amino-N-methoxy-N-methyl-3-thiophen-2-yl-propionamide hydrochloride (S)-[1-(Methoxy-methyl-carbamoyl)-2-thiophen-2-yl-ethyl]-carbamic acid tert-butyl ester (1.3 mmol) was dissolved in 4 M HCl-dioxane (1 mL) at 0° C. and the resulting solution stirred at 25° C. for 2 hours. The mixture was concentrated and the residue triturated with ether giving a yellow solid (321 mg, 96%; HPLC (60/40) 2.24 minutes (98%); MS 215 (MH+, 100%).

EXAMPLE 64b (S)-[1-(Methoxy-methyl-carbamoyl)-2-thiophen-2-yl-ethyl]-carbamic acid tert-butyl ester N,O-Dimethylhydroxylamine hydrochloride (1.4 mmol) and Boc-(2-thienyl)-L-alanine (1.3 mmol) were coupled according to Procedure A (0–25° C. reaction temperature) giving the product which was used without further purification. Yield 426 mg, 104%.

EXAMPLE 65

(RS)-2-[(5-Chloro-1H-indole-2-carbonyl)-amino]-3-(4-fluoro-phenyl)-propionic acid methyl ester (R,S)-2-Amino-3-(3-fluoro-phenyl)-propionic acid methyl ester (3.0 mmol) and 5-chloro-1H-indole-2-carboxylic acid (2.9 mmol) were coupled according to Procedure A (0–25° C. reaction temperature, 3:2 dichloromethane/dimethylformamide reaction solvent) and the resulting crude product triturated with 1:1 ether/hexanes. Yield 1.03 g, 92%; HPLC (60/40) 7.95 minutes (96%); PBMS 375/377 (MH+, 100%);

$^1$H NMR (CDCl$_3$) δ9.30 (br, 1H), 7.60 (d, 1H, J=ca. 1 Hz), 7.35 (d, 1H, J=8.8 Hz), 7.25 (dd, 1H, J=2.0, 8.7 Hz), 7.10 (m, 2H), 6.97 (m, 2H), 6.77 (d, 1H, J=2 Hz), 6.62 (d, 1H, J=7.8 Hz), 5.06 (m, 1H), 3.78 (s, 3H), 3.27 (dd, 1H, A of AB, J=7, 14 Hz), 3.19 (dd, 1H, B of AB, J=7, 14 Hz).

Anal. Calcd for C$_{19}$H$_{16}$ClFN$_2$O$_3$: C, 60.89; H, 4.30; N, 7.47.

Found: C, 60.74; H, 4.36; N, 7.55.

EXAMPLE 66

5-Chloro-1H-indole-2-carboxylic acid [2-(4-amino-phenyl)-(1S)-dimethylcarbamoyl-ethyl]-amide hydrochloride (S)-2-Amino-3-(4-amino-phenyl)-N,N-dimethyl-propionamide dihydrochloride (0.7 mmol) and 5-chloro-1H-indole-2-carboxylic acid (0.7 mmol) were coupled according to Procedure A (0–25° C. reaction temperature, 3:1 dichloro-methane/DMF reaction solvent, washed with base only) and the product purified by chromatography on silica gel eluted with 1–16% ethanol in dichloromethane with 0.5% NH$_4$OH. The combined fractions were concentrated, dissolved in methanol at 0° C., the resulting solution treated with 1.01 N HCl (1.05 eq). After 5 minutes, the reaction mixture was concentrated and the residue triturated with ether giving and orange solid (79 mg, 29% yield): TSPMS 385/387 (MH+, 100%);

Anal. Calcd for C$_{20}$H$_{21}$ClN$_4$O$_2$+1.5 HCl: C, 54.65; H, 5.16; N, 12.75.

Found: C, 54.96; H, 5.53; N, 12.53.

EXAMPLE 66a (S)-2-Amino-3-(4-amino-phenyl)-N,N-dimethyl-propionamide dihydrochloride (S)-[2-(4-Amino-phenyl)-1-dimethylcarbamoyl-ethyl]-carbamicacidtert-butyl ester (214 mg, 0.7 mmol) was dissolved in 4M HCl-dioxane (2 mL) at 0° C. and the solution stirred for 2 hours at 25° C. The mixture was concentrated and the residue triturated with ether. Yield, 294 mg, 102%; PBMS 208 (MH+, 100%).

EXAMPLE 66b (S)-[2-(4-Amino-phenyl)-1-dimethylcarbamoyl-ethyl]-carbamic acid tert-butyl ester Dimethylamine hydrochloride (2.04 mmol) and Boc-p-amino-L-phenylalanine (1.7 mmol) were coupled according to Procedure A (0–25° C. reaction temperature, 4:1 dichloromethane/dimethylformamide reaction solvent, washed with base only). The product was purified by chromatography on silica gel eluted with 50, 60, 70 and 100% ethyl acetate in hexanes. Yield 226 mg, 42%; HPLC (70/30) 2.45 minutes (100%).

EXAMPLE 67

5-Chloro-1H-indole-2-carboxylic acid((1S)-dimethylcarbamoyl-3-phenylpropyl)-amide (S)-2-Amino-N,N-dimethyl-4-phenyl-butyramide hydrochloride (0.76 mmol) and 5-chloro-1H-indole-2-carboxylic acid (0.76 mmol) were coupled according to Procedure A (0–25° C. reaction temperature, 3:1 dichloromethane/DMF reaction solvent) and the product purified by chromatography on silica gel eluted with 10, 20, 30, 40, 50 and 60% ethyl acetate in hexanes. Yield 263 mg, 90%; HPLC (60/40) 7.12 minutes (99%);

TSPMS 384/386 (MH+, 100%);

Anal. Calcd for $C_{21}H_{22}ClN_3O_2$: C, 65.71; H, 5.78; N, 10.95,

Found: C, 65.34; H, 5.93; N, 10.91.

EXAMPLE 67a (S)-2-Amino-N,N-dimethyl-4-phenyl-butyramide hydrochloride (S)-(1-Dimethylcarbamoyl-3-phenyl-propyl)-carbamic acid tert-butyl ester (235 mg, 0.8 mmol) was dissolved in 4 M HCl-dioxane (2 mL) at 0° C. The mixture was stirred at 25° C. for 1.5 hours, concentrated and the residue triturated with ether. Yield, 187 mg, 100%; HPLC (60/40) 2.31 minutes (99%).

EXAMPLE 67b (S)-(1-Dimethylcarbamoyl-3-phenyl-propyl)-carbamic acid tert-butyl ester Dimethylamine hydrochloride (1.0 mmol) and (S)-N-t-butoxycarbonyl-2-amino-4-phenylbutyric acid (0.84 mmol) were coupled according to Procedure A (0–25° C. reaction temperature, 3:1 dichloromethane/DMF reaction solvent) giving the product which was used without further purification. Yield 238 mg, 93%; HPLC (60/40) 5.98 minutes (97%).

EXAMPLE 68

5-Chloro-1H-indole-2-carboxylic acid [(1S)-dimethyl-carbamoyl-2-(4-hydroxy-phenyl)-ethyl]-amide (S)-2-Amino-3-(4-hydroxy-phenyl)-N,N-dimethyl-propionamide hydrochloride (1.05 mmol) and 5-chloro-1H-indole-2-carboxylic acid (1.0 mmol) were coupled according to Procedure A (0–25° C. reaction temperature, 2:1 dichloro-methane/DMF reaction solvent, washed with acid only) and the product purified by chromatography on silica gel eluted with 20, 40, 50 and 75% ethyl acetate in hexanes followed by trituration with ether. Yield 400 mg, 104%; HPLC (60/40) 3.93 minutes (98%); mp 228–231° C. (dec, yellowed at 210° C.); TSPMS 386/388 (MH+, 100%);

Anal. Calcd for $C_{20}H_{20}ClN_3O_3+0.9\ H_2O$: C, 59.75; H, 5.47; N, 10.45.

Found: C, 61.05; H, 5.79; N, 10.08.

EXAMPLE 68a (S)-2-Amino-3-(4-hydroxy-phenyl)-N,N-dimethyl-propionamide hydrochloride (S)-[1-Dimethylcarbamoyl-2-(4-hydroxy-phenyl)-ethyl]-carbamic acid tert-butyl ester (5.7 g, 18.5 mmol) was dissolved in 4M HCl-dioxane (7 mL) at 0° C. The mixture was stirred at 25° C. for 3 hours, concentrated and the residue triturated with ether. Yield, 5.23 g; HPLC (60/40) 3.32 minutes (98%).

EXAMPLE 68b (S)-[1-Dimethylcarbamoyl-2-(4-hydroxy-phenyl)-ethyl]-carbamic acid tert-butyl ester Dimethylamine hydrochloride (79 mmol) and Boc-L-tyrosine (66 mmol) were coupled according to Procedure A (0–25° C. reaction temperature, 12:1 dichloromethane/DMF reaction solvent, 60 hour reaction time) and the product purified by chromatography on silica gel eluted with 10, 20, 30, 50 and 70% ethyl acetate in hexanes. Yield 20.6 g, 102%; HPLC (60/40) 3.21 minutes (96%).

EXAMPLE 69

5-Chloro-1H-indole-2-carboxylic acid ((1S)-methoxycarbamoyl-2-phenyl-ethyl)-amide (2S)-Amino-N-methoxy-3-phenyl-propionamide hydrochloride (1.02 mmol) and 5-chloro-1H-indole-2-carboxylic acid (1.02 mmol) were coupled according to Procedure A. The residue was triturated with ether to give a light yellow solid. Yield, 160 mg, 36%; mp 210–213° C. (dec); PBMS 372/374 (MH+, 100%);

Anal. Calcd for $C_{19}H_{18}ClN_3O_3+1.75\ H_2O$: C, 56.58; H, 5.37; N, 10.42.

Found: C, 56.88; H, 5.09; N, 10.03.

EXAMPLE 69a (2S)-Amino-N-methoxy-3-phenyl-propionamide hydrochloride

[(1S)-(Methoxy-carbamoyl)-2-phenyl-ethyl]carbamic acid tert-butyl ester (200 mg, 0.68 mmol) was dissolved in 4 M HCl-dioxane at 0° C. and the mixture stirred at 25° C. After 0.5 hours, the mixture was concentrated and the residue triturated with ether.

EXAMPLE 69b

[(1S)-(Methoxy-carbamoyl)-2-phenyl-ethyl]-carbamic acid tert-butyl ester

Methoxyamine hydrochloride (83.5 mmol) and Boc-L-phenylalanine (20 mmol) were coupled according to Procedure A and the product purified by chromatography on silica gel eluted with 1:1 and 2:1 ethyl acetate/hexanes followed by trituration with ether. Yield 1.80 g, 31%.

EXAMPLE 70

5-Chloro-1H-indole-2-carboxylic acid ((1R)-methylcarbamoyl-2-phenyl-ethyl-amide (R)-2-Amino-N-methyl-3-phenyl-propionamide hydrochloride (0.84 mmol) and 5-chloro-1H-indole-2-carboxylic acid (0.84 mmol) were coupled according to Procedure A (0–25° C. reaction temperature). The crude product was triturated with dichloromethane and then with ether and dried. Yield 236 mg, 79%; HPLC (60/40) 4.63 minutes (97%); PBMS 356/358 (MH+, 100%);

Anal. Calcd for $C_{19}H_{18}ClN_3O_2+0.25\ H_2O$: C, 63.33; H, 5.18; N, 11.66.

Found: C, 63.37; H, 5.50; N, 12.06.

EXAMPLE 70a

(R)-2-Amino-N-methyl-3-phenyl-propionamide hydrochloride (R)-(1-Methylcarbamoyl-2-phenyl-ethyl)-carbamic acid tert-butyl ester (722 mg, 2.6 mmol) was dissolved in 4M HCl-dioxane (10 mL) at 0° C. The mixture was stirred for 1 hour at 25° C., concentrated and the residue triturated with ether. Yield, 517 mg, 93%.

EXAMPLE 70b

(R)-(1-Methylcarbamoyl-2-phenyl-ethyl)-carbamic acid tert-butyl ester

Methylamine hydrochloride (3.1 mmol) and Boc-D-phenyl-alanine (2.8 mmol) were coupled according to Procedure A (0–25° C. reaction temperature, 144 hour reaction time, washed with acid first, then base) giving the product which was used without further purification. Yield 760 mg, 96%.

EXAMPLE 71

5,6-Dichloro-1H-indole-2-carboxylic acid ((1S)-dimethylcarbamoyl-2-phenyl-ethyl)-amide (S)-2-Amino-N,N-dimethyl-3-phenyl-propionamide hydrochloride(0.06 mmol) and 5,6-dichloro-1H-indole-2-carboxylic acid (0.06 mmol) were coupled according to Procedure A (0–25° C. reaction temperature, 96 hour reaction time). The crude product was triturated with 1:1 ether-hexanes and dried. Yield 24 mg, 96%; HPLC (60/40) 8.05 minutes (97%); PBMS 405/407 (MH+, 100%);

Anal. Calcd for $C_{20}H_{19}Cl_2N_3O_2+0.25\ H_2O$: C, 58.76; H, 4.81; N, 10.28.

Found: C, 58.95; H, 4.89; N, 9.90.

EXAMPLE 71a

(S)-2-Amino-N,N-dimethyl-3-phenyl-propionamide hydrochloride (1-Dimethylcarbamoyl-2-phenyl-ethyl)-carbamic acid tert-butyl ester (8.6 g, 29 mmol) was dissolved in 4 M HCl-dioxane (110 ml) at 0° C. and the mixture stirred at 25° C. for 1 hour. The mixture was concentrated and the solids triturated with ether. Yield, 6.2 g, 92%; PBMS 193 (MH+, 100%).

EXAMPLE 71b

5,6-Dichloro-1H-indole-2-carboxylic acid

Zinc dust (3.52 g, 54 mmol) was added slowly to a warm solution of 3,4-dichloro-5-nitrophenylpyruvic acid (1.5 g, 5.4 mmol) in acetic acid (15 mL). After a few minutes, a vigorous reaction occurred (exothermic). The resulting solution was heated to 80° C. and the reaction appeared complete (TLC). The mixture was filtered, the filtered solids washed with acetic acid and the filtrate concentrated. The residue was dissolved in 2 N NaOH, the resulting solution washed with ether (3x), dichloromethane (2x) and acidified to pH 1 with 6N HCl and extracted with ethyl acetate. The extracts were dried and concentrated giving a light brown solid (458 mg, 34%): HPLC (60/40) 5.31 (93%).

EXAMPLE 71c

3,4-dichloro-5-nitrophenylpyruvic acid

Absolute ethanol (25 mL) was added at 3–15° C. to a stirred mixture of potassium metal (2.67 g, 68 mmol) in ether (100 mL). The resulting solution was treated at 3° C. with a solution of diethyl oxalate (10.0 g, 62 mmol) over 5–10 minutes, and the resulting solution stirred 30 minutes at 3° C. and 25° C. for 18 hours. The mixture was filtered and the resulting solid washed with ether and dried (13.7 g). This material (12.7 g) was dissolved in 400 mL hot water, the solution cooled and extracted with ether. The resulting aqueous layer was acidified to pH 2 with conc. HCl and the ether layer separated, dried and concentrated giving 7.5 g of a solid which was triturated with hexanes giving the title substance as a yellow solid (7.01 g 41%).

EXAMPLE 72

5-Bromo-1H-indole-2-carboxylic acid ((1S)-dimethylcarbamoyl-2-phenyl-ethyl)-amide (S)-2-Amino-N,N-dimethyl-3-phenyl-propionamide hydrochloride (1.0 mmol) and 5-bromo-1H-indole-2-carboxylic acid (1.0 mmol) were coupled according to Procedure A (0–25° C. reaction temperature) and the resulting foam triturated with 1:1 ether/hexanes and dried. Yield 374 mg, 90%; HPLC (60/40) 6.17 minutes (98%); mp 199–201° C.; PBMS 414/416 (MH+, 100%);

Anal. Calcd for $C_{20}H_{20}BrN_3O_2$: C, 57.98; H, 4.82; N, 10.14.

Found: C, 58.07; H, 5.12; N, 10.08.

EXAMPLE 73

5-Methyl-1H-indole-2-carboxylic acid ((1S)-dimethylcarbamoyl-2-phenyl-ethyl)-amide (S)-2-Amino-N,N-dimethyl-3-phenyl-propionamide hydrochloride (1.0 mmol) and 5-methyl-1H-indole-2-carboxylic acid (1.0 mmol) were coupled according to Procedure A (0–25° C. reaction temperature). The crude product was triturated with 1:1 ether-hexanes and dried. Yield 302 mg, 87%; HPLC (60/40) 5.46 minutes (99%); mp 198.5–200° C.; PBMS 350 (MH+, 100%);

Anal. Calcd for $C_{21}H_{23}N_3O_2$: C, 72.18; H, 6.63; N, 12.04.

Found: C, 72.14; H, 6.90; N, 12.11.

EXAMPLE 74

5-Methoxy-1H-indole-2-carboxylic acid ((1S)-dimethylcarbamoyl-2-phenyl-ethyl)-amide (S)-2-Amino-N,N-dimethyl-3-phenyl-propionamide hydrochloride (1.0 mmol) and 5-methoxy-1H-indole-2-carboxylic acid (1.0 mmol) were coupled according to Procedure A (0–25° C. reaction temperature, 60 hour reaction time) and the resulting foam triturated with ether. Yield 329 mg, 90%; HPLC (60/40) 4.27 minutes (99%); PBMS 366 (MH+, 100%);

Anal. Calcd for $C_{21}H_{23}N_3O_3+0.125\ H_2O$: C, 68.60; H, 6.37; N, 11.43.

Found: C, 68.50; H, 6.34; N, 11.45.

EXAMPLE 75

5-Fluoro-1H-indole-2-carboxylic acid ((1S)-dimethylcarbamoyl-2-phenyl-ethyl)-amide (S)-2-Amino-N,N-dimethyl-3-phenyl-propionamide hydrochloride (1.0 mmol) and 5-fluoro-1H-indole-2-carboxylic acid (1.0 mmol) were coupled according to Procedure A (0–25° C. reaction temperature, 60 hour reaction time) and the resulting solid triturated with ether. Yield 320 mg, 91%; HPLC (60/40) 4.74 minutes (100%); mp 229.5–232° C.; PBMS 354 (MH+, 100%);

Anal. Calcd for $C_{20}H_{20}FN_3O_2$: C, 67.97; H, 5.70; N, 11.89. Found: C, 67.88; H, 5.74; N, 11.71.

EXAMPLE 76

5-Cyano-1H-indole-2-carboxylic acid ((1S)-dimethylcarbamoyl-2-phenyl-ethyl)-amide (S)-2-Amino-N,N-dimethyl-3-phenyl-propionamide hydrochloride(0.16mmol)and 5-cyano-1H-indole-2-carboxylic acid (0.16 mmol) were coupled according to Procedure A (0–25° C. reaction temperature) and the product purified by chromatography on silica gel eluted with 1:1 ethyl acetate/hexanes. Yield 38 mg, 66%; HPLC (60/40) 4.08 minutes (97%); PBMS 361 (MH+, 100%);

$^1$H NMR (DMSO-d$_6$) δ12.1 (br, 1H), 9.04 (d, 1H, J=8.1 Hz), 8.27 (s, 1H), 7.52 (m, 2H), 7.43 (m, 1H), 7.33 (m, 2H), 7.25 (m, 2H), 7.18 (m, 1H), 5.10 (m, 1H), 3.03 (m, 2H), 3.00 (s, 3H), 2.83 (s, 3H).

Anal. Calcd for $C_{21}H_{20}N_4O_2+0.5\ H_2O$: C, 68.28; H, 5.73; N, 15.17.

Found: C, 68.51; H, 5.66; N, 14.85.

EXAMPLE 76a

5-Cyano-1H-indole-2-carboxylic acid

5-Cyano-1H-indole-2-carboxylic acid ethyl ester (1.71 g, 8.0 mmol) was added to a solution of ethanol (10 mL) and potassium hydroxide (2 g) and the resulting mixture heated at reflux for 1 hour. Water was added to dissolve the precipitate, and 6N HCl was added to bring the pH to 1. The mixture was cooled in an ice bath, filtered, and the resulting colorless solid washed with cold water and dried (1.51 g). A portion (1.4 g) was suspended in hot acetic acid (40 mL) and cooled giving a solid which was filtered, washed with cold ethyl acetate and dried: Yield 980 mg 70%; HPLC (60/40) 3.09 minutes (97%).

EXAMPLE 76b

5-Cyano-1H-indole-2-carboxylic acid ethyl ester

Zinc dust (57.8 g, 887 mmol) was added to a hot suspension of 3-cyano-5-nitrophenylpyruvic acid ethyl ester (23.2 g, 88 mmol) in acetic acid (225 mL) and water (225 mL, Caution!, vigorous initial exotherm) at a rate to maintain reflux, and the reaction was held at reflux for 0.5 hours. The mixture was filtered, the filtered salts washed with hot acetic acid (150 mL), and the filtrate chilled overnight giving crystals which were filtered, washed with cold 1:1 acetic acid-water, water, and dried (10.11 g, 53%). The filtrate was concentrated, the residue dissolved in ethyl acetate, and the resulting solution washed with sat. aqueous sodium bicarbonate, brine, dried and concentrated giving a second batch (5.05 g). The major lot was used in subsequent transformations.

EXAMPLE 76c

3-Cyano-5-nitrophenylpyruvic acid ethyl ester

A solution of sodium ethoxide in ethanol (from 2.2 g, 400 mmol sodium metal in 400 ml ethanol) was added at 0° C. to a mixture of distilled diethyl oxalate (120 g, 821 mmol) and 3-methyl-4-nitrobenzonitrile (32 g, 197 mmol). The resulting red solution was heated at 40° C. for 18 hours. The cooled mixture was diluted with water (600 mL) water and acidified with conc. HCl to pH 2.1. The precipitate that formed was collected by filtration of the 13° C. mixture, dried and purified by chromatography on silica eluted with 15, 30 and 50% acetone-hexanes giving an orange solid which was used without purification (23.6 g, 31%). A sample was recrystallized from ethyl acetate for characterization.

EXAMPLE 77

1H-indole-2-carboxylic acid ((1S)-dimethylcarbamoyl-2-phenyl-ethyl)-amide (S)-2-Amino-N,N-dimethyl-3-phenyl-propionamide hydrochloride (1.0 mmol) and 1H-indole-2-carboxylic acid (1.0 mmol) were coupled according to Procedure A (0–25° C. reaction temperature). The resulting solid was triturated with hexanes, then with ether. Yield 272 mg, 81%; HPLC (70/30) 3.49 minutes (99%); mp 199–200° C.;

PBMS 336 (MH+, 100%);

Anal. Calcd for $C_{20}H_{21}N_3O_2$: C, 71.62; H, 6.31; N, 12.53. Found: C, 71.45; H, 6.39; N, 12.50.

EXAMPLE 78

5-Chloro-1H-indole-2-carboxylic acid [(1S)-benzyl-2-((3S,4S)-dihydroxy-pyrrolidin-1-yl)-2-oxo-ethyl]-amide (3S,4S)-2-Amino-1-(3,4-dihydroxy-pyrrolidin-1-yl)-3-phenyl-propan-1-one hydrochloride (0.94 mmol) and 5-chloro-1H-indole-2-carboxylic acid (1.03 mmol) were coupled according to procedure A (170 hour reaction time) and the crude product purified by column chromatography on silica gel eluted with ethyl acetate. Yield 150 mg, 37%; HPLC (60/40) 3.08 minutes (96%);

$^1$H NMR (DMSO-d$_6$) δ11.73 (s, 1H), 8.90 (d, 1H, J=8.5 Hz), 7.72 (d, 1H, J=1.5 Hz), 7.39 (d, 1H, J=8.7 Hz), 7.30 (m, 2H), 7.30–7.1 (m, 5H), 5.22 (m, 1H), 5.13 (m, 1H), 4.91 (m, 1H), 3.97 (m, 1H), 3.91 (m, 1H), 3.60 (m, 2H), 3.5–3.2 (m, 2H) 3.00 (m, 2H).

Anal. Calcd for $C_{22}H_{22}ClN_3O_4$: C, 61.75; H, 5.18; N, 9.82.

Found: C, 61.65; H, 5.45; N, 9.17.

EXAMPLE 78a (3S,4S)-2-Amino-1-(3,4-dihydroxy-pyrrolidin-1-yl)-3-phenyl-propan-1-one hydrochloride (3S,4S)-[1-Benzyl-2-(3,4-dihydroxy-pyrrolidin-1-yl)-2-oxo-ethyl]-carbamic acid tert-butyl ester (360 mg, 1.00 mmol) was dissolved in 4 M HCl-dioxane (4 ml) at 25° C. for 3 hours. The mixture was concentrated and the resulting yellow solid triturated with ether and dried. Yield 304 mg, 103%.

EXAMPLE 78b

[1-Benzyl-2-(3,4-dihydroxy-pyrrolidin-1-yl)-2-oxo-ethyl]-carbamic acid tert-butyl ester Boc-L-Phenylalanine (2.2 mmol) and (3S,4S)-dihydroxy-pyrrolidine (U.S. Pat. No. 4,634,775, example 1C, 206 mg, 2.0 mmol) were coupled according to procedure A (0–25° C. reaction temperature) giving a colorless solid which was used without further purification. Yield 431 mg, 61%.

EXAMPLE 79

5-Chloro-1H-indole-2-carboxylic acid [(1S)-benzyl-2-((3RS)-hydroxy-piperidin-1-yl)-2-oxo-ethyl]-amide 2(S)-Amino-1-((3RS)-hydroxy-piperidin-1-yl)phenyl-propan-1-one hydrochloride (570 mg, 2.0 mmol) and 5-chloro-1H-indole-2-carboxylic acid (429 mg, 2.2 mmol) were coupled according to procedure A (5:2 dichloromethane-dimethylformamide solvent) and the crude product triturated with 1:1 ether-hexanes. The resulting solid was purified by column chromatography on silica gel eluted with 3:2, and 2:1 ethyl acetate/hexanes followed by trituration with 1:1 ether/hexanes. Yield 430 mg, 51%: HPLC (60/40) 3.45 minutes (95%);

Anal. Calcd for $C_{23}H_{24}ClN_3O_3 + 0.125\ C_6H_{14}$: C, 65.32; H, 5.94; N, 9.62.

Found: C, 65.01; H, 6.19; N, 9.22.

EXAMPLE 79a (2S)-Amino-1-(3-hydroxy-piperidin-1-yl)-3-phenyl-propan-1-one hydrochloride

[(1S)-Benzyl-2-((3RS)-hydroxy-piperidin-1-yl)-2-oxo-ethyl]-carbamic acid tert-butyl ester (7.13 g, 20 mmol) was dissolved in 4M HCl-dioxane (40 ml) at 25° C. for 3 hours. The mixture was concentrated and the resulting oil stirred under ether for 72 hours. The resulting suspension was filtered and the solid washed with ether and dried. Yield 5.64 g, 99%.

EXAMPLE 79b

[(1S)-Benzyl-2-((3RS)-hydroxy-piperidin-1-yl)-2-oxo-ethyl]-carbamic acid tert-butyl ester BOC-L-Phenylalanine (8.17 g, 30.8 mmol) and 3-hydroxypiperidine hydrochloride (4.24 g, 30.8 mmol) were coupled according to procedure A, giving the title compound as an oil which was used without further purification. Yield 7.79 g, 73%.

EXAMPLE 80

5-Chloro-1H-indole-2-carboxylic acid[(1S)-benzyl-2-oxo-2-(3-oxo-piperazin-1-yl)-ethyl]-amide 4-((2S)-Amino-3-phenyl-propionyl)-piperazin-2-one hydrochloride (140 mg, 0.5 mmol) and 5-chloro-1H-indole-2-carboxylic acid (98 mg, 0.5 mmol) were coupled according to procedure A and the crude product purified by column chromatography on silica gel eluted with ethyl acetate and 2% ethanol in ethyl acetate followed by trituration with ether. Yield 71 mg, 33%: HPLC (60/40) 3.53 minutes (100%); PBMS 425/427 (MH+, 100%);

$^1$H NMR (DMSO-$d_6$) δ11.78 (br, 0.5H), 11.76 (br, 0.5H), 9.03 (m, 0.5H), 9.02 (m, 0.5H), 8.06 (m, 0.5H), 8.04 (m, 0.5H), 7.73 (d, 1H, J=2 Hz), 7.38 (d, 1H, J=8.7 Hz), 7.32 (m, 2H), 7.20 (m, 2H), 7.2–7.1 (m, 2H), 5.15 (m, 0.5H), 5.05 (m, 0.5H), 4.20 (d, 0.5H, J=17 Hz), 4.08 (d, 0.5H, J=17 Hz), 3.85 (d, 0.5H, J=17 Hz), 3.9 (m, 0.5H), 3.6 (m, 2H), 3.2–2.9 (m, 4H).

EXAMPLE 80a 4-((2S)-Amino-3-phenyl-propionyl)-piperazin-2-one hydrochloride

[(1S)-Benzyl-2-oxo-2-(3-oxo-piperazin-1-yl)-ethyl]-carbamic acid tert-butyl ester (400 mg, 1.2 mmol) was dissolved in 4M HCl-dioxane (10 ml) at 25° C. for 0.5 hours. The mixture was concentrated and the residue co-evaporated with dichloromethane, triturated with ether, and dried. Yield 340 mg, 103%.

EXAMPLE 80b

[(1S)-Benzyl-2-oxo-2-(3-oxo-piperazin-1-yl)-ethyl]-carbamic acid tert-butyl ester BOC-L-Phenylalanine (530 mg, 2 mmol) and piperazin-2-one (J. Am. Chem. Soc. 62 1202 (1940), 200 mg, 2 mmol) were coupled according to procedure A (2:1 dichloromethane/dimethylformamide reaction solvent, washed with 1 N NaOH after acid washes) and the product used without further purification. Yield 404 mg, 58%.

EXAMPLE 81

5-Chloro-1H-indole-2-carboxylic acid ((1S)-methyl-2-morpholin-4-yl-2-oxo-ethyl)-amide (2S)-Amino-1-morpholin-4-yl-propan-1-one hydrochloride (195 mg, 1.0 mmol) and 5-chloro-1H-indole-2-carboxylic acid (195 mg, 1.0 mmol) were coupled according to procedure A (washed with 1 N NaOH after acid washes) giving crude product which was triturated with ether and dried. Yield 150 mg, 45%: HPLC (60/40) 3.61 minutes (100%); PBMS 336/338 (MH+, 100%);

Anal. Calcd for $C_{16}H_{18}ClN_3O_3$: C, 57.23; H, 5.40; N, 12.51.

Found: C, 57.01; H, 5.49; N, 12.24.

EXAMPLE 81a (2S)-Amino-1-morpholin-4-yl-propan-1-one hydrochloride ((1S)-Methyl-2-morpholin-4-yl-2-oxo-ethyl)-carbamic acid tert-butyl ester (3.88 g, 15 mmol) was dissolved in 4M HCl-dioxane (20 ml) at 25° C. for 1.25 hours. The mixture was concentrated and the residue triturated with ether and dried: Yield 2.51 g, 86%.

EXAMPLE 81b ((1S)-Methyl-2-morpholin-4-yl-2-oxo-ethyl)-carbamic acid tert-butyl ester BOC-L-Alanine (3.50 mg, 20 mmol) and morpholine (1.74 g, 20 mmol) were coupled according to procedure A (washed with 1 N NaOH after acid washes) giving a colorless oil which was used without further purification. Yield 3.94 g, 76%.

EXAMPLE 82

5-Chloro-1H-indole-2-carboxylic acid ((1S)-methylcarbamoyl-2-phenyl-ethyl)-amide (2S)-Amino-N-methyl-3-phenyl-propionamide hydrochloride (214 mg, 1.0 mmol) and 5-chloro-1H-Indole-2-carboxylic acid (195 mg, 1.0 mmol) were coupled according to procedure A and the crude product triturated with ether and dried. Yield 160 mg, 45%: HPLC (60/40) 4.60 minutes (100%);

$^1$H NMR (DMSO-$d_6$) δ11.70 (br, 1H), 8.73 (d, 1H, J=8.5 Hz), 8.08 (q, 1H, J=4.6 Hz), 7.72 (d, 1H, J=1.9 Hz), 7.39 (d, 1H, J=8.8 Hz), 7.32 (m, 2H), 7.25–7.10 (m, 5H), 4.68 (m, 1H), 3.10 (dd, A of AB, 1H, J=4.2, 13 Hz), 2.96 (dd, 1H, J=10.7, 13 Hz), 2.62 (d, 3H, J=4.6 Hz).

EXAMPLE 82a

(2S)-Amino-N-methyl-3-phenyl-propionamide hydrochloride

[((1S)-1-Methylcarbamoyl-2-phenyl-ethyl)-carbamic acid tert-butyl ester (2.35 g, 8.45 mmol) was dissolved in 4 M HCl-dioxane (20 ml) at 25° C. for 2 hours. The mixture was concentrated and the residue triturated with ether, and dried. Yield 1.70 g, 94%.

EXAMPLE 82b

((1S)-1-Methylcarbamoyl-2-phenyl-ethyl)-carbamic acid tert-butyl ester

BOC-L-phenylalanine (2.65 g, 10 mmol) and methylamlne hydrochloride (675 mg, 10 mmol) were coupled according to procedure A (washed with 1N NaOH after acid washes) yielding the title compound as a colorless solid which was used without further purification. Yield 2.41 g, 87%; HPLC (60/40) 3.83 minutes (100%).

EXAMPLE 83

5-Chloro-1H-indole-2-carboxylic acid [(1S)-(methoxy-methyl-carbamoyl)-ethyl]-amide (2S)-Amino-N-methoxy-N-methyl-propionamide hydrochloride (169 mg, 1.0 mmol) and 5-chloro-1H-indole-2-carboxylic acid (195 mg, 1.0 mmol) were coupled according to procedure A (washed with 1 N NaOH after acid washes) giving the product (290 mg, 94%): HPLC (60/40) 4.03 minutes (94%); PBMS 310/312 (MH+, 100%);

Anal. Calcd for $C_{14}H_{16}ClN_3O_3$: C, 54.29; H, 5.21; N, 13.57.

Found: C, 54.17; H, 5.26; N, 13.31.

EXAMPLE 83a

(2S)-Amino-N-methoxy-N-methyl-propionamide hydrochloride

[(1S)-(Methoxy-methyl-carbamoyl)-ethyl]-carbamic acid tert-butyl ester (3.55 g, 15.3 mmol) was dissolved in 4 M HCl-dioxane (20 ml) at 25° C. for 0.75 hours. The mixture was concentrated and the residue co-evaporated with ether and dichloromethane and dried. Yield 2.2 9 (86%).

EXAMPLE 83b

[1-(Methoxy-methyl-carbamoyl)-ethyl]-carbamic acid tert-butyl ester

L-BOC-Alanine (3.50 g, 20 mmol) and O,N-dimethylhydroxyamine hydrochloride (1.94 g, 20 mmol) were coupled according to procedure A (washed with 1N NaOH after acid washes) and the resulting colorless solid was used without further purification. Yield 3.71 9 (80%).

EXAMPLE 84

5-Bromo-1H-indole-2-carboxylic acid ((1S)-carbamoyl-2-phenyl-ethyl)-amide

L-Phenylalaninamide hydrochloride (835 mg, 4.17 mmol) and 5-bromo-1H-indole-2-carboxylic acid (1.0 g, 4.17 mmol) were coupled according to procedure A substituting the following workup: the reaction mixture was diluted with ethyl acetate and 2N NaOH. The resulting suspension was filtered and the collected solid washed with ethyl acetate, 2N NaOH, 2 N HCl, ether, and dried. Yield 890 mg; PBMS 386/388 (MH+, 100%);

Anal. Calcd for $C_{18}H_{16}BrN_3O_2$: C, 55.97; H, 4.18; N, 10.88.

Found: C, 55.69; H, 4.48; N, 10.48.

EXAMPLE 85

5-Chloro-1H-indole-2-carboxylic acid ((1S)-(methoxy-methyl-carbamoyl)-2-phenyl-ethyl)-amide (2S)-Amino-N-methoxy-N-methyl-3-phenyl-propionamidehydrochloride(317 mg, 1.3 mmol) and 5-chloro-1H-indole-2-carboxylic acid (253 mg, 1.3 mmol) were coupled according to procedure A (0–25° C., washed first with acid, then base). The crude product was purified by column chromatography on silica gel eluted with 30% and 40% ethyl acetate in hexanes. The foam obtained was triturated with isopropyl ether yielding an off white solid (356 mg, 71%): HPLC (60/40) 8.28 minutes (98%);

Anal. Calcd for $C_{20}H_{20}ClN_3O_3$: C, 62.26; H, 5.22; N, 10.89.

Found: C, 62.22; H, 5.60; N, 10.73.

EXAMPLE 85a

(2S)-Amino-N-methoxy-N-methyl-3-phenyl-propionamide hydrochloride

[(1S)-(Methoxy-methyl-carbamoyl)-2-phenyl-ethyl]-carbamic acid tert-butyl ester (2.97 g, 9.6 mmol) was dissolved in 4M HCl-dioxane (36 ml) at 0° C. The resulting mixture was stirred at 25° C. for 1 hour, concentrated and the residue triturated with ether and dried. Yield 2.27 g, 96%.

EXAMPLE 85b

[(1S)-(Methoxy-methyl-carbamoyl)-2-phenylethyl]-carbamic acid tert-butyl ester BOC-L-phenylalanine (4.0 g, 15.1 mmol) and N,O-dimethylhydroxylamine hydrochloride (3.82 g, 15.1 mmol) were coupled according to Procedure A (0–25° C., washed first with acid, then base). The resulting colorless oil was used without purification (3.22 g, 69%).

EXAMPLE 86

(2RS)-[(5-Chloro-1H-indole-2-carbonyl)-amino]-2-methyl-3-phenyl-propionic acid methyl ester Racemic 2-amino-2-methyl-3-phenyl-propionic acid methyl ester (200 mg, 0.87 mmol) and 5-chloro-1H-indole-2-carboxylic acid (170 mg, 0.87 mmol) were coupled according to Procedure A (2:1 dichloromethane/ dimethylformamide solvent) and the product purified by chromatography on silica gel eluted with 10% ethyl acetate in hexanes. Yield 286 mg, 89%; HPLC (60/40) 9.63 minutes (85%); TSPMS 371/373 (MH+, 100%);

$^1$H NMR (CDCl$_3$) δ9.31 (s, 1H), 7.57 (d, 1H, J=<1 Hz), 7.37 (d, 1H, J=8.8 Hz), 7.20 (m, 4H), 7.04 (m, 2H), 6.84 (s, 1H), 6.66 (s, 1H), 3.81 (s, 3H), 3.67 (A of AB, 1H, J=13.5 Hz), 3.28 (B of AB, 1H, J=13.5 Hz), 1.80 (s, 3H).

EXAMPLE 87

(2RS)-[(5-Chloro-1H-indole-2-carbonyl)-amino]-2-methyl-3-phenyl-proprionic acid

Aqueous 2N LiOH (0.10 ml, 0.50 mmol) was added to a solution of (2RS)-[(5-chloro-1H-indole-2-carbonyl)-amino]-2-methyl-3-phenyl-proplonic acid methyl ester (132 mg, 0.36 mmol) in tetrahydrofuran (8 ml) at 25° C. The resulting solution was stirred for 1 hour, concentrated and the residue dissolved in ethyl acetate and water (15 ml). The pH was adjusted to 1 with 2 N HCl at 0° C. The organic layer was separated, washed with water, brine and dried giving a foam which was used without further purification (129 mg, 102%): HPLC (60/40) 4.42 minutes (99%); TSPMS 357/359 (MH+, 100%);

$^1$H NMR (CDCl$_3$) δ9.88 (s, 1H), 7.57 (s, 1H), 7.35 (d, 1H, J=8.8 Hz), 7.3–7.2 (m, 5H), 7.16 (m, 2H), 6.75 (m, 1H), 6.67 (m, 1H), 3.57 (A of AB, 1H, J=13.7 Hz), 3.42 (B of AB, 1H, J=13.7 Hz), 1.80 (s, 3H).

Anal. Calcd for $C_{19}H_{17}ClN_2O_3$+0.3 $H_2O$: C, 63.00; H, 4.90; N, 7.73.

Found: C, 63.38; H, 5.31; N, 7.42.

EXAMPLE 88

5-Chloro-1H-indole-2-carboxylic acid [(1S)-benzyl-2-oxo-2-(1-oxo-1-thiomorpholin-4-yl)-ethyl]-amide m-Chloroperoxybenzoic acid (80 mg of 50%, 0.23 mmol) was added at 25° C. to a solution of 5chloro-1H-indole-2-carboxylic acid ((1S)-benzyl-2-oxo-2-thiomorpholin-4-yl-ethyl)-amide (100 mg, 0.23 mmol) in dichloromethane (2 mL). After 1 hour, the mixture diluted with ethyl acetate and washed three times with a 50/50 mixture of saturated aqueous sodium bicarbonate and 10% aqueous sodium thiosulfate, once with saturated aqueous sodium bicarbonate, brine, and dried. The crude product was purified by column chromatography on silica gel eluted with 0.5–8% ethanol in dichloromethane to give the title compound. Yield 76%; HPLC (60/40) 3.97 minutes (97%); mp 230–234° C.; TSPMS 444/446 (MH+, 100%);

Anal. Calcd for $C_{22}H_{22}ClN_3O_3S$+0.5 $H_2O$: C, 58.34; H, 5.12; N, 9.28.

Found: C, 58.41; H, 5.37; N, 8.90.

EXAMPLE 69

5-Chloro-1H-indole-2-carboxylic acid [1(1S)-benzyl-2-(1,1-dioxo-1-thiomorpholin-4-yl)-2-oxo-ethyl]-amide m-Chloroperoxybenzoic acid (202 mg of 50%, 0.58 mmol) was added at 25° C. to a solution of 5-chloro-1H-indole-2-carboxylic acid ((1S)-benzyl-2-oxo-2-thiomorpholin-4-yl-ethyl)-amide (100 mg, 0.23 mmol) in dichloromethane (2 mL). After 1 hour, the mixture was diluted with ethyl acetate and the resulting solution washed three times with a 50/50 mixture of saturated aqueous sodium bicarbonate and 10% aqueous sodium thiosulfate, once with saturated aqueous sodium bicarbonate, brine, and dried. The crude product was purified by column chromatography on silica gel eluted with 30%, 40% and 50% ethyl acetate in hexanes to give the title compound. Yield 60%; HPLC (60/40) 5.69 minutes (98%); PBMS 460/462 (MH+, 100%);

Anal. Calcd for $C_{22}H_{22}ClN_3O_4S$+0.4 $H_2O$: C, 56.56; H, 4.92; N, 8.99.

Found: C, 66.77; H, 5.15; N, 8.60.

EXAMPLE 90

5-Chloro-1H-indole-2-carboxylic acid [(1S)-benzyl-2-oxo-2-(1-oxo-1-thiazolidin-3-yl)-ethyl]-amide m-Chloroperoxybenzoic acid (167 mg of 50%, 0.48 mmol) was added at 25° C. to a solution of 5-chloro-1H-indole-2-carboxylic acid ((1S)-benzyl-2-oxo-2-thiazolidin-3-yl-ethyl)-amide (200 mg, 0.48 mmol) in dichloromethane (4 mL). After 0.5 hours, the mixture was diluted with ethyl acetate and washed three times with a 50/50 mixture of saturated aqueous sodium bicarbonate and 10% aqueous sodium thiosulfate, once with saturated aqueous sodium bicarbonate, brine, and dried. The crude product was concentrated to a yellow solid and then purified by column chromatography on silica gel eluted with 1–8% ethanol in dichloromethane and then triturated with ether giving the title compound. Yield 151 mg (73%); HPLC (60/40) 3.64 minutes (98%); PBMS 430/432 (MH+, 100%);

Anal. Calcd for $C_{21}H_{20}ClN_3O_3S$+0.6 $H_2O$: C, 57.23; H, 4.85; N, 9.53.

Found: C, 57.00; H, 4.85; N, 9.25.

EXAMPLE 91

5-Chloro-1H-indole-2-carboxylic acid [(1S)-benzyl-2-(3hydroxylmino-pyrrolidin-1-yl)-2-oxo-ethy]-amide Hydroxylamine hydrochloride (68 mg, 0.82 mmol) and potassium carbonate (136 mg, 0.98 mmol) were added to a solution of 5chloro-1H-indole-2-carboxylic acid [(1S)-benzyl-2-oxo-2-(3-oxo-pyrrolidin-1-yl)-ethyl]-amide in ethanol (5 ml) and water (1 ml) at 25° C. After 48 hours, the reaction mixture was concentrated and the residue dissolved in ethyl acetate. The resulting solution was washed two times with water and once with brine, dried over $Na_2SO_4$, and concentrated. Two substances appearing to be syn/anti oxime isomers separated by chromatography on silica eluted with 2.5%, 5%, and 10% ethanol in dichloromethane.

EXAMPLE 91(i)

For the less polar Isomer:

Yield 48 mg (14%); HPLC (60/40) 4.69 minutes (97%); mp 216–220° C. (darkened at 210° C.); PBMS 425/427 (MH+, 100%).

$^1$H NMR (DMSO-d$_6$) δ11.75 (br, 1H), 10.87 (s, 0.5H), 10.86 (s, 0.5H), 9.02 (m, 1H), 7.72 (d, 1H, J=2.0 Hz), 7.4–7.1 (m, 8H), 4.95 (m, 0.5H), 4.85 (m, 0.5H), 4.40 (d,0.5H, J=15 Hz), 4.0 (m, 1.5H), 3.9 (m, 0.5H), 3.61 (m, 1H), 3.5 (m, 0.5H), 3.10 (m, 2H), 2.8–2.5 (m, 2H);

Anal. Calcd for $C_{22}H_{21}ClN_4O_3$: C, 62.19; H, 4.98; N, 13.19.

Found: C, 61.82; H, 5.07; N, 12.95.

EXAMPLE 91(ii)

For the more polar isomer:

Yield 69 mg (20%); HPLC (60/40) 6.78 minutes (>99%); mp 223–224° C. (dec, tar); PBMS 425/427 (MH+, 100%); $^1$H NMR (DMSO-d$_6$) δ11.74 (br, 1H), 10.87 (s, 1H), 10.84 (s, 1H), 9.05 (d, 0.5H, J=8.1 Hz), 8.99 (d, 1H, J=8.0 Hz), 7.73 (d, 1H, J=2 Hz), 7.4–7.1 (m, 8H), 4.97 (m, 1H), 4.85 (m, 1H), 4.47 (d, 0.5H, J=17 Hz), 3.95 (m, 1.5H), 3.87 (m, 0.5H), 3.65—3.4 (m, 1.5H), 3.10 (m, 2H), 2.7–2.5 (m, 2H).

Anal. Calcd for C$_{22}$ H$_{21}$ClN$_4$O$_3$: C, 62.19; H, 4.98; N, 13.19.

Found: C, 61.85; H, 5.17; N, 13.16.

EXAMPLE 92

5-Chloro-1H-indole-2-carboxylic acid (1-benzyl-2-oxo-2-piperidin-1-yl-ethyl-amide Piperidine hydrochloride (0.34 mmol) and 2-[(5-chloro-1H-indole-2-carbonyl)-amino]-3-phenyl-propionic acid (0.30 mmol) were coupled according to procedure A (0–25° C. reaction temperature). The crude product was chromatographed on silica gel eluted with 20%, 30%, 40%, 50%, 75% and 100% ethyl acetate in hexane giving partial separation. The pure fractions were pooled giving 31 mg (25%) of the title substance: HPLC (60/40) 9.38 minutes (94%); PBMS 410/412 (MH+, 100%);

Anal. Calcd for C$_{23}$ H$_{24}$N$_3$O$_2$Cl+0.5 H$_2$O: C, 65.94; H, 6.02; N, 10.03.

Found: C, 65.70; H, 6.19; N, 9.66.

EXAMPLE 93

5-Chloro-1H-indole-2-carboxylic acid carbamoylmethyl-amide

[(5-Chloro-1H-indole-2-carbonyl)-amino]-acetic acid methyl ester (100 mg, 0.40 mmol) was added to a saturated solution of ammonia in methanol (ca. 3 mL) at 25° C. The suspension was sonicated for 1 hour and the resulting solution concentrated. The residue was triturated with ether/hexanes and dried. Yield 77 mg, 77%; HPLC (60/40) 2.78 minutes (98%); PBMS 252/254 (MH+, 100%);

$^1$H NMR (DMSO-d$_6$) δ11.82 (br, 1H), 8.80 (t, 1H), 7.71 (d, 1H, J=ca. 1 Hz), 7.43 (d, 1H, J=7–8 Hz), 7.42 (br, 1H), 7.18 (dd, 1H, J=7–8, ca. 2 Hz), 7.14 (s, 1H), 7.08 (br, 1H), 3.82 (m, 2H).

Anal. Calcd for C$_{11}$H$_{10}$ClN$_3$O$_2$+0.125 H$_2$O: C, 52.03; H, 4.07; N, 16.55.

Found: C, 52.05; H, 4.08; N, 1 6.63.

EXAMPLE 94

1-{(2S)-[(6-Bromo-1H-indole-2-carbonyl)-amino]-3-phenyl-propionyl}-pyrrolidine-(2S)-carboxylic acid Trifluoroacetic acid was added to a solution of 1-{(2S)-[(5-bromo-1H-indole-2-carbonyl)-amino]-3-phenyl-propionyl}-pyrrolidine-(2S)-carboxylic acid tert-butyl ester (345 mg, 0.64 mmol) in dichloromethane (2 ml) at 0° C. After 1 hour at 25° C., the reaction mixture was concentrated, triturated with ether and dried giving a yellow solid. Yield 273 mg, 88%; HPLC (70/30) 4.75 minutes (98%); TSPMS 484/486 (MH+, 100%);

Anal. Calcd for C$_{23}$ H$_{22}$BrN$_3$O$_4$+0.25 H$_2$O: C, 56.51; H, 4.64; N, 8.60.

Found: C, 56.28; H, 4.78; N, 8.26.

EXAMPLE 94a

1{(2S)-[(Bromo-1H-indole-2-carbonyl)-amino]-3-phenyl-propionyl}-pyrrolidine-(2S)-carboxylic acid tert-butyl ester L-phenylalanine-L-proline tert-butyl ester (333 mg, 1.0 mmol) and 5-bromo-1H-indole-2-carboxylic acid were coupled according to procedure A (72 hour reaction time). The product was purified by column chromatography on silica gel eluted with 15%, 20% and 30% ethyl acetate giving a pale yellow foam. Yield 428 mg (79%); HPLC (70/30) 5.84 minutes (81%).

EXAMPLE 95

5-Chloro-1H-indole-2-carboxylic acid [2-oxo-2-(1RS)-oxo-1-thiazolidin-3-yl)-ethyl]-amide m-Chloroperoxybenzoic acid (426 mg of 50%, 1.2 mmol) was added at 25° C. to a solution of 5-chloro-1H-indole-2-carboxylic acid (2-oxo-2-thiazolidin-3-yl-ethyl)-amide (400 mg, 1.2 mmol) in dichloromethane (8 mL) at 25° C. After 1 hour, the mixture was diluted with ethyl acetate (ca 80 mL) and the resulting solution washed three times with a 1:1 mixture of saturated aqueous NaHCO$_3$/10% aqueous Na$_2$S$_2$O$_3$, saturated aqueous NaHCO$_3$, and brine. The resulting suspension was filtered and the filtered solid washed with water and dried giving a crystalline solid. HPLC (60/40) 2.52 minutes (98.5%); TSPMS 340/342 (MH+, 70%), 357 (100%); $^1$H NMR (DMSO-d$_6$) δ11.82 (br, 1H), 8.84 (m, 1H), 7.73 (d, 1H, J=2.0 Hz), 7.43 (d, 1H, J=8.7 Hz), 7.19 (dd, 1H, J=2.0, 8.7 Hz), 7.18 (s, 1H), 4.92 (dd, 0.5H, J=12.1 Hz), 4.71 (dd, 0.5H, J=2.2, 13 Hz), 4.47 (d, 1H, J=12.1 Hz), 4.4–3.9 (m, 4.5H), 3.3 (m, 0.5H), 3.13 (m, 1H), 3.0 (m, 0.5H).

Anal. Calcd for C$_{14}$H$_{14}$ClN$_3$O$_3$S+0.8 H$_2$O: C, 47.47; H, 4.44; N, 11.86.

Found: C, 47.46; H, 4.07; N, 11.83.

EXAMPLE 96

1-{(2S)-[(5-Chloro-1H-indole-2-carbonyl)-amino]-3-phenyl-propionyl}-(4R)-hydroxy-pyrrolidine-(2S)-carboxylic acid Excess aqueous 2 M LiOH was added to a solution of 1-{(2S)-[(5-chloro-1H-indole-2-carbonyl)-amino]-3-phenyl-propionyl}-(4R)-hydroxy-pyriolidine(2S)-carboxylic acid benzyl ester (215 mg, 0.40 mmol) in tetrahydrofuran at 25° C. After 2 hours, the mixture was diluted with ethyl acetate and ice and the mixture acidified to pH 1–2 with 6 N HCl. The acidic layer was extracted three times with ethyl acetate, and the organic layers combined and dried. The residue was triturated with ether and dried giving a colorless solid (190 mg, 106%): HPLC (60/40) 3.43 minutes (94%); TSPMS 456/458 (MH+, 100%);

Anal. Calcd for C$_{23}$H$_{22}$ClN$_3$O$_5$+0.5 C$_4$H$_8$O$_2$: C, 60.06; H, 5.24; N, 8.40.

Found: C, 60.27; H, 5.33; N, 8.13.

EXAMPLE 97

(S)-2-[(5-Chloro-1H-indole-2-carbonyl)-amino]-3-(1H-indol-3-yl)-propionic acid methyl ester L-Tryptophan methyl ester hydrochloride (1.05 mmol) and 5-chloro-1H-indole-2-carboxylic acid (1.0 mmol) were coupled according to Procedure A (0–25° C., dimethylformamide reaction solvent) and the product purified by chromatography on silica gel eluted with 10%, 20%, 30%, 40%, 50% and 60% ethyl acetate-hexanes giving a yellow foam. Yield, 79%; HPLC (60/40) 7.43 minutes (96%);

$^1$H NMR (CDCl$_3$) δ11.78 (br, 1H), 10.85 (br, 1H), 8.93 (d, 1H, J=7.7 Hz), 7.73 (d, 1H, J=1.9 Hz), 7.57 (d, 1H, J=7.7 Hz), 7.41 (d, 1H, J=8.7 Hz), 7.32 (d, 1H, J=8.0 Hz), 7.22 (m, 2H), 7.18 (dd, 1H, J=2.1, 8.8 Hz), 7.06 (m, 1H), 6.99 (m, 1H), 4.74 (m, 1H), 3.65 (s, 3H), 3.35–3.2 (m, 2H).

EXAMPLE 98

(±)-3-{[Chloro-1H-indole-2-carbonyl)-amino]-acetyl}-thiazolidine-2-carboxylic acid Methyl Ester (±)-Thiazolidine-2-carboxylic acid methyl ester hydrochloride (1.02 mmol) and [(5-chloro-1H-indole-2-carbonyl)-amino]-acetic acid (1.02 mmol) were coupled according to Procedure A (1:1 dichloromethane-dimethylformamide solvent) and the crude product triturated with 1:1 ether-hexanes giving a light yellow solid. Yield 79%; HPLC (60/40) 4.47 minutes (95%); TSPMS 382/384 (MH+, 100%).

$^1$H NMR (DMSO-d$_6$) δ11.82 (s, 1H), 8.85 (t, 1H, J=7 Hz), 7.73 (d, 1H, J=2 Hz), 7.43 (d, 1H, J=8.8 Hz), 7.18 (dd, 1H, J=8.8, 2 Hz), 7.17 (s, 1H), 5.44 (s, 1H), 4.25 (m, 1H), 4.1 (m, 1H), 3.95 (m, 1H), 3.34 (s, 3H), 3.3 (m, 2H).

Anal. Calcd for C$_{16}$H$_{16}$CL N$_3$O$_4$S: C, 50.33; H 4.22; N, 11.00.

Found: C, 50.56; H, 4.46; N, 10.89.

EXAMPLE 99

(±)-3-{[(5-Chloro-1H-indole-2-carbonyl)-amino]-acetyl}-thiazolidine-2-carboxylic acid A solution of 3-{[(5-chloro-1H-indole-2-carbonyl)-amino]-acetyl}-thiazolidine2-carboxylic acid methyl ester (196 mg, 0.5 mmol) in methanol (10 mL) was treated with aqueous 1 N NaOH (0.5 mL) at 25° C. After 3 hours, more 1 N NaOH (0.25 mL) was added. The mixture was stirred at 25° C. overnight, concentrated, the residue stirred with ethyl acetate (30 mL) and 1 N NaOH (5 mL), and the resulting mixture acidified to pH 1.8 with aqueous 6 N HCl. The aqueous layer was separated and extracted with ethyl acetate. The organic layers were combined, dried, and concentrated giving a solid which was triturated with 1:1 ether-hexane and dried. Yield 186 mg, 99%; HPLC (60/40) 3.13 minutes (98%); TSPMS 368/370 (MH+, 70%), 339 (100%).

$^1$H NMR (DMSO-d$_6$) δ11.80 (s, 1H), 8.84 (br, 1H), 7.23 (s, 1H), 7.44 (d, 1H, J=8.8 Hz), 7.18 (dd, 1H), 7.17 (s, 1H), 4.32 (s, 1H), 4.25 (m, 2H), 4.0 (m, 2H), 3.3 (m, 2H).

EXAMPLE 99a (+)-Thiazolidine-2-carboxylic Acid Methyl Ester

A mixture of (±)-thiazolidine-2-carboxylic acid (1.58 g, 11.9 mmol) and chlorotrimethylsilane (5.1 g, 47 mmol) in methanol (22 mL) was heated at reflux for 5 hours, cooled, and concentrated giving a solid (2.19 g, 100%).

EXAMPLE 100

S-tert-Butyl 2-[(5-chloro-1H-indole-2-carbonyl)-amino]-3-phenyl-propionate

Procedure B

To a solution of 5-chloro-1H-indole-2-carboxylc acid (0.50 g, 2.6 mmol), L-phenylalanine tert-butyl ester hydrochloride (0.66 g, 2.6 mmol), triethylamine (0.36 mL, 2.6 mmol) and 4-dimethylaminopyridine (0.16 g, 1.3 mmol) in dichloromethane (20 mL) was added 1-(3-dimethylaminopropyl)3-ethylcarbodiimide (0.73 g, 3.8 mmol). The mixture was stirred at room temperature overnight, diluted with chloroform, washed with 2N HCl, water and brine, dried over magnesium sulfate and concentrated. The product was purified by flash-chromatography (30% acetone in hexanes) and obtained as a pale yellow foam (0.86 g, 85%).

Anal. calc.: C, 66.25; H 5.81; N, 7.03;

Found: C, 66.57; H, 6.11,N, 6.86.

The following examples (101 to 122) were prepared by methods analogous to Procedure B.

EXAMPLE 101

R-Methyl-2-[(5-fluoro-1H-indole-2-carbonyl)-amino]-3-phenyl-propionate

From 5-fluoro-1H-indole-2-carboxylic acid and D-phenyl-alanine methyl ester.

$^1$H NMR (300 MHz, CDCl$_3$) δ3.22 (m, 2H), 3.80 (s, 3H), 5.10 (m, 1H), 6.62 (d, 6 Hz, 1H), 6.75 (d, 2 Hz,1H), 7.05 (dt, 2 Hz, 8 Hz, 1H), 7.10–7.15 (m, 2H), 7.25–7.40 (m, 4H), 7.73 (d, 2.1 Hz, 1H), 9.50 (br, 1H).

EXAMPLE 102

R-Methyl 2-[(5-7-dichloro-1H-indole-2-carbonyl)-amino]-3-phenyl-propionate

From 5,7-dichloro-1H-indole-2-carboxylic acid and D-phenylalanine methyl ester.

$^1$H NMR (300 MHz, CDCl$_3$) δ3.25 (m, 2H), 3.80/3.95 (s, 3H), 5.10 (m, 1H), 6.62 (d, 6 Hz, 1H), 6.69 (d, 2 Hz, 1H), 7.10–7.15 (m, 2H), 7.25–7.35 (m, 3H), 7.50–7.56 (s, 1H), 9.35 (br, 1H).

EXAMPLE 102a 5,7-Dichloro-1H-indole-2-carboxylic acid

A. Ethyl 2-oxopropionate 2,4-dichlorophenylhydrazone

A mixture of 2,4-dichlorophenylhydrazine (1.0 g, 4.7 mmol), ethyl pyruvate (0.53 mL, 4.7 mmol), triethylamine (0.65 mL, 4.7 mmol) and ethanol (5 mL) was heated at reflux overnight. The solvent was evaporated and the residue taken up in chloroform. The solution was washed with water and brine and dried over magnesium sulfate and concentrated, leaving an oil (1.1 g, 98%).

B. Ethyl 5,7-dichloro-1H-indole-2-carboxylate

A solution of ethyl 2-oxopropionate 2,4-dichlorophenylhydrazone (1.1 g, 4.6 mmol) and anhydrous zinc chloride (10 g, 74 mmol) in glacial acetic acid (12 mL) was heated at reflux for ½ hours. The reaction mixture was poured into water and extracted with ether twice. The combined organic layers were washed with water and brine, dried over magnesium sulfate and concentrated. The product was purified by flash-chromatography (30% ethyl acetate in hexanes) and obtained as an oil (0.80 g, 67%).

C. 5.7-Dichloro-1H-indole-2-carboxylic acid

A solution of ethyl 5,7-dichloro-1H-indole-2-carboxylate (0.80 g, 3.1 mmol) in 1 N NaOH (40 mL) and methanol (50 mL) was heated to reflux for 3 hours. The methanol was removed in vacuo and the aqueous residue was acidified with 1N HCl and extracted with chloroform twice. The combined extracts were washed with water and brine, dried over magnesium sulfate and concentrated to a solid (0.58 g, 76%).

The following indole carboxylic acids were prepared by the same sequence: 4-Chloro-5-fluoro-1H-indole-2-carboxylic acid and 6-chloro-5-fluoro-1H indole-2-carboxylic acid (as a mixture) from 3-chloro-4-fluorophenylhydrazine. 5,7-Difluoro-1H-indole-2-carboxylic acid from 2,4-difluorophenylhydrazine

EXAMPLE 103

(±)-Ethyl-2-[(5-chloro-1H-indole-2-carbonyl)-amino]-3-phenyl-propionate

From 5-chloro-1H-indole-2-carboxylic acid and DLphenyl-alanine ethyl ester.

mp 146–147° C.

Anal. Calc.: C, 64.61; H, 5.42; N, 7.54;

Found: C, 64.73; H, 5.26; N, 7.57.

EXAMPLE 104

S-3-Bromo-5-chloro-1H-indole-2-carboxylic acid 1-dimethyl-carbamoyl-2-phenyl-ethyl)-amide From 3-bromo-5-chloro-1H-indole-2-carboxylic acid and S-2-amino-N,N-dimethyl-3-phenyl-propionamide.

Anal. Calc.: C, 53.53; H, 4.27; N, 9.36;

Found: C, 53.51; H, 4.46; N, 9.38.

EXAMPLE 104a

3-Bromo-5-chloro-1H-indole-2-carboxylic acid

To a solution of 5-chloro-1H-indole-2-carboxylic acid (2.0 g, 10.2 mmol) in acetic acid (24 mL) was added a solution of bromine (0.53 mL, 10.2 mmol) in acetic acid (16 mL). After 20 minutes, the mixture was poured into water and extracted with chloroform twice. The combined extracts were washed with water twice and brine, dried over magnesium sulfate and concentrated. The product was obtained as a solid (2.5 g, 89%).

EXAMPLE 104b (S)-2-Amino-N,N-dimethyl-3-phenyl-propionamide hydrochloride

A. (S)-(1-Dimethylcarbamoyl-2-phenyl-ethyl)-carbamic acid tert-butyl ester

To a solution of tert-Boc-phenylalanine (10 g, 38 mmol), dimethylamine hydrochloride (3.4 g, 41 mmol), triethylamine (5.8 mL, 42 mmol) and hydroxybenzo-triazole (6.6 g, 49 mmol) in dichloromethane (300 mL) was added 1-(3-dimethylaminopropyl)-3-ethylcarbodiimide (9.4 g, 49 mmol). The mixture was stirred overnight, then quenched with 2 N HCl and concentrated. The residue was taken up in ethyl acetate and this solution was washed with water and brine, dried over magnesium sulfate and concentrated. The residue was triturated in chloroform, the solid was filtered and the filtrate was concentrated to an oil (11 g, 100%).

B. (S)-2-Amino-N,N-dimethyl-3-phenyl-propionamide hydrochloride (S)-(1-Dimethylcarbamoyl-2-phenyl-ethyl)-carbamic acid tert-butyl ester (11.0 g, 38 mmol) was dissolved in ethyl acetate (125 mL) and HCl was bubbled into the solution for 10 min. The solution was stirred for 1 hour at room temperature, then concentrated. The residue was triturated in ether, the solid was filtered and dried on high vacuum (8.6 g, 100%).

EXAMPLE 105

S-5-Chloro-4-nitro-1H-indole-2-carboxylic acid (1-dimethylcarbamoyl-2-phenyl-ethyl)-amide From 4-nitro-5-chloro-1H-indole-2-carboxylic acid and S-2-amino-N,N-dimethyl-3-phenyl-propionamide.

$^1$H NMR (300 MHz, CDCl$_3$) δ2.75 (s, 3H), 2.97 (s, 3H), 3.20 (m, 2H), 5.30 (m, 1H), 7.07 (d, 2 Hz, 1H), 7.24–7.32 (m, 5H), 7.40 (d, 7 Hz, 1H), 8.12 (br d, 7 Hz, 1H) 1H).

EXAMPLE 105a

4-Nitro-5-chloro-1H-indole-2-carboxylic acid

A. 2-[(4-Chloro-3-nitro-phenyl)-hydrazono]-propionic acid ethyl ester

To a solution of sodium nitrite (2.17 g, 31 mmol) in water (60 mL) and conc. HCl (12 mL) at 0° C. was added 4-chloro-3-nitroaniline (5.0 g, 29 mmol). After 5 minutes, a solution of ethyl methylacetoacetate (4,5 mL, 29 mmol) in water (60 mL), ethanol (30 mL) and 50% potassium hydroxide (10 mL) was added and the reaction mixture was stirred overnight. The precipitate was collected (7.0 g, 91%).

B. Ethyl 6chloro-4-nitro-1H-indole-2-carboxylate

A mixture of 2-[(4-chloro-3-nitro-phenyl)-hydrazono]-propionic acid ethyl ester (2.0 g, 6.7 mmol) and polyphosphoric acid (7 g) was heated to 90–110° C. for 2 hours. The mixture was cooled, poured onto an ice/water mixture and the solid was collected. Flash-chromatography (1% methanol in chloroform) provided the title compound (0.58 g, 32%) and 5-chloro-6-nitro-1H-indole-2-carboxylate (0.31 g, 17%).

C. 4-Nitro-5-chloro-1H-indole-2-carboxylic acid

The title compound was prepared by hydrolysis of ethyl 5-chloro4-nitro-1H-indole-2-carboxylate as described for the preparation of 5,7-dichloro-1H-indole-2-carboxylic acid.

EXAMPLE 106

S-7-Nitro-1H-indole-2-carboxylic acid (1-dimethylcarbamoyl-2-phenyl-ethyl)-amide From 7-nitro-1H-indole-2-carboxylic acid and S-2-amino-N,N-dimethyl-3phenyl-propionamide.

$^1$H NMR δ2.8 (s, 3H), 3.0 (s, 3H), 3.1–3.3 (m, 2H), 5.35 (q, 7 Hz, 1H), 6.95 (s, 1H), 7.15–7.3 (m, 6H), 7.9 (d, 8 Hz, 1H), 8.2 (d, 8 Hz, 1H), 10.3 (br, 1H).

EXAMPLE 107

(±)-Methyl 2-[(5-chloro-1H-indole-2-carbonyl)-amino]-3-phenyl-butyrate

From 5-chloro-1H-indole-2-carboxylic acid and DL-β-methylphenylalanine methyl ester.

mp 135–136° C.

Anal. Calc.: C, 64.78; H, 5.17; N, 7.56;

Found: C, 64.76; H, 5.26; N, 7.64.

EXAMPLE 108

(±)-5-Chloro-1H-indole-2-carboxylic acid [1-(2-fluoro-benzyl)-2-oxo-2-thiazolidin-3-yl-ethyl]-amide From 5-chloro-1H-indole-2-carboxylic acid and (±)-2-amino-3-(2-fluoro-phenyl)-1-thiazolidin-3-yl-propan-1-one.
mp 216–217° C.
Anal. Calc.: C, 58.40; H, 4.43; N, 9.73;
Found: C, 58.45; H, 4.53; N, 9.71.

EXAMPLE 108a (±)-2-Amino-3-(2-fluorophenyl)-1-thiazolidin-3-yl-propan-1-one hydrochloride

A. (±)-2-tert-Butoxycarbonylamino-3-[(2-fluoro-phenyl)-propionic acid

To a mixture of DL-3-fluoro-phenylalanine (1.0 g, 5.5 mmol) and triethylamine (1.14 mL, 8.2 mmol) in dichloromethane (20 mL) was added di-tert-butyl dicarbonate (1.4 g, 6.55 mmol). The mixture was stirred at room temperature overnight, then poured into water, acidified with 1 N HCl and extracted with chloroform. The combined extracts were washed with water and brine, dried over magnesium sulfate and concentrated. The product was purified by flash-chromatography (chloroform/methanol/acetic acid, 89:10:1) and obtained as a solid (1.28 g, 83%, mp 118–119° C.).

B. (±)-[1-(2-Fluorobenzyl)-2-oxo-2-thiazoildin-3-yl-ethyl]-carbamic acid tert-butyl ester To a mixture of 2-tert-butoxycarbonylamino-3-(2-fluoro-phenyl)-propionic acid (0.50 g, 1.77 mmol), thiazolidine (0.15 mL, 1.94 mmol) and 4-dimethylamino-pyridine (0.21 g, 1.77 mmol) in dichloromethane (15 mL) was added EDC (0.44 g, 2.31 mmol). The reaction mixture was stirred at room temperature overnight, diluted with chloroform, washed with 2 N HCl, water and brine, dried over magnesium sulfate and concentrated. The product was purified by flash-chromatography (30% acetone in hexanes) and obtained as a colorless solid (0.39 g, 62%, mp 133–134° C.).

C. (±)-2-Amino-3-(2-fluorophenyl)-1-thiazolidin-3-yl-propan-1-one hydrochloride HCl was bubbled into a solution of [1-(2-fluoro-benzyl)-2-oxo-2-thiazolidine-3-yl-ethyl]-carbamic acid tert-butyl ester (0.39 g, 1.1 mmol) in ethyl acetate (15 mL). The solution was concentrated, the residue was triturated in ether, the solid was filtered and dried (0.27 g, 84%, mp 217–218° C.).

The following amines were prepared by analogous methods in the same sequence:

(±)-2-Amino-3-(2-chloro-phenyl)-1-thiazolidin-3-yl-propan-1-one from DL-2-chloro-phenylalanine
(±)-2-Amino-3-(3-cyano-phenyl)-1-thiazolidin-3-yl-propan-1-one from DL-3cyano-phenylalanine
(±)-2-Amino-3-(3-chloro-phenyl)-1-thiazolidin-3-yl-propan-1-one from DL-3-chloro-phenylalanine
(±)-2-Amino-3-(3-trifluoromethyl-phenyl)-1-thiazolidin-3-yl-propan-1-one from DL-3-trifluoromethyl-phenylalanine
(S)-2-Amino-1-(4-hydroxy-piperidin-1-yl)-3-(4-methoxy-phenyl)-propan-1-one from L-4-methoxy-phenylalanine

EXAMPLE 109

(±)-5-Chloro-1H-indole-2-carboxylic acid [1-(2-chloro-benzyl)-2-oxo-2-thiazolidin-3-yl-ethyl]-amide From 5-chloro-1H-indole-2-carboxylic acid and (±)-2-amino-3-(2-chloro-phenyl)-1-thiazolidin[]yl-propan-1-one.
mp 214–216° C.
Anal. Calc.: C, 56.26; H, 4.58; N, 9.37;
Found: C, 56.27; H, 4.54; N, 9.36.

EXAMPLE 110

(±)-5-Chloro-1H-indole-2-carboxylic acid [2-(3-cyano-phenyl)-1-(thiazolidine-3-carbonyl)-ethyl]-amide From 5-chloro-1H-indole-2-carboxylic acid and (±)-2-amino-3-(3cyano-phenyl)-1-thiazolidin-3-yl-propan-1-one.
mp 183–184° C.
Anal. Calc.: C, 60.20; H, 4.36; N, 12.77;
Found: C, 60.11; H, 4.84; N, 12.43.

EXAMPLE 111

(±)-5-Chloro-1H-indole-2-carboxylic acid [1-(3chloro-benzyl)-2-oxo-2-thiazolidin-3-yl-ethyl]-amide From 5-chloro-1H-indole-2-carboxylic acid and (±)-2-amino-3-(3-chloro-phenyl)-1-thiazolidin-3-yl-propan-1-one.
mp 188–190° C.
Anal. Calc.: C, 56.26; H, 4.27; N, 9.37;
Found: C, 56.38; H, 5.04; N, 9.04.

EXAMPLE 112

(±)-5-Chloro-1H-indole-2-carboxylic acid [2-oxo-2-thiazolidin-3-yl-1-(3-trifluoromethyl-benzyl)-ethyl]-amide From 5-chloro-1H-indole-2-carboxylic acid and (±)-2-amino-3(3-trifluoromethyl-phenyl)-1-thiazolidin3yl-propan-1-one.
mp 205–207° C.
Anal. Calc.: C, 54.83; H, 3.97; N, 8.72;
Found: C, 64.44; H, 4.14; N, 8.88.

EXAMPLE 113

S-5-Chloro-1H-indole-2-carboxylic acid [1-(4-methoxy-benzyl)-2-oxo-2-thiazolidin-3-yl-ethyl]-amide From 5-chloro-1H-indole-2-carboxylic acid and S-2-amino-3-(4-methoxy-phenyl)-1-thiazolidin-3-yl-propan-1-one.
Anal. Calc.: C, 59.52; H, 5.00; N, 9.47;
Found: C, 60.00; H, 5.55; N, 8.90.
Mass Spec. m/e 444 (M$^+$ 1).

EXAMPLE 114

(±)-Chloro-1H-indole-2-carboxylic acid [1-(3-chloro-benzyl)-2-(4-hydroxy-piperidin-1-yl]-2-oxo-ethyl]-amide From 5-chloro-1H-indole-2-carboxylic acid and (±)-2-amino-1-(4hydroxy-piperidin-1-yl)-3-(3-chloro-phenyl)-propan-1-one.
mp 98° C. dec.

EXAMPLE 115

S-5-Chloro-4-fluoro-1H-indole-2-carboxylic acid (1-benzyl-2-oxo-2-thiazolidin-3yl-ethyl)-amide and S-6-chloro-4-fluoro-1H-indole-2-carboxylic acid (1-benzyl-2-oxo-2-thiazolidin-3-yl-ethyl)-amide From a mixture of 5-chloro-4-fluoro-1H-indole-2-carboxylic acid and 6-chloro-4-fluoro-1H-indole-2-carboxylic acid, and S-2-amino-3-phenyl-1-thiazolidin-3-yl-propan-1-one.

mp 105–125° C. dec.
Anal. Calcd.: C, 58.40; H, 4.43; N, 9.73;
Found: C, 58.54; H, 4.59; N, 9.58.

EXAMPLE 116

(+)-2-[(5-Chloro-1H-indole-2-carbonyl)-amino]-proprionic acid methyl ester

From 5chloro-1H-indole-2-carboxylic acid and DL-alanine methyl ester hydrochloride.

mp 199–201° C.
Anal. Calc.: C, 55.63; H, 4.67; N, 9.98;
Found: C, 55.70; H, 4.75; N, 10.06.

EXAMPLE117

(±)-2-[(5-Chloro-1H-indole-2-carbonyl)-amino]-3-[4-(4,5-dihydro-1H-imidazol-2-yl)-phenyl]-propionic acid methyl ester From 5-chloro-1H-indole-2-carboxylic acid and (±)-2-amino-3-[4-(4,5-dihydro-1H-imidazol-2-yl)-phenyl]-propionic acid methyl ester.

$^1$H NMR (300 MHz, CDCl$_3$) δ3.1–3.3 (m, 2H), 3.70 (s, 3H), 3.95 (s, 4H), 4.8 (m, 1H), 7.15 (s, 1H), 7.17 (d, 8 Hz, 1H), 7.40 (d, 8 Hz, 1H), 7.65 (d, 7 Hz, 1H), 7.75 (s, 1H), 7.88 (d, 8 Hz, 1H), 9.10 (br d, 9 Hz, 1H), 10.5 (s, 1H), 11.8 (br s, 1H).

EXAMPLE 117a (±)-2-Amino-2-[4-(4,5-dihydro-1H-imidazol-2-yl)-phenyl]-propionic acid methyl ester

A. 2-Acetylamino-2-[4-(4,5-dihydro-1H-imidazol-2-yl)-benzyl]-malonic acid diethyl ester A solution of 2-acetylamino-2-[(4-methoxycarbonimidoyl)-benzyl]-malonic acid, diethyl ester (G. Wagner et al. *Pharmazie* 1974, 29, 12) (5.3 9, 13 mmol) and ethylenediamine (4.8 g, 80 mmol) in ethanol (100 mL) was stirred at 60° C. for 5 hours. After cooling, the solvent was evaporated, water was added to the residue and the solid was filtered and dissolved in hot 1 N HCl. After cooling, the precipitate was filtered and dried (3.1 g).

B. (±)-2-Amino-3-[4-(4,5-dihydro-1H-imidazol-2-yl)-phenyl]-propionic acid dihydrochloride To 2-acetylamino-2-[4-(4,5-dihydro-1H-imidazol-2-yl)-benzyl]-malonic acid, diethyl ester (3.0 g, 7.3 mmol) was added glacial acetic acid (50 mL) and 3N HCl (100 mL). The solution was heated to reflux for 3 hours, cooled and concentrated to a white solid which was recrystallized from methanol/ether (2.0 g, mp 270–272° C. dec.).

C. (±)-2-Amino-3-[4-(4,5-dihydro-1H-imidazol-2-yl)-phenyl]-propionic acid methyl ester (±)-2-Amino-3-[4-(4,5-dihydro-1H-imidazol-2-yl)-phenyl]-propionic acid dihydrochloride (0.50 g, 1.6 mmol) was placed in thionyl chloride (1 mL) and methanol (25 mL). The mixture was heated to reflux for 30 minutes, at which time more thionyl chloride (3 mL) and methanol (75 mL) were added. After another 3 hours at reflux, the solution was concentrated, the residue was dissolved in a small amount of methanol and ethyl acetate was added to induce precipitation. The solid was collected and dried (0.40 g, mp 230° C. dec.).

EXAMPLE 118

(S)-5,7-Difluoro-1H-indole-2-carboxylic acid [1-benzyl-2-(4-hydroxy-piperidin-1-yl)-2-oxo-ethyl]-amide From 5,7-difluoro-1H-indole-2-carboxylic acid and (S)-2-amino-1-(4-hydroxy-piperidin-1-yl)-3-phenyl-propan-1-one.

mp 95–110° C.

EXAMPLE 119

S4-chloro-5-fluoro-1H-indole-2-carboxylic acid (1-dimethylcarbamoyl-2-phenyl-ethyl)-amide and S-6-chloro-5-fluoro-1H-indole-2-carboxylic acid (1-dimethylcarbamoyl-2-phenyl-ethyl)-amide From a mixture of 5chloro-4-fluoro-1H-indole-2-carboxylic acid and 6-chloro-4-fluoro-1H-indole-2-carboxylic acid, and (S)-2-amino-N,N-dimethyl-3-phenyl-propionamide.

mp 200–210° C.
Anal. Calc.: C, 61.94; H, 4.94; N, 10.83;
Found: C, 62.21; H, 4.99; N, 10.84.

EXAMPLE 120

(S)-5,7-Difluoro-1H-indole-2-carboxylic acid (1-benzyl-2-oxo-2-thiazolidin-3-yl-ethyl)-amide From 5,7-difluoro-1H-indole-2-carboxylic acid and (S)-2-amino-3-phenyl-1-thiazolidin-3-yl-propan-1-one.

mp 175–185° C.
Anal. Calc.: C, 60.71; H, 4.61; N, 10.11;
Found: C, 60.79; H, 4.66; N, 9.93.

EXAMPLE 121

(S)-5,7-Difluoro-1H-indole-2-carboxylic acid [1-benzyl-2-(1,1-dioxo-1-thiazolidin-3-yl)-2-oxo-ethyl]-amide From 5,7-difluoro-1H-indole-2-carboxylic acid and (S)-2-amino-1-(1,1-dioxo-1-thiazolidin-3-yl)-3-phenyl-propan-1-one hydrochloride.

mp 95–110° C.
MS 448 (MH$^+$).

EXAMPLE 122

S-5-Chloro-1H-indole-2-carboxylic acid [1-(2-fluoro-benzyl)-2-(4-hydroxy-piperidin-1-yl)-2-oxo-ethyl]-amide Procedure C To a solution of 5-chloro-1H-indole-2-carboxylic acid (0.49 g, 2.5 mmol), S-2-amino-3-(2-fluoro-phenyl)-1-

(4hydroxy-piperidin-1-yl)-propan-1-one (0.76 g, 2.6 mmol), triethylamine (0.35 mL, 2.5 mmol) and hydroxybenzotriazole (0.34 g, 2.5 mmol) in dichloromethane (6 mL) was added 1-(3-dimethylaminopropyl)-3-ethylcarbodiimide (0.53 g, 2.8 mmol). The mixture was stirred at room temperature overnight, diluted with dichloromethane, washed with water, 1 N HCl and saturated sodium bicarbonate, dried over magnesium sulfate and concentrated. The product was purified by flash-chromatography (chloroform/methanol, 8:1) and obtained as an off-white solid (0.82 g, 73%).

mp 120–122° C.

EXAMPLE 122a (S)-2-Amino-3-(2-fluoro-phenyl)-1-(4-hydroxy-piperidin-1-yl)-propan-1-one hydrochloride A. (S)-2-tert-Butoxycarbonylamino-3-(2-fluorophenyl)-1-thiazolidin-3-yl-propan-1-one From L-Boc-2-fluorophenylalanine and 4-hydroxypiperidine by a method analogous to Procedure C.

B. (S)-2-Amino-3-(2-fluoro-phenyl)-1-(4-hydroxy-piperidin-1-yl)-propan-1-one hydrochloride The title compound was prepared by reaction of L-2-tert-butoxycarbonylamino-3-(2-fluorophenyl)-1-thiazolidin-3-yl-propan-1-one with HCl according to the analogous method described in Example 108a, step C.

The following amines were prepared by analogous methods in the same sequence:

S-2-Amino-3-(4-methoxy-phenyl)-1-thiazolidin-3-yl-propan-1-one
S-2-Amino-3-(2-fluoro-phenyl)-1-(4-hydroxy-piperidin-1-yl)-propan-1-one
S-2-Amino-1-(4hydroxy-piperidin-1-yl)-3-(4-methoxy-phenyl)-propan-1-one
S-2-Amino-3-(2-chloro-phenyl)-1-(4hydroxy-piperidin-1-yl)-propan-1-one
S-2-Amino-3-(4-methoxy-phenyl)-1-morpholine-4-propan-1-one
S-2-amino-3-(4-methoxy-phenyl)-1-(4-acetyl-piperazinyl)-propan-1-one By an analogous process to that of (Procedure C) were prepared the following examples (122–138).

EXAMPLE 123

(2SR), (3RS)-2-[(5-Chloro-1H-indole-2-carbonyl)-amino]-3-hydroxy-3-phenyl-propionic acid methyl ester From 5chloro-1H-indole-2-carboxylic acid and (+)-threo b-phenylserine methyl ester.

mp 196–197° C.

EXAMPLE 124

S-5-Fluoro-1H-indole-2-carboxylic acid [1-(4-methoxy-benzyl)-2-oxo-2-thiazolidin-3-yl-ethyl]-amide From 6fluoro-1H-indole-2-carboxylicacidandS-2-amino-3(4-methoxy-phenyl)-1-thiazolidin-3-yl-propan-1-one.

mp 90–115° C.

Anal. calc.: C, 61.81; H, 5.19; N, 9.83;
Found: C, 60.94; H, 5.33; N, 10.01.

EXAMPLE 125

S-5-Chloro-1H-indole-2-carboxylic acid [1-(2chloro-benzyl)-2-(4-hydroxy-piperidin-1-yl)-2-oxo-ethyl]-amide From 5-chloro-1H-indole-2-carboxylic acid and S-2-amino-3-(2chloro-phenyl)-1-(4-hydroxy-piperidin-1-yl)-propan-1-one.

mp 127–129° C.

EXAMPLE 126

S-5-Chloro-1H-indole-2-carboxylic acid [1-(4-methoxy-benzyl)-2-morpholin-4-yl-2-oxo-ethyl]-amide From S-chloro-1H-indole-2-carboxylic acid S-2-amino-3-(4-methoxy-phenyl)-1-morpholin-4-yl-propan-1-one.

mp 95–105° C.

Anal. calc.: C, 62.51; H, 6.47; N, 9.51;
Found: C, 61.82; H, 6.05; N, 6.97.

EXAMPLE 127

S-5-Chloro-1H-indole-2-carboxylic acid [2-(4-acetyl-piperazin-1-yl)-1-(4-methoxy-benzyl)-2-oxo-ethyl]-amide From 5-chloro-1H-indole-2-carboxylic acid and S-2-amino-3-(4-methoxy-phenyl)-1-(4-acetyl-piperazinyl)-propan-1-one.

mp 120–135° C.

Anal. calc.: C, 62.17; H, 5.64; N, 11.60;
Found: C, 62.76; H, 6.20; N, 10.44.

EXAMPLE 128

S-5-Fluoro-1H-indole-2-carboxylic acid [1-(benzothiazole-2-ylcarbanoyl)-2-phenyl-ethyl]-amide From S-2-[(5-fluoro-1H-indole-2-carbonyl)-amino]-3-phenyl-propionic acid and 2-amino-1,3-benzothiazole.

mp 139–141° C.

EXAMPLE 129

S-5-Fluoro-1H-indole-2-carboxylic acid (1-benzyl-2-morpholin-4-yl-2-oxo-ethyl)-amide From S-2-[(5-fluoro-1H-indole-2-carbonyl)-amino]-3-phenyl-propionic acid and morpholine.

mp 234–236° C.

EXAMPLE 130

5-Fluoro-1H-indole-2-carboxylic acid [1S-benzyl-2-oxo-2-(3,3,5RS-trimethyl-azepan-1-yl)-ethyl]-amide From 2-[(5-fluoro-1H-indole-2-carbonyl)-amino]-3-phenyl-propionic acid and (±)-3,3,5-trimethylazepane.

mp 125–127° C.

Anal. calc.: C 72.14, H 7.18, N 9.35;
Found: C 72.00, H 7.58, N 9.10.

EXAMPLE 131

5-Fluoro-1H-indole-2-carboxylic acid [1S-benzyl-2-(3RS-carbamoyl-piperidin-1-yl)-2-oxo-ethyl]-amide From S-2-[(5-fluoro-1H-indole-2-carbonyl)-amino]-3-phenyl-propionic acid and 3-carbamoyl-piperidine.

mp 234–236° C.

EXAMPLE 132

5-Fluoro-1H-indole-2-carboxylic acid [2-phenyl-1S-(thiochroman-4RS-ylcarbamoyl)-ethyl]-amide From S-2-[(5-fluoro-1H-indole-2-carbonyl)-amino]-3-phenyl-propionic acid and (+)thiochroman-4-ylamine.
mp 225–226° C.
Anal. calc.: C 68.48, H 5.11, N 8.88;
Found: C 68.40, H 5.64, N 8.61.

EXAMPLE 133

S-5-Fluoro-1H-indole-2-carboxylic acid [1-(5-methyl-isoxazol-3-ylcarbamoyl)-2-phenyl-ethyl]-amide From S-2-[(5-fluoro-1H-indole-2-carbonyl)-amino]-3-phenyl-propionic acid and 5-methyl-isoxazol-3-ylamine.
mp 219–221° C.

EXAMPLE 134

S-5-Fluoro-1H-indole-2-carboxylic acid [2-phenyl-1-(4,5,6,7-tetrahydro-benzothiazol-2-ylcarbamoyl)-ethyl]-amide From S-2-[(5-fluoro-1H-indole-2-carbonyl)-amino]-3-phenyl-propionic acid and 4,5,6,7-tetrahydro-benzothiazol-2-yl-amine.
mp 162–165° C.

EXAMPLE 135

S-5-Fluoro-1H-indole-2-carboxylic acid [1-(5-methyl-thiazol-2-ylcarbamoyl)-2-phenyl-ethyl]-amide From S-2-[(5-fluoro-1H-indole-2-carbonyl)-amino]-3-phenyl-propionic acid and 4-methyl-thiazol-2-ylamine.
mp 211–213° C.

EXAMPLE 136

S-5-Methyl-1H-indole-2-carboxylic acid [1-(5-methyl-isoxazol-3-ylcarbamoyl)-2-phenyl-ethyl]-amide From S-2-[(5-methyl-1H-indole-2-carbonyl)-amino]-3-phenyl-propionic acid and 5-methyl-isoxazol-3-ylamine.
mp 243–245° C.
Anal. calc.: C 68.64, H 5.51, N 13.93;
Found: C 68.29, H 5.81, N 14.05.

EXAMPLE 137

S-5-Methyl-1H-indole-2-carboxylic acid [2-(4-acetyl-piperazin-1-yl)-1-benzyl-2-oxo-ethyl]-amide From S-2-[(5-methyl-1H-indole-2-carbonyl)-amino]-3-phenyl-propionic acid and 1-piperazin-1-yl-ethanone.
mp 221–223° C.

EXAMPLE 138

S-5-Chloro-1H-indole-2-carboxylic acid (1-carbamoyl-2-phenyl-ethyl)-amide

From 5-chloro-1H-indolecarboxylic acid and S-2-amino-3-phenyl-propionamide.
mp 257–258° C.

EXAMPLES 139 AND 140

(2RS)-2,3-Dihydro-1H-indole-2-carboxylic acid (R-1-dimethylcarbamoyl-2-phenyl-ethyl)-amide To a mixture of DL-indoline-2-carboxylic acid (0.38 g, 2:3 mmol), (R)-2-amino-N,N-dimethyl-3-phenyl-propionamide hydrochloride (0.53 g, 2.3 mmol), hydroxy-benzotriazole (0.66 g, 4.2 mmol) and triethylamine (0.32 mL, 2.3 mmol) in dichloromethane (5 mL) was added EDC (0.64 g, 2.7 mmol). The solution was stirred overnight, diluted with dichloro-methane, washed with water and brine, dried over magnesium sulfate and concentrated. The two isomeric products were separated by flash-chromatography (EtOAc, then EtOAc/MeOH, 20:1).

EXAMPLE 139

Less polar isomer (oil, 0.23 g, 30%):
$^1$H NMR (300 MHz, CDCl$_3$) δ2.68 (s, 3H), 2.87 (s, 3H), 3.02–3.09 (m, 3H), 3.55 (dd, J=10 Hz, 6 Hz, 1H), 4.61 (m, 1H), 5.10 (q, J=8 Hz, 1H), 6.95 (d, J=8 Hz, 1H), 7.11–7.30 (m, 8H), 8.12 (br, 1H).
MS (Cl, NH$_3$) 394 (M$^+$+17).

EXAMPLE 140

More polar isomer (0.11 g, 14%): mp 136–140° C.

EXAMPLES 141 AND 142

(2RS)-5-Chloro-2,3-dihydro-1H-indole-2-carboxylic acid (1-S-dimethylcarbamoyl-2-phenyl-ethyl)-amide To a solution of S-5-chloro-1H-indole-2-carboxylic acid (1-dimethylcarbamoyl-2-phenyl-ethyl)-amide (2.60 g, 7.0 mmol) in THF (20 mL) and methanol (20 mL) was added magnesium (1.75 g, 73 mmol) by portions, at such a rate as to maintain the reaction going without excess heat. After the reaction had ceased, the reaction was concentrated to a low volume, the residue was partitioned between 1 N HCl and ethyl acetate, the combined ethyl acetate layers were washed with water and brine, dried over magnesium sulfate and concentrated. The products were separated by flash-chromatography (1% methanol in chloroform).

EXAMPLE 141

Less polar isomer:
$^1$H NMR (300 MHz, CDCl$_3$) δ2.61 (s, 3H), 2.83 (s, 3H), 3.00–3.02 (m, 3H), 3.47 (dd, J=9.9 Hz, 6.4 Hz, 1H), 4.43 (m, 1H), 5.10 (q, J=7.5 Hz, 1H), 6.64 (d, J=8.8 Hz, 1H), 7.00 (s, 1H) 7.16–7.29 (m, 7H), 7.70 (br, 1H).
MS (Cl, NH$_3$) 372 (M$^+$+1).

EXAMPLE 142

More polar isomer: mp 125° C. dec.

EXAMPLES 143 AND 144

2RS 5-chloro-2,3-dihydro-1H-indole-2-carboxylic acid (1R-dimethylcarbamoyl-2-phenyl-ethyl)-amide By an analogous method to that of Example 141 and 142, using R-5-chloro-1H-indole-2-carboxylic acid (1-dimethylcarbamoyl-2-phenyl-ethyl)-amide, the two diastereomers were prepared.

EXAMPLE 143

Less polar isomer: mp 122–124 ° C. dec.

EXAMPLE 144

More polar isomer:
$^1$H NMR (300 MHz, CDCl$_3$) δ2.70 (s, 3H), 2.83 (s, 3H), 2.77–2.97 (m, 3H), 3.40 (dd, J=16.6 Hz, 10.8 Hz, 1H), 4.28 (m, 1H), 4.40 (d, J=5.2 Hz, 1H), 5.12 (q, J=7.8 Hz, 1H), 6.56 (d, J=9.0 Hz, 1H), 6.96 (d, J=7.8 Hz, 1H), 6.99 (s, 1H) 7.03–7.07 (m, 2H), 7.11–7.18 (m, 3H), 7.74 (d, J=8.8 Hz, 1H).

EXAMPLE 145

3-Chloro-1H-indole-2-carboxylic acid (1R-dimethylcarbamoyl-2-phenyl-ethyl)-amide To a solution of 2,3-dihydro-1H-indole-2-carboxylic acid (1R-dimethylcarbamoyl-2-phenyl-ethyl)-amide (less polar isomer, 0.50 g, 1.42 mmol) in DMF (7.5 mL) was added N-chlorosuccinimide (0.55 g, 1.42 mmol). After overnight stirring, the solvent was evaporated and the product purified by flash-chromatography (hexanes/ethyl acetate, 1:1).

$^1$H NMR (300 MHz, CDCl$_3$) δ2.55 (s, 3H), 2.80 (s, 3H), 3.05–3.20 (m, 2H), 5.32 (m, 1H), 7.10–7.25 (m, 6H), 7.30 (d, 7 Hz, 1H), 7.58 (d, 7 Hz, 1H), 8.11 (br d, 7 Hz, 1H), 10.20 (br, 1H). MS m/e 370 (M$^+$+1).

EXAMPLE 146

3-Chloro-1H-indole-2-carboxylic acid (1S-dimethylcarbamoyl-2-phenyl-ethyl)-amide The title compound was prepared by an analogous method th that of Example 145 from the more polar isomer of 2,3-Dihydro-1H-indole-2-carboxylic acid (1R-dimethylcarbamoyl-2-phenyl-ethyl)-amide.

$^1$H NMR (300 MHz, CDCl$_3$) δ2.55 (s, 3H), 2.85 (s, 3H), 3.05–3.20 (m, 2H), 5.32 (m, 1H), 7.10–7.25 (m, 6H), 7.35 (d, 7 Hz, 1H), 7.58 (d, 7 Hz, 1H), 8.11 (br d, 7 Hz, 1H), 10.30 (br, 1H). MS m/e 370 (M$^+$+1).

HPLC conditions for Examples 147–165: Detector wavelength 215 nm. HPLC retention time (in minutes) from a Waters Novapac C18 3.9×150 mm column. Eluent A=50 mM KH$_2$PO$_3$, pH 3; Eluent B=Acetonitrile; Flow rate 1.5 mL/minute; Gradient 90% A/10% B (5 minutes) to 40% A/60% B (5 minutes hold). HPLC retention times (RT) are in minutes. The percent value given is the percent of total integration due to the specified peak. By HPLC, the starting acid was present in an amount less than 5% of the total integration, unless specified otherwise.

EXAMPLE 147

(S)2-[(5-Fluoro-1H-indole-2-carbonyl)-amino]-3-phenyl-propionic acid

To a solution of 5-fluoroindole-2-carboxylic acid (5.0 g,28 mmol) and methylene chloride (250 mL) was added 1-(3-dimethylaminopropyl)-3-ethylcarbodiimide hydrochloride (5.53 g, 27.9 mmol), L-phenylalanine t-butyl ester hydrochloride (6.54 g, 27.9 mmol) and triethyl amine (7.1 mL, 5.13 g, 51 mmol). After stirring for 40 hours at room temperature, the reaction mixture was washed with an equal volume of water and then an equal volume of 1 N HCl. The aqueous acid was extracted with methylene chloride and the combined organic layers were sequentially washed with equal volumes of water (twice) and brine. The organic solution was dried (MgSO$_4$), filtered and concentrated to give S-t-butyl 2-[(5fluoro-1H-indole-2-carbonyl)-amino]-3-phenyl-propionate (2.97 g, 31%). This was then diluted with methylene chloride (75 mL) and cooled to 0° C. Trifluoroacetic acid (8 mL) was added and the reaction was then stirred at room temperature for 2 days and then heated to reflux for 6.5 hours. After allowing to come to room temperature over night, the solution was concentrated to dryness to yield a brown solid. This was then dissolved in a small amount of ether and pentanes, filtered to remove particulates and concentrated to give the title compound as a brown foam (2.65 g, quantitative yield): mp 125–127° C.; HPLC RT 5.72; TSPMS ion (expected) 327(326);

$^1$H NMR (CDCl$_3$) δ9.0 (br s, 2H), 7.4–7.2 (m, 6H), 7.02 (dt, J=2.4, 9.1 Hz, 1H), 6.80 (d, J=7.7 Hz, 1H), 6.75 (d, J=1.6 Hz, 1H), 5.09 (q, J=7.6 Hz, 1H), 3.35 (dd, J=5.8, 7.6 Hz, 1H), 3.26 (dd, J=5.8, 7.6 Hz, 1H).

EXAMPLE 148

(S)-2-[(5-Methyl-1H-indole-2-carbonyl)-amino]-3-phenyl-propionic acid

A repeat of the above proceedure with 5-methylindole-2-carboxylic acid (3.0 g, 17 mmol), methylene chloride (185 mL), 1-(3-dimethylaminopropyl)-3-ethylcarbodiimide hydrochloride (3.28 g, 17.1 mmol), L-phenylalanine t-butyl ester hydrochloride (4.01 g, 15.6 mmol) and triethyl amine (4.5 mL, 3.31 g, 32.7 mmol) afforded the analogous t-butyl ester (2.42, 41%). After dilution with methylene chloride (60 mL) and trifluoroacetic acid (6.6 mL), the reaction was heated to reflux for 3 hours, allowed to come to room temperature over night and concentrated. The crude product was slurried in ethyl acetate, filtered to remove insoluble material and concentrated (twice) to give the title compound as a brown foam (2.54 g, quantitative yield).

HPLC RT 5.98; TSPMS ion (expected) 323 (322);

$^1$H NMR (CDCl$_3$) δ9.9 (br s, 1H), 8.5 (br s, 2H), 7.38 (s, 1H), 7.3–7.1 (m, 6H), 6.77 (m, 2H), 5.09 (q, J=7.6 Hz, 1H), 3.35 (dd, J=5.6, 7.6 Hz, 1H), 3.26 (dd, J=5.6, 7.6 Hz, 1H), 2.43 (s, 3H).

EXAMPLE 149

5-Fluoro-1H-indole-2-carboxylic acid {1-[2-(5-methoxy-1H-indole-3-yl)-ethylcarbamoyl]-2-phenyl-ethyl}-amide To 5.0 μmol of 2-[(5-fluoro-1H-indole-2-carbonyl)-amino]-3-phenyl-propionic acid (50 μL of a 0.1 mM solution in dimethylformamide) was added 1-(3-dimethylaminopropyl)-3-ethylcarbodiimide hydrochloride (50 μL of a 0.11 mM solution in DMF, 5.5 μmol) followed by 5-methoxytryptamine (50 μL of a 0.11 mM solution in DMF, 5.5 μmol). The reaction was agitated for 3 days and then concentrated to dryness. The crude product was partitioned between chloroform (0.5 mL) and water (0.25 mL) and the organic layer was then concentrated to give the title compound. TSPMS ion (expected) 499 (499); HPLC RT 6.78 (25%).

For the following examples, prepared analogously to Example 149, Examples 150–156 utilize 2-[(5-fluoro-1H-indole-2-carbonyl)-amino]-3-phenyl-propionic acid and Example 157–163 utilize 2-[(5-methyl-1H-indole-2-carbonyl)-amino]-3-phenyl-propionic acid.

EXAMPLE 150

5-Fluoro-1H-indole-2-carboxylic acid {1-[2-(1H-indol-3-yl)-1-methyl-ethylcarbamoyl]-2-phenyl-ethyl}-amide TSPMS ion (expected) 482 (483); HPLC RT unknown, several small peaks noted; est. purity<10%; % SM (HPLC) ND.

EXAMPLE 151

5-Fluoro-1H-indole-2-carboxylic acid [1-benzyl-2-(2-ethyl-piperidin-1-yl)-2-oxo-ethyl]-amide TSPMS ion (expected) 420 (421), HPLC RT 6.61 (40%).

EXAMPLE 152

5-Fluoro-1H-indole-2-carboxylic acid (1-cyclohexylcarbamoyl-2-phenyl-)-amide

TSPMS ion (expected) 408 (407); HPLC RT 6.60/7.11 (The two largest peaks are of roughly equal concentration.); est. purity (25%).

EXAMPLE 153

5-Fluoro-1H-indole-2-carboxylic acid {2-phenyl-1-[(thiophen-2-ylmethyl)-carbamoyl]-ethyl}-amide TSPMS ion (expected) 422 (421); HPLC RT 7.50 (50%).

EXAMPLE 154

5-Fluoro-1H-indole-2-carboxylic acid [1-benzyl-2-(3.4-dihydro-1H-isoquinolin-2-yl)-2-oxo-ethyl]-amide TSPMS ion (expected) 442 (441); HPLC RT 6.78 (35%), 5% SM.

EXAMPLE 155

5-Fluoro-1H-indole-2-carboxylic acid [1-(2-cyclohexen-1-yl-ethylcarbamoyl)-2-phenyl-ethyl]-amide TSPMS ion (expected) 434 (433); HPLC RT 6.27/6.60 (The two largest peaks are of roughly equal concentration.); est. purity (35%), 5% SM.

EXAMPLE 156

5-Fluoro-1H-indole-2-carboxylic acid [1-(5-cyano-pentyl-carbamoyl)-2-phenyl-ethyl]-amide TSPMS ion (expected) 421 (420); HPLC RT 6.61/7.71 (The two largest peaks are of roughly equal concentration.) (40%).

EXAMPLE 157

5-Methyl-1H-indole-2-carboxylic acid [2-phenyl-1-(thiochroman-4-ylcarbamoyl)-ethyl]-amide TSPMS ion (expected) 470 (470).

EXAMPLE 158

5-Methyl-1H-indole-2-carboxylic acid (1-cyclohexylcarbamoyl-2-phenyl-ethyl)-amide TSPMS ion (expected) 404 (404); HPLC RT 6.21 (70%).

EXAMPLE 159

5-Methyl-1H-indole-2-carboxylic acid (1-benzyl-2-morpholin-4-yl-2-oxo-ethyl)-amide TSPMS ion (expected) 392 (391); HPLC RT 6.86 (50%).

EXAMPLE 160

5-Methyl-1H-indole-2-carboxylic acid (1-benzyl-2-oxo-2-pyrrolidin-1-yl-ethyl)-amide TSPMS ion (expected) 376 (375); HPLC RT 6.50 (40%).

EXAMPLE 161

5-Methyl-1H-indole-2-carboxylic acid {2-phenyl-1-[(thiophen-2-ylmethyl)-carbamoyl]-ethyl}-amide TSPMS ion (expected) 418 (417); HPLC RT 7.89 (70%).

EXAMPLE 162

5-Methyl-1H-indole-2-carboxylic acid [1-(5-cyano-pentylcarbamoyl)-2-phenyl-ethyl]-amide TSPMS ion (expected) 417 (417); HPLC RT 6.49/6.88 (The two largest peaks are of roughly equal concentration.); (40%).

EXAMPLE 163

5-Methyl-1H-indole-2-carboxylic acid (1-cyclopentylcarbamoyl-2-phenyl-ethyl)-amide TSPMS ion (expected) 390 (389); HPLC RT 6.96 (55%).

EXAMPLE 164

{2-[(5-Chloro-1H-indole-2-carbonyl)-amino]-3-phenyl-propionylamino}-acetic acid methyl ester To 5.0 mmol of 5-chloro-1H-indole-2-carboxylic acid (50 mL of a 0.1 M solution in acetonitrile) was added 1-(3-dimethylaminopropyl)-3-ethylcarbodiimide hydrochloride (50 mL of a 0.10 M solution in acetonitrile, 5.0 mmol), 1-hydroxybenzotriazole (50 mL of a 0.10 M solution in acetonitrile, 5.0 mmol), followed by (2-amino-3-phenyl-propionylamino)-acetic acid methyl ester (50 mL of a 0.10 M solution in acetonitrile, 5.0 mmol). The reaction was agitated overnight at 80° C. and then concentrated to dryness to give the title compound.

HPLC RT 8.15 (65%).

EXAMPLE 165

2-(S)-[(5-Chloro-1H-indole-2-carbonyl)-amino]-3-phenyl-propionic acid benzyl ester The title compound was prepared by substituting L-phenylalanine benzyl ester for (2-amino-3-phenyl-propionyl-amino)-acetic acid methyl ester in a method analogous to that of Example 164 procedure.

HPLC RT 8.13 (40%).

EXAMPLE 166

5-Chloro-1H-indole-2-carboxylic acid [(1S)-benzyl-2-(3-hydroxy-azetidin-1-yl)-2-oxo-ethyl]-amide 2-Amino-1-(3-hydroxy-azetidin-1-yl)-3-phenyl-propan-1-one hydrochloride (1.18 mmol) and 5-chloro-1H-indole-2-carboxylic acid (1.18 mmol) were coupled according to Procedure A (4:1 dichloromethane-dimethylformamide reaction solvent) and the product purified by chromatography on silica gel eluted with 25%, 50%, 75% and 100% ethyl acetate-hexanes giving the title substance as a colorless foam (104 mg, 22%). A mixture (180 mg) of less polar products was also isolated. Title substance:

HPLC (60/40) 4.18 minutes (97%); TSPMS 398/400 (MH+, 100%);

EXAMPLE 166a (2S)-Amino-1-(3-hydroxy-azetidin-1-yl)-3-phenyl-propan-1-one hydrochloride

[(1S)-Benzyl-2-(3-hydroxy-azetidin-1-yl)-2-oxo-ethyl]-carbamic acid tert-butyl ester (515 mg, 1.6 mmol) was dissolved in cold 4N HCl-dioxane, the mixture stirred 2 h at 25° C., concentrated, and the residue with ether giving a colorless solid (415 mg, 100%).

EXAMPLE 167

5-Chloro-1H-indole-2-carboxylic acid [(1S)-benzyl-2-(3-hydroxylmino-azetidin-1-yl)-2-oxo-ethyl]-amide A solution of 5-chloro-1H-indole-2-carboxylic acid [(1S)-benzyl-2-(3-oxo-azetidin-1-yl)-2-oxo-ethyl]-amide (product of Example 170, 50 mg, 0.13 mmol), sodium acetate trihydrate (43 mg, 0.32 mmol) and hydroxylamine hydrochloride (18 mg, 0.25 mmol) in methanol (2 mL) was heated at reflux for 8 h and concentrated. The residue was partitioned between dichloromethane and saturated aqueous $NaHCO_3$. The organic layer was separated and dried giving a colorless solid which was triturated with ether-hexanes and dried (yield 36 mg, 69%): HPLC (50/50) 6.74 min (99%); TSPMS 411/413 (MH+, 10%), 180 (100%); $^1$H NMR (DMSO-$d_6$) δ11.75 (br, 1H), 11.10 (s, 0.5H), 11.08 (s, 0.5H), 8.99 (d, 1H, J=9 Hz), 7.73 (d, 1H, J=2 Hz), 7.4–7.1 (m, 8H), 5.0 (m, 1H), 4.8–4.5 (m, 4H), 3.1 (m, 2H).

EXAMPLE 168

5-Chloro-1H-indole-2-carboxylic acid [(1S)-benzyl-2-(4-hydroxyimino-piperidin-1-yl)-2-oxo-ethyl]-amide A mixture of 5-chloro-1H-indole-2-carboxylic acid [1(S)-benzyl-2-oxo-2-(4-oxo-piperidin-1-yl)-ethyl]-amide (406 mg, 0.96 mmol), hydroxylamine hydrochloride (80 mg, 1.15 mmol), and potassium carbonate, (159 mg, 1.15 mmol) in ethanol (6 mL) and water (1 mL) was stirred at 25° C. for 18 h and concentrated. The residue was dissolved in ethyl acetate and the resulting solution washed with water and dried (411 mg, 98%): HPLC (60/40) 5.13 minutes (97%); TSPMS 439/441 (MH+, 100%);

$^1$H NMR (DMSO-$d_6$) δ11.75 (br, 1H), 10.45 (s, 0.5H), 10.44 (s, 0.5H), 9.00 (m, 1H), 7.72 (d, 1H, J=2 Hz), 7.40 (d, 1H, J=8.8 Hz), 7.35–7.15 (m, 7H), 5.17 (m, 1H), 3.8–3.5 (m, 4H), 3.1 (m, 2H), 2.45 (m, 2H), 2.25 (m, 2H).

EXAMPLE 168a

5-Chloro-1H-indole-2-carboxylic acid [1(S)-benzyl-2-oxo-2-(4-oxo-piperidin-1-yl)-ethyl]-amide 5-Chloro-1H-indole-2-carboxylic acid [(1S)-benzyl-2-(4-hydroxy-piperidin-1-yl)-2-oxo-ethyl]-amide (Example 46, 669 mg) was added in one portion at 0° C. to a mixture of 1-(3-dimethylaminopropyl)3-ethylcarbodiimide hydrochloride (DEC, 1.80 g, 9.4 mmol) and dichloroacetic acid (307 mg, 1.5 mmol) in anhydrous toluene (e mL) and anhydrous dimethylsulfoxide (e mL). The mixture was stirred at 0–20° C. for 2 h, diluted with ethyl acetate, the resulting solution washed twice with 1N HCl, twice with saturated aqueous NaHCO3, dried, concentrated and the residue purified by chromatography on silica gel eluted with 25%, 50%, and 75% ethyl acetate-hexanes giving a foam (424 mg, 64%).

EXAMPLE 169

5-Chloro-1H-indole-2-carboxylic acid [(1S)-benzyl-2-(1,3-dihydro-isoindol-2-yl)-2-oxo-ethyl]-amide 2-Amino-1-(1,3-dihydro-isoindol-2-yl)-3-phenyl-propan-1-one hydrochloride (0.20 mmol) and 5-chloro-1H-indole-2-carboxylic acid (0.20 mmol) were coupled according to Procedure A and the product purified by chromatography on silica gel eluted with 5%, 10%, 20%, and 50% ethyl acetate-hexanes (55 mg, 62% yield): HPLC (70/30) 6.58 minutes (90%); TSPMS 444/446 (MH+, 50%), 180 (100%).

$^1$H NMR (CDCl$_3$) δ9.25 (br, 1H), 7.60 (s, 1H), 7.45 (m, ca. 1H), 7.3–7.1 (m, ca, 11H), 6.90 (5.25 (m, 1H), 5.0 (d, 1H, ca. 16 Hz), 4.85 (d, 1H, J=ca. 16 Hz), 4.70 (d, 1H), J=ca. 16 Hz), 4.20 (d, 1H, J=16 Hz).

EXAMPLE 169a (2S)-Amino-1-(1,3-dihydro-isoindol-2-yl)-3-phenyl-propane-1-one hydrochloride

[(1S)-Benzyl-2-(1,3-dihydro-isoindol-2-yl)-2-oxo-ethyl]-carbamic acid tert-butyl ester (88 mg) was dissolved in cold 4N HCl-dioxane (1.5 mL), stirred 2 h at 25° C., and the mixture concentrated. The residue was triturated with ether and dried (65 mg, 91%). TSPMS 267 (MH+, 100%).

EXAMPLE 169b

[(1S)-Benzyl-2-(1,3-dihydro-isoindol-2-yl)-2-oxo-ethyl]-carbamic acid tert-butyl ester N-t-Boc-L-phenylalanine (1 mmol) and isoindoline (J. Org. Chem. 1988, 53, p5382, 70–80% purity, 1 mmol) were coupled according to Procedure A and the product purified by chromatography on silica gel eluted with 20% and 50% ethyl acetate-hexanes giving an amber oil (88 mg, 23%): TSPMS 367 (MH+, 100%).

EXAMPLE 170

5-Chloro-1H-indole-2-carboxylic acid [(1S)-benzyl-2-(3-oxo-azetidin-1-yl)-2-oxo-ethyl]-amide 1-((2S)-Amino-3-phenyl-propionyl)-azetidin-3-one hydrochloride (3.2 mmol) and 5-chloro-1H-indole-2-carboxylic acid (3.2 mmol) were coupled according to Procedure A (0–25° C. reaction temperature) and the resulting yellow foam purified by chromatography on silica gel eluted with 20%, 30%, 40% and 50% ethyl acetate in hexane giving the title substance as a colorless foam (600 mg, 47%): HPLC (60/40) 5.09 minutes (98%); TSP-MS 396 (MH+, 100%); 1H NMR (CDCl$_3$) δ9.14 (br, 1H), 7.62 (d, 1H, J=3 Hz), 7.4–7.2 (m, 7H), 7.11 (d, 1H, J=8.0 Hz), 6.85 (m, 1H), 4.90 (m, 1H), 4.78 (m, 2H), 4.63 (m, 1H), 3.65 (m, 1H), 3.25 (dd, 1H, A of AB, J=5.1, 12.9 Hz), 3.10 (dd, 1H, B of AB, J=10, 12.9 Hz).

EXAMPLE 170A 1-((2S)-Amino-3-phenyl-propionyl)-azetidin-3-one hydrochloride

[(1S)-Benzyl-2-oxo-2-(3-oxo-azetidin-1-yl)-ethyl]-carbamic acid tert-butyl ester (297 mg, 0.9 mmol) was dissolved in 4N HCl-dioxane (3 mL). The resulting solution was stirred at 25° C. for 2 h, concentrated, and the residue triturated with ether and dried (196 mg, 82%).

EXAMPLE 170B

[(1S)-Benzyl-2-oxo-2-(3-oxo-azetidin-1-yl)-ethyl]-carbamic acid tert-butyl ester

[(1S)-Benzyl-2-(3-hydroxy-azetidin-1-yl)-2-oxo-ethyl]-carbamic acid tert-butyl ester (320 mg, 1 mmol) was added in one portion to a mixture of 1-(3-dimethylaminopropyl) 3-ethylcarbodiimide hydrochloride (DEC, 575 mg, 3 mmol) and dichloroacetic acid (192 mg, 1.5 mmol) in anhydrous toluene (2 mL) and anhydrous dimethylsulfoxide (2 mL). The mixture was stirred at 0–20° C. for 1 h, diluted with ethyl acetate, the resulting solution washed twice with 1N HCl, twice with saturated aqueous $NaHCO_3$, dried and concentrated giving a colorless solid (304 mg, 96%).

EXAMPLE 170C

[(1S)-Benzyl-2-(3-hydroxy-azetidin-1-yl)-2-oxo-ethyl]-carbamic acid tert-butyl ester 3-Hydroxyazetidine hydrochloride (J. Chem. Soc., Chem. Commun. 1968, p93, 27 mmol) and N-t-Boc-L-phenylalanine (27 mmol) were coupled according to Procedure A giving the title substance as a colorless foam (8.15 g, 93%).

EXAMPLE 171

5-Chloro-1H-benzoimidazole-2-carboxylic acid (1-dimethylcarbamoyl-2-phenyl-ethyl)-amide (S)-2-Amino-N,N-dimethyl-3-phenyl-propionamide hydrochloride (2.0 mmol) and 5-chloro-1H-benzoimidazole-2-carboxylic acid (Crowther et al., J. Chem. Soc. 1949, p.1268, 2.0 mmol) were coupled according to Procedure A and the product purified by chromatography on silica gel eluted with 1:1 ethyl acetate-hexanes (235 mg, 63%): HPLC (60/40) 4.92 min (91%); PBMS 371/373 (MH+, 100%); $^1$H NMR (CDCl$_3$) δ11.25 (br, 0.6H), 10.9 (br, 0.4H), 8.36 (m, 1H), 7.78 (d, 0.4H, J=7.72 (d, 0.6H, J=8.8 Hz), 7.52 (d, 0.6H, J=2 Hz), 7.41 (d, 0.4H, J=8.4 Hz), 7.35–7.1 (m, 6H), 7.35 (m, 1H), 3.16 (m, 2H), 2.90 (s, 3H), 2.68 (s, ca. 2H), 2.67 (s, ca. 1H).

EXAMPLE 172

5-Chloro-1H-indole-2-carboxylic acid [1-benzyl-2-oxo-2-(2-oxo-oxazolidin-3-yl)-ethyl]-amide 3-((2S)-Amino-3-phenyl-propionyl)-oxazolidin-2-one hydrochloride (0.50 mmol) and 5-chloro-1H-indole-2-carboxylic acid (0.50 mmol) were coupled according to Procedure A (3:1 dimethylforrnamide-dichloromethane reaction solvent) and the product triturated with 2:1 ether-hexanes and dried (130 mg, 63%): HPLC (60/40) 6.22 minutes (95%); TSPMS 429/431 (45%, MH+NH3), 412/414 (30%, MH+), 325/327 (100%). $^1$H NMR (DMSO-d6) δ11.68 (br, 1H), 8.92 (d, 1H, J=8.5 Hz), 7.75 (s, 1H), 7.42 (m, 3H), 7.26 (m, 3H), 7.18 (m, 2H), 5.83 (m, 1H), 4.50 (m, 2H) 4.0 (m, 1H), 3.25 (m, 1H), 2.95 (m, 1H).

EXAMPLE 172a 3-((2S)-Amino-3-phenyl-propionyl)-oxazolidin-2-one hydrochloride

[(1S)-Benzyl-2-oxo-2-(2-oxo-oxazolidin-3-yl)-ethyl]-carbamic acid tert-butyl ester (2.29 g, 6.68 mmol) was dissolved in 4N HCl-dioxane (10 mL) at 0° C. The resulting solution was stirred at 25° C. for 2 h, concentrated, and the residue triturated with ether and dried (1.98 g, 107%).

EXAMPLE 172b

[(1S)-Benzyl-2-oxo-2-(2-oxo-oxazolidin-3-yl)-ethyl]-carbamic acid tert-butyl ester N-Butyllithium (2.35 M in hexanes, 11.5 mL) was added at −78° C. to a solution of 2-oxazolidinone (2.04 g, 23.4 mmol) in tetrahydrofuran (25 mL). After 30 minutes at −78° C. the solution was treated with N-t-Boc-L-phenylalanine N-hydroxysuccinimide ester (9.31 g, 25.7 mmol) in tetrahydrofuran (10 mL), and the stirred mixture was allowed to warm to 25° C. overnight. Water (10 mL) was added, and the resulting mixture concentrated, the residue dissolved in ethyl acetate, and the resulting solution washed twice with 1N NaOH, once with water, once with brine, dried, and concentrated. The residue was chromatographed on silica gel eluted with 25% and 50% ethyl acetate in hexanes giving a colorless solid (3.42 g, 44%).

It should be understood that the invention is not limited to the particular embodiments described herein, but that various changes and modifications may be made without departing from the spirit and scope of this novel concept as defined by the following claims.

What is claimed is:

1. An intermediate of Formula QZ

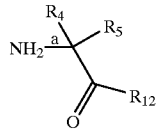

Formula QZ wherein $R_5$ is H;

$R_4$ is phenylmethyl, thien-2- or -3-ylmethyl, fur-2- or -3-ylmethyl wherein said rings are optionally mono- or di-substituted with fluoro; and $R_{12}$ is thiazolidin-3-yl, 1-oxothiazolidin-3-yl, 1,1-dioxothiazolidin-3-yl, pyrrolidin-1-yl, piperidin-1-yl, azetidin-1-yl, 1,2-oxazinan-2-yl, isoxazolidin-2-yl, isothiazolidin-2-yl, 1,2-oxazetidin-2-yl or oxazolidin-3-yl, wherein said $R_{12}$ rings are mono- or di-substituted independently with halo, $(C_1–C_5)$alkyl, $(C_1–C_5)$alkoxy, hydroxy, amino, mono-N— or di-N,N—$(C_1–C_5)$alkylamino, formyl, carbamoyl, mono-N— or di-N,N—$(C_1–C_5)$alkylcarbamoyl, hydroxy$(C_1–C_5)$alkyl, amino$(C_1–C_4)$alkyl, mono-N— or di-N,N—$(C_1–C_4)$alkylamino$(C_1–C_4)$alkyl, oxo, hydroxyimino or $(C_1–C_6)$alkoxyimino with the proviso that only the $R_{12}$ heterocycles thiazolidin-3-yl, pyrrolidin-1-yl, piperidin-1-yl, azetidin-1-yl, 1,2-oxazinan-2-yl, isoxazolidin-2-yl, or oxazolidin-3-yl are optionally mono- or di-substituted independently with oxo, hydroxyimino, or $(C_1–C_6)$alkoxyimino; and wherein said $R_{12}$ rings are optionally additionally mono- or di-substituted independently with $(C_1–C_5)$alkyl and with the proviso that $R_{12}$ is not 2-carboxy-4-hydroxy-pyrrolidin-1-yl, 2-(($C_1–C_5$)alkoxycarbonyl)-4-hydroxy-pyrrolidin-1-yl, 2-carboxy-piperidin-1-yl or 2-(($C_1–C_5$)alkoxycarbonyl)-piperidin-1-yl.

2. A compound as recited in claim 1 wherein $R_4$ is phenylmethyl, said phenyl optionally mono- or di-substituted with fluoro; and $R_{12}$ is 3-mono-substituted azetidin-1-yl, 3-mono- or 3,4-disubstituted pyrrolidin-1-yl, 3-, 4-, or 5-mono- or di-substituted piperidin-1-yl, thiazolidin-3-yl, 1-oxo-thiazolidin-3-yl or 1,1-dioxothiazolidin-3-yl wherein said pyrrolidin-1-yl or piperidin-1-yl are mono- or di-substituted independently with hydroxy, oxo, hydroxyimino, amino, mono-N— or di-N,N—$(C_1–C_4)$alkylamino, or carboxy and said $R_{12}$ rings are optionally additionally mono- or di-substituted independently with $(C_1-C_4)$alkyl.

3. The compound as recited in claim 1 wherein $R_4$ is H; and $R_{12}$ is thiazolidin-3-yl.

4. The compound as recited in claim 1 wherein $R_4$ is H; and $R_{12}$ is 1,1-dioxo-thiazolidin-3-yl.

5. A compound as recited in claim 1 wherein $R_4$ is H; and $R_{12}$ is 1-oxo-thiazolidin-3-yl.

6. A compound as recited in claim 2 wherein $R_4$ is benzyl;

$R_{12}$ is 3-hydroxypyrrolidin-3-yl; and the stereochemistry of carbon (a) is (S).

7. The compound as recited in claim 2 wherein $R_4$ is benzyl;

$R_{12}$ is 3-hydroxyazetidin-1-yl; and the stereochemistry of carbon (a) is (S).

8. A compound as recited in claim 2 wherein $R_4$ is benzyl;

$R_{12}$ is 3,4-dihydroxypyrrolidin-1-yl; and the stereochemistry of carbon (a) is (S).

9. The compound as recited in claim 2 wherein $R_4$ is benzyl;

$R_{12}$ is 4-hydroxypiperidin-1-yl; and the stereochemistry of carbon (a) is (S).

10. The compound as recited in claim 2 wherein $R_4$ is 4-fluorophenylmethyl;

$R_{12}$ is 4-hydroxypiperidin-1-yl; and the stereochemistry of carbon (a) is (S).

11. The compound as recited in claim 2 wherein $R_4$ is benzyl;

$R_{12}$ is 4-hydroxyiminoazetidin-1-yl; and the stereochemistry of carbon (a) is (S).

12. A pharmaceutical composition which comprises a therapeutically effective amount of a) a glycogen phosphorylase inhibitor;

b) an antidiabetic agent selected from insulin and insulin analogs; insulinotropin; Sulfonylureas and analogs; Biguanides; α2-Antagonists and Imidazolines; insulin secretagogues; Glitazones; Fatty Acid Oxidation inhibitors; α-Glucosidase inhibitors; β-Agonists; Phosphodiesterase Inhibitors; Lipid-lowering Agents; Antiobesity Agents; Vanadate and vanadium complexes and peroxovanadium complexes; Amylin Antagonists; Glucagon Antagonists; Gluconeogenesis Inhibitors; Somatostatin Analogs; Antilipotic Agents; and c) optionally a pharmaceutically acceptable carrier.

13. The pharmaceutical composition as recited in claim 12 wherein the glycogen phosphorylase inhibitor is a compound of Formula I

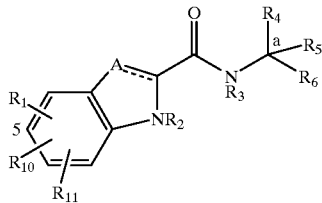

Formula 1 and the pharmaceutically acceptable salts and prodrugs thereof wherein the dotted line (---) is an optional bond;

A is —C(H)=, —C(($C_1-C_4$)alkyl)=, —C(halo)= or —N=, when the dotted line (---) is a bond, or A is methylene or —CH(($C_1-C_4$)alkyl)-, when the dotted line (---) is not a bond;

$R_1$, $R_{10}$ or $R_{11}$ are each independently H, halo, cyano, 4-, 6-, or 7-nitro, ($C_1-C_4$)alkyl, ($C_1-C_4$)alkoxy, fluoromethyl, difluoromethyl or trifluoromethyl;

$R_2$ is H;

$R_3$ is H or ($C_1-C_5$)alkyl;

$R_4$ is H, methyl, ethyl, n-propyl, hydroxy($C_1-C_3$)alkyl, ($C_1-C_3$)alkoxy($C_1-C_3$)alkyl, phenyl($C_1-C_4$)alkyl, phenylhydroxy($C_1-C_4$)alkyl, (phenyl)(($C_1-C_4$)-alkoxy)($C_1-C_4$)alkyl, thien-2- or -3-yl($C_1-C_4$)alkyl or fur-2- or -3-yl($C_1-C_4$)alkyl wherein said $R_4$ rings are mono-, di- or tri-substituted independently on carbon with H, halo, ($C_1-C_4$)alkyl, ($C_1-C_4$)alkoxy, trifluoromethyl, hydroxy, amino, cyano or 4,5-dihydro-1H-imidazol-2-yl; or $R_4$ is pyrid-2-, -3- or -4-yl($C_1-C_4$)alkyl, thiazol-2-, -4- or -5-yl($C_1-C_4$)alkyl, imidazol-2-, -4- or -5-yl($C_1-C_4$) alkyl, pyrrol-2- or -3-yl($C_1-C_4$)alkyl, oxazol-2-, -4- or -5-yl($C_1-C_4$)alkyl, pyrazol-3-, -4- or -5-yl($C_1-C_4$) alkyl, isoxazol-3-, -4- or -5-yl($C_1-C_4$)alkyl, isothiazol-3-, -4- or -5-yl($C_1-C_4$)alkyl, pyridazin-3- or -4-yl ($C_1-C_4$)alkyl, pyrimidin-2-, -4-, -5- or -6-yl($C_1-C_4$) alkyl, pyrazin-2- or -3-yl($C_1-C_4$)alkyl, 1,3,5-triazin-2-yl($C_1-C_4$)alkyl or indol-2-($C_1-C_4$)alkyl, wherein said preceding $R_4$ heterocycles are optionally mono- or di-substituted independently with halo, trifluoromethyl, ($C_1-C_4$)alkyl, ($C_1-C_4$)alkoxy, amino, hydroxy or cyano and said substituents are bonded to carbon; or $R_4$ is $R_{15}$-carbonyloxymethyl, wherein said $R_{15}$ is phenyl, thiazolyl, imidazolyl, 1H-indolyl, furyl, pyrrolyl, oxazolyl, pyrazolyl, isoxazolyl, isothiazolyl, pyridyl, pyridazinyl, pyrimidinyl, pyrazinyl or 1,3,5-triazinyl and wherein said preceding $R_{15}$ rings are optionally mono- or di-substituted independently with halo, amino, hydroxy, ($C_1-C_4$)alkyl, ($C_1-C_4$)alkoxy or trifluoromethyl and said mono- or di-substituents are bonded to carbon;

$R_5$ is H;

$R_6$ is carboxy, ($C_1-C_8$)alkoxycarbonyl, benzyloxycarbonyl, C(O)NR$_8$R$_9$ or C(O)R$_{12}$ wherein $R_8$ is H, ($C_1-C_6$)alkyl, cyclo($C_3-C_6$)alkyl, cyclo ($C_3-C_6$)alkyl($C_1-C_5$)alkyl, hydroxy or ($C_1-C_8$) alkoxy; and $R_9$ is H, cyclo($C_3-C_8$)alkyl, cyclo($C_3-C_8$)alkyl($C_1-C_5$) alkyl, cyclo($C_4-C_7$)alkenyl, cyclo($C_3-C_7$)alkyl ($C_1-C_5$)alkoxy, cyclo($C_3-C_7$)alkyloxy, hydroxy, methylene-perfluorinated($C_1-C_8$)alkyl, phenyl, or a heterocycle wherein said heterocycle is pyridyl, furyl, pyrrolyl, pyrrolidinyl, oxazolyl, thiazolyl, imidazolyl, pyrazolyl, pyrazolinyl, pyrazolidinyl, isoxazolyl, isothiazolyl, pyranyl, pyridinyl, piperidinyl, morpholinyl, pyridazinyl, pyrimidinyl, pyrazinyl, piperazinyl, 1,3,5-triazinyl, benzothiazolyl, benzoxazolyl, benzimidazolyl, thiochromanyl or tetrahydrobenzothiazolyl wherein said heterocycle rings are carbon-nitrogen linked; or $R_9$ is $(C_1-C_6)$alkyl or $(C_1-C_8)$alkoxy wherein said $(C_1-C_6)$alkyl or $(C_1-C_8)$alkoxy is optionally mono-substituted with cyclo$(C_4-C_7)$alken-1-yl, phenyl, thienyl, pyridyl, furyl, pyrrolyl, pyrrolidinyl, oxazolyl, thiazolyl, imidazolyl, pyrazolyl, pyrazolinyl, pyrazolidinyl, isoxazolyl, isothiazolyl, pyranyl, piperidinyl, morpholinyl, thiomorpholinyl, 1-oxothiomorpholinyl, 1,1-dioxothiomorpholinyl, pyridazinyl, pyrimidinyl, pyrazinyl, piperazinyl, 1,3,5-triazinyl or indolyl and wherein said $(C_1-C_6)$alkyl or $(C_1-C_8)$alkoxy are optionally additionally independently mono- or di-substituted with halo, hydroxy, $(C_1-C_5)$alkoxy, amino, mono-N— or di-N,N—$(C_1-C_5)$alkylamino, cyano, carboxy, or $(C_1-C_4)$alkoxycarbonyl; and wherein the $R_9$ rings are optionally mono- or di-substituted independently on carbon with halo, $(C_1-C_4)$alkyl, $(C_1-C_4)$alkoxy, hydroxy, hydroxy$(C_1-C_4)$alkyl, amino$(C_1-C_4)$alkyl, mono-N— or di-N,N—$(C_1-C_4)$alkylamino$(C_1-C_4)$alkyl, $(C_1-C_4)$alkoxy$(C_1-C_4)$alkyl, amino, mono-N— or di-N,N—$(C_1-C_4)$alkylamino, cyano, carboxy, $(C_1-C_5)$alkoxycarbonyl, carbamoyl, formyl or trifluoromethyl and said $R_9$ rings may optionally be additionally mono- or di-substituted independently with $(C_1-C_5)$alkyl or halo;

with the proviso that no quaternized nitrogen on any $R_9$ heterocycle is included;

$R_{12}$ is morpholino, thiomorpholino, 1-oxothiomorpholino, 1,1-dioxothiomorpholino, thiazolidin-3-yl, 1-oxothiazolidin-3-yl, 1,1-dioxothiazolidin-3-yl, pyrrolidin-1-yl, piperidin-1-yl, piperazin-1-yl, piperazin-4-yl, azetidin-1-yl, 1,2-oxazinan-2-yl, pyrazolidin-1-yl, isoxazolidin-2-yl, isothiazolidin-2-yl, 1,2-oxazetidin-2-yl, oxazolidin-3-yl, 3,4-dihydroisoquinolin-2-yl, 1,3-dihydroisoindol-2-yl, 3,4-dihydro-2H-quinol-1-yl, 2,3-dihydro-benzo[1,4]oxazin-4-yl, 2,3-dihydro-benzo[1,4]-thiazine-4-yl, 3,4-dihydro-2H-quinoxalin-1-yl, 3,4-dihydro-benzo[c][1,2]oxazin-1-yl, 1,4-dihydro-benzo[d][1,2]oxazin-3-yl, 3,4-dihydro-benzo[e][1,2]-oxazin-2-yl, 3H-benzo[d]isoxazol-2-yl, 3H-benzo[c]isoxazol-1-yl or azepan-1-yl, wherein said $R_{12}$ rings are optionally mono-, di- or tri-substituted independently with halo, $(C_1-C_5)$alkyl, $(C_1-C_5)$alkoxy, hydroxy, amino, mono-N— or di-N,N—$(C_1-C_5)$alkylamino, formyl, carboxy, carbamoyl, mono-N— or di-N,N—$(C_1-C_5)$alkylcarbamoyl, $(C_1-C_6)$alkoxy$(C_1-C_3)$alkoxy, $(C_1-C_5)$alkoxycarbonyl, benzyloxycarbonyl, $(C_1-C_5)$alkoxycarbonyl$(C_1-C_5)$alkyl, $(C_1-C_4)$alkoxycarbonylamino, carboxy$(C_1-C_5)$alkyl, carbamoyl$(C_1-C_5)$alkyl, mono-N— or di-N,N—$(C_1-C_5)$alkylcarbamoyl$(C_1-C_5)$alkyl, hydroxy$(C_1-C_5)$alkyl, $(C_1-C_4)$alkoxy$(C_1-C_4)$alkyl, amino$(C_1-C_4)$alkyl, mono-N— or di-N,N—$(C_1-C_4)$alkylamino$(C_1-C_4)$alkyl, oxo, hydroxyimino or $(C_1-C_6)$alkoxyimino and wherein no more than two substituents are selected from oxo, hydroxyimino or $(C_1-C_6)$alkoxyimino and oxo, hydroxyimino or $(C_1-C_6)$alkoxyimino are on nonaromatic carbon; and wherein said $R_{12}$ rings are optionally additionally mono- or di-substituted independently with $(C_1-C_5)$alkyl or halo;

with the proviso that when $R_6$ is $(C_1-C_5)$alkoxycarbonyl or benzyloxycarbonyl then $R_1$ is 5-halo, 5-$(C_1-C_4)$alkyl or 5-cyano and $R_4$ is (phenyl)(hydroxy)$(C_1-C_4)$alkyl, (phenyl)($(C_1-C_4)$alkoxy)$(C_1-C_4)$alkyl, hydroxymethyl or Ar$(C_1-C_2)$alkyl, wherein Ar is thien-2- or -3-yl, fur-2- or -3-yl or phenyl wherein said Ar is optionally mono- or di-substituted independently with halo;

with the proviso that when $R_1$ and $R_{10}$ and $R_{11}$ are H, $R_4$ is not imidazol-4-ylmethyl, 2-phenylethyl or 2-hydroxy-2-phenylethyl;

with the proviso that when both $R_8$ and $R_9$ are n-pentyl, $R_1$ is 5-chloro, 5-bromo, 5-cyano, 5$(C_1-C_5)$alkyl, 5$(C_1-C_5)$alkoxy or trifluoromethyl;

with the proviso that when $R_{12}$ is 3,4-dihydroisoquinol-2-yl, said 3,4-dihydroisoquinol-2-yl is not substituted with carboxy($(C_1-C_4)$alkyl;

with the proviso that when $R_8$ is H and $R_9$ is $(C_1-C_6)$alkyl, $R_9$ is not substituted with carboxy or $(C_1-C_4)$alkoxycarbonyl on the carbon which is attached to the nitrogen atom N of NHR$_9$; and with the proviso that when $R_6$ is carboxy and $R_1$, $R_{10}$, $R_{11}$ and $R_5$ are all H, then $R_4$ is not benzyl, H, (phenyl)(hydroxy)methyl, methyl, ethyl or n-propyl.

\* \* \* \* \*